United States Patent
Wagner et al.

(10) Patent No.: US 11,400,139 B2
(45) Date of Patent: Aug. 2, 2022

(54) ANTI-NET COMPOUNDS FOR TREATING AND PREVENTING FIBROSIS AND FOR FACILITATING WOUND HEALING

(71) Applicant: THE CHILDREN'S MEDICAL CENTER CORPORATION, Boston, MA (US)

(72) Inventors: Denisa D. Wagner, Dover, MA (US); Siu Ling Wong, Brookline, MA (US); Kimberly Lindsay Martinod, Kortrijk (BE); Luise Erpenbeck, Göttingen (DE); Jörn Thilo Witsch, Freiburg (DE); Alexander Savchenko, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 74 days.

(21) Appl. No.: 15/544,618

(22) PCT Filed: Jan. 19, 2016

(86) PCT No.: PCT/US2016/013847
§ 371 (c)(1),
(2) Date: Jul. 19, 2017

(87) PCT Pub. No.: WO2016/118476
PCT Pub. Date: Jul. 28, 2016

(65) Prior Publication Data
US 2018/0271953 A1    Sep. 27, 2018

Related U.S. Application Data

(60) Provisional application No. 62/105,342, filed on Jan. 20, 2015.

(51) Int. Cl.
*A61K 38/46* (2006.01)
*A61K 45/06* (2006.01)

(52) U.S. Cl.
CPC ............ *A61K 38/465* (2013.01); *A61K 45/06* (2013.01); *C12Y 301/21001* (2013.01)

(58) Field of Classification Search
CPC .................. A61K 38/465; A61K 45/06; C12Y 301/21001
See application file for complete search history.

(56) References Cited

U.S. PATENT DOCUMENTS

| | | |
|---|---|---|
| 5,336,501 A | 8/1994 | Czech et al. |
| 6,919,320 B1 * | 7/2005 | von Borstel ........... A61K 31/70 514/45 |

(Continued)

FOREIGN PATENT DOCUMENTS

| | | | |
|---|---|---|---|
| WO | WO-2012166611 A2 * | 12/2012 | ............ A61K 45/06 |
| WO | 2014/135469 A2 | 9/2014 | |
| WO | 2014168253 A1 | 10/2014 | |

OTHER PUBLICATIONS

Oken et al. The effect of prophylactic dose of a low molecular weight heparin on skin wound healing of rats. Acta Cirurgica Brasileira (2009), 24(6), 471-475 (Year: 2009).*

(Continued)

*Primary Examiner* — Sean C. Barron
(74) *Attorney, Agent, or Firm* — Nixon Peabody LLP; Davids S. Resnick; Ravinderjit Braich

(57) ABSTRACT

Embodiments of the technology described herein are based, in part, upon the discovery that NETosis, the formation of neutrophil extracellular traps (NETs) is increased in wounds, in organ fibrosis and in subjects with diabetes. Accordingly, methods for treating wounds, fibrosis and NET associated complications in diabetes are provided. The methods comprise administrating a therapeutically effective amount of at least one anti-NET compound to a subject in need of treatment, e.g. a PAD 4 inhibitor, a DNase, a histone-degrading enzyme; an inhibitor of chromatin decondensa- (Continued)

tion; an antibody against a component of a NET; an inhibitor of NET release, a protease inhibitor, or an elastase inhibitor.

15 Claims, 22 Drawing Sheets

Specification includes a Sequence Listing.

(56)  References Cited

U.S. PATENT DOCUMENTS

| | | | |
|---|---|---|---|
| 7,297,526 | B2 | 11/2007 | Shak |
| 8,617,542 | B2 | 12/2013 | Madhyastha et al. |
| 2014/0199329 | A1 | 7/2014 | Wagner et al. |
| 2014/0377323 | A1 | 12/2014 | Morgelin et al. |

OTHER PUBLICATIONS

Brown et al. Effects of heparin and related molecules upon neutrophil aggregation and elastase release in vitro. British Journal of Pharmacology (2003), 139, 845-853. (Year: 2003).*

Ravikumar et al. Low Molecular Weight Heparin-Induced Pharmacological Modulation of Burn Wound Healing. Annals of Burns and Fire Disasters (2006), 19(3), 123-129 (Year: 2006).*

Pullen et al. Prospective randomized double-blind study of the wound-debriding effects of collagenase and fibrinolysin/deoxyribonuclease in pressure ulcers. Age and Aging (2002), 31, 126-130 (Year: 2002).*

Kruse et al. Evaluation and Treatment of Diabetic Foot Ulcers. Clinical Diabetes (2006), 24(2), 91-93 (Year: 2006).*

Knight et al. Peptidylarginine deiminase inhibition disrupts NET formation and protects against kidney, skin and vascular disease in lupus-prone MRL/lpr mice. Ann Rheum Dis. (epub Aug. 2014), 17 page author manuscript. (Year: 2014).*

Sawicki et al. Reduced Mortality in Cystic Fibrosis Patients Treated With Tobramycin Inhalation Solution. Pediatric Immunology (2012), 47(1), 44-52. (Year: 2012).*

Wartha et al. Neutrophil extracellular traps: casting the NET over pathogenesis. Current Opinion in Microbiology (2007), 10, 52-56. (Year: 2007).*

Thomas et al., "Extracellular DNA traps are associated with the pathogeneis of TRAIL in humans and mice", Blood 119(26):6335-6343 (2012).

Wang et al., "Increased Neutrophil Elastase and Proteinase 3 and Augmented NETosis Are Closely Associated With β-cell Autoimmunity in Patients With Type 1 Diabetes", Diabetes 63(12):4239-4248 (2014).

Yipp et al., "NETosis: how vital is it?", Blood 122(16):2784-2794 (2013).

Das et al. "Influence of calcium in extracellular DNA mediated bacterial aggregation and biofilm formation." PloS one 9.3 (2014): e91935.

Datta, "Diabetes, Chronic Inflammation and Neutrophils—another part of the story", In Scientio, Veritas (2012).

Doring et al., "Neutrophils cast NETs in atherosclerosis: employing peptidylarginine deiminase as a therapeutic target", Circ Res 114(6) 931-934 (2014).

Fuchs et al., "Effect of aerosolized recombinant human DNase on exacerbations of respiratory symptoms and on pulmonary function in patients with cystic fibrosis. The Pulmozyme Study Group.", N Engl J Med 331(10) 637-642 (1994).

Lin et al. "Sulfasalazine and thalidomide inhibit extracellular trap formation by human neutrophils." Journal of Investigative Dermatology. vol. 133. 75 Varick St, 9th Flr, New York, NY 10013-1917 USA: Nature Publishing Group, 2013. *Abstract Only*.

Martinod et al., "Peptidylarginine deiminase 4 promotes age-related organ fibrosis", J Exp Med 214(2) 439-458 (2017).

Pullen et al. "Prospective randomized double-blind study of the wound-debriding effects of collagenase and fibrinolysin/deoxyribonuclease in pressure ulcers." Age and ageing 31.2 (2002): 126-130.

Saffarzadeh et al., "Fighting against the dark side of neutrophil extracellular traps in disease: manoeuvres for host protection", Curr Opin Hematol 20(1) 3-9 (2013).

Shi et al., "Effects of heparin on liver fibrosis in patients with chronic hepatitis B", World J Gastroenterol 9(7) 1611-1614 (2003).

Singhal et al."Options for nonsurgical debridement of necrotic wounds", Adv Skin Would Care 14(2) 96-100 (2001).

Vassiliadis et al., "Peptidyl arginine deiminase inhibitor effect on hepatic fibrogenesis in a CCl4 pre-clinical model of liver fibrosis", Am J Transl Res 5(4) 465-469 (2013).

Wong et al. "Diabetes primes neutrophils to undergo NETosis, which impairs wound healing." Nature medicine 21.7 (2015): 815-819.

Saffarzadeh et al., "Fighting against the dark side of neutrophil extracellular traps in disease: manoeuvres for host protection." Current opinion in hematology 20.1 (2013): 3-9.

Chrysanthopoulou, Akrivi, et al. "Neutrophil extracellular traps promote differentiation and function of fibroblasts." The Journal of pathology 233.3 (2014): 294-307.

* cited by examiner

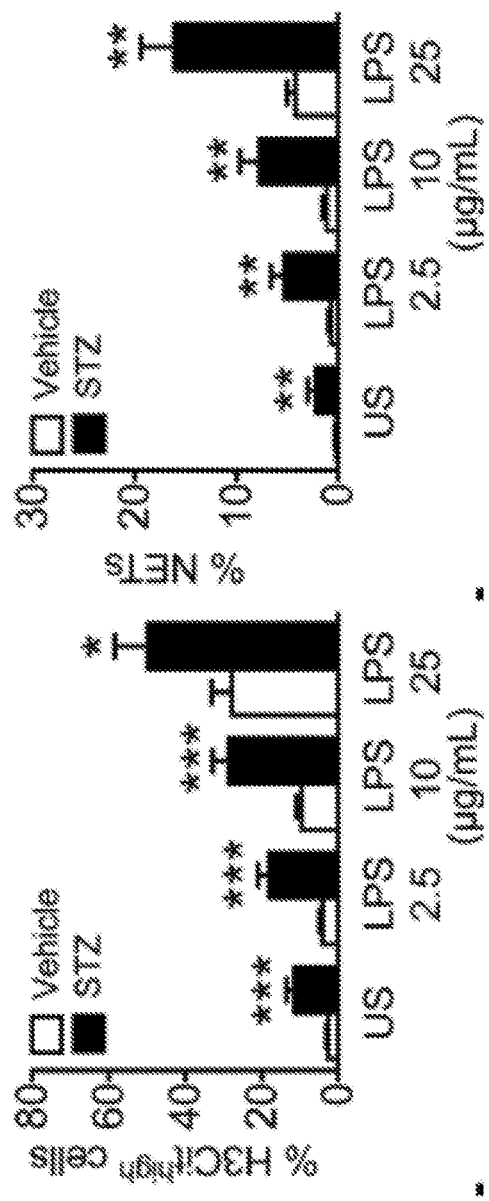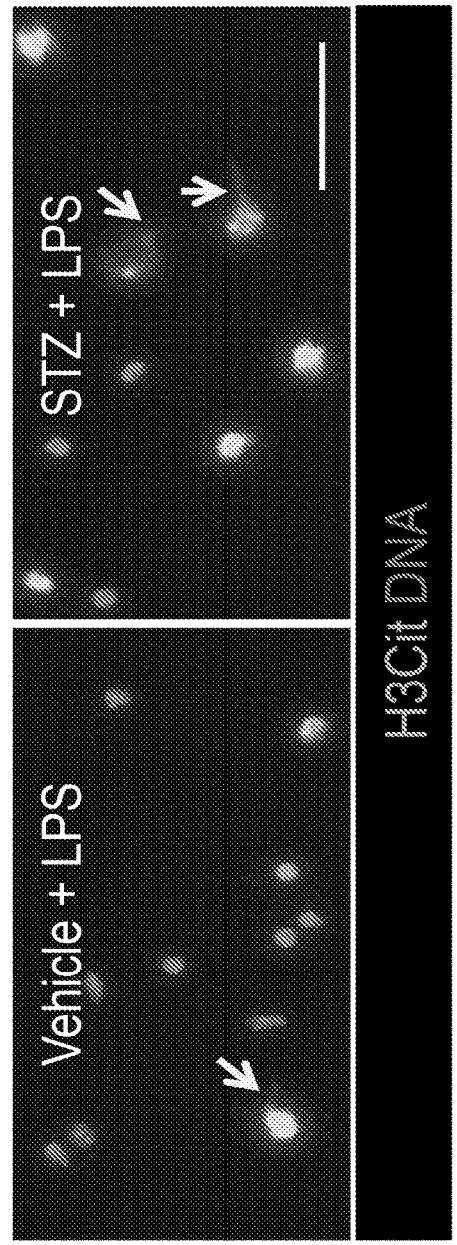
FIG. 1E  FIG. 1F  FIG. 1G

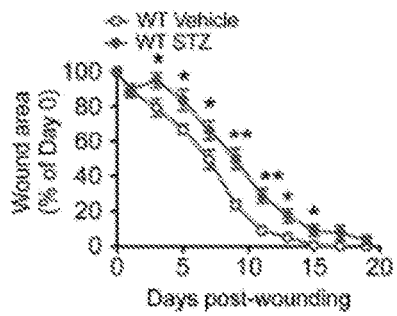
*FIG. 4A*
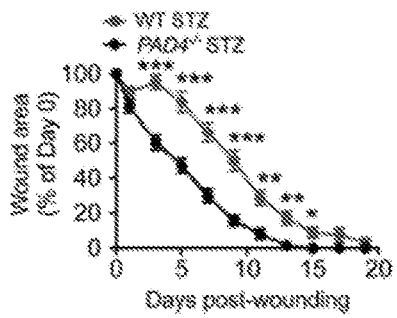
*FIG. 4B*
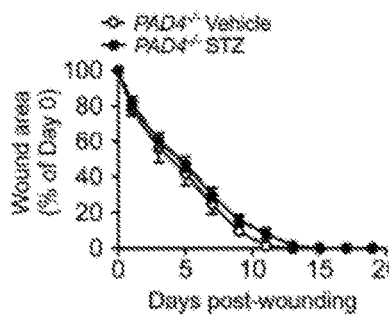
*FIG. 4C*
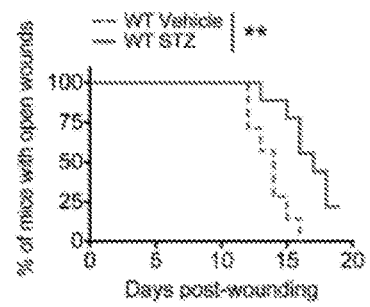
*FIG. 4D*
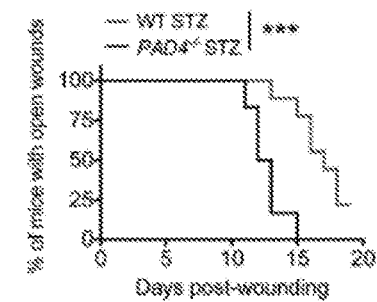
*FIG. 4E*
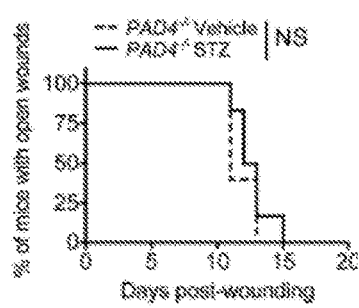
*FIG. 4F*
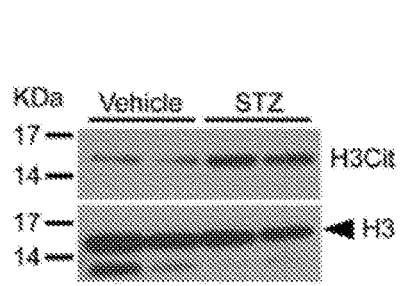
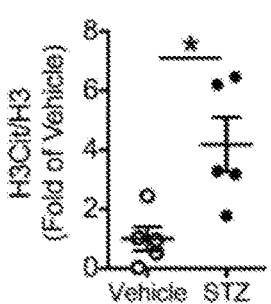
*FIG. 4G*
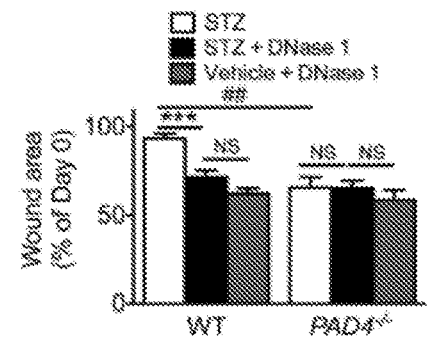
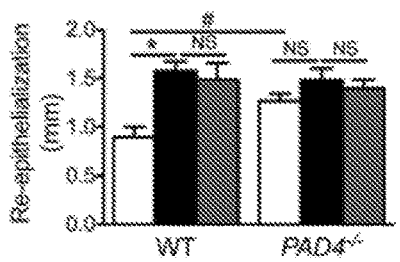
*FIG. 4H*
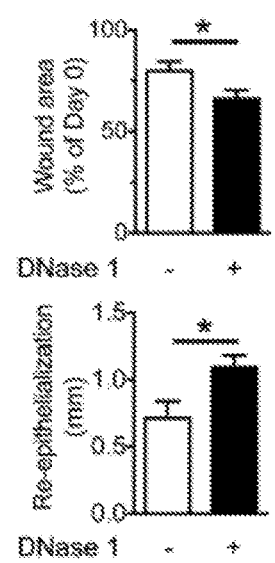
*FIG. 4I*

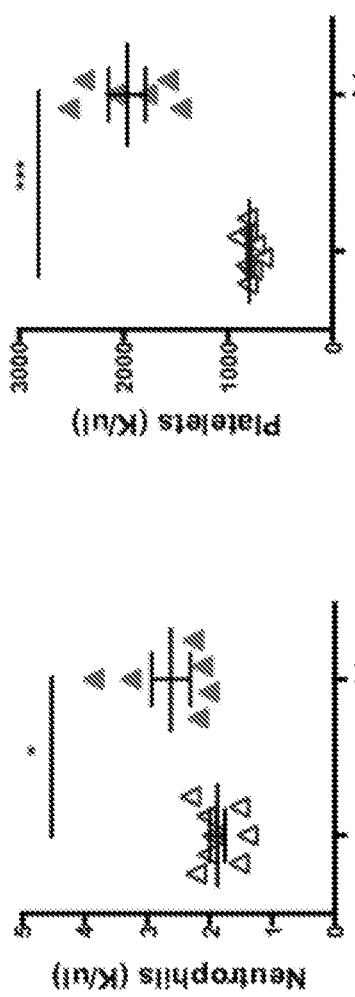
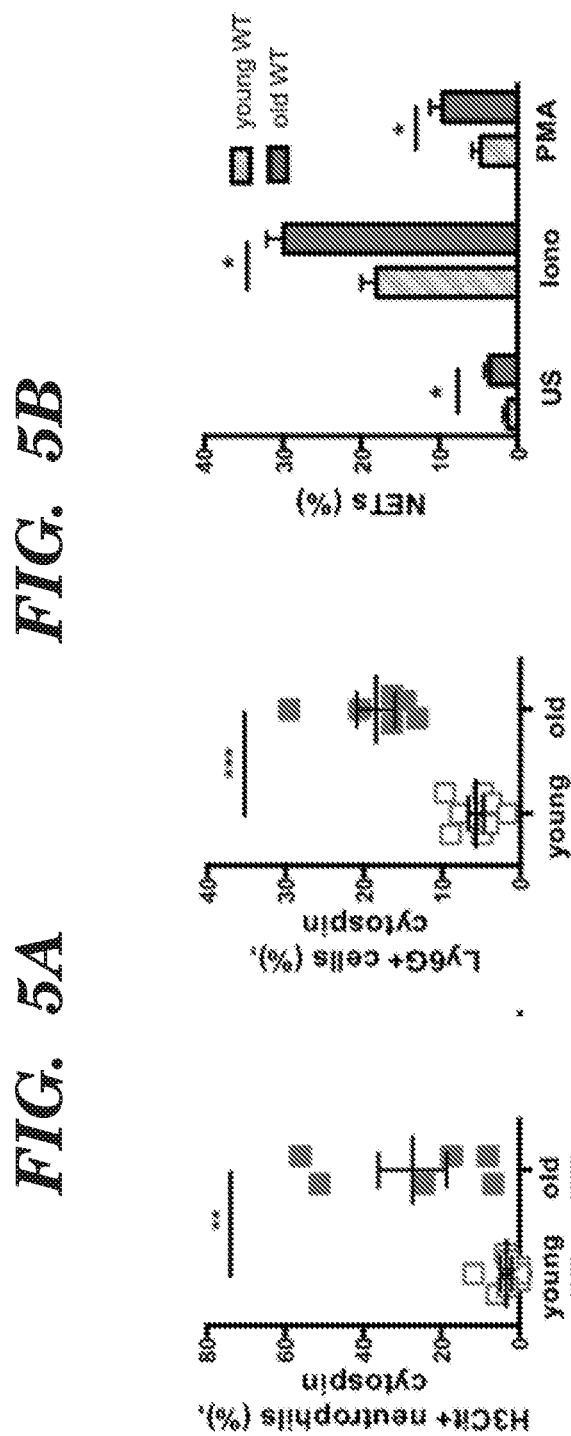

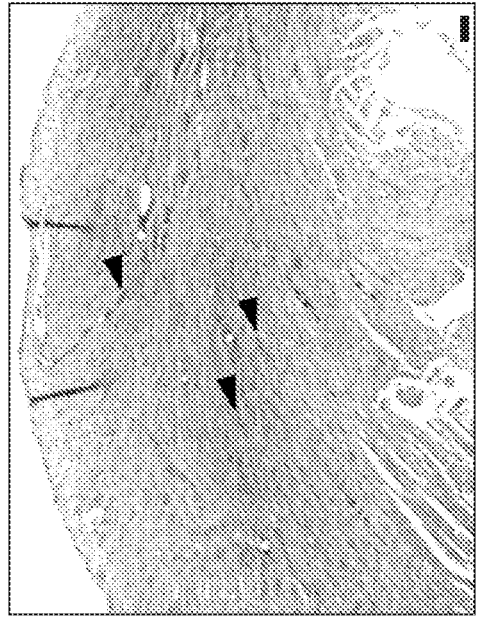
FIG. 7C
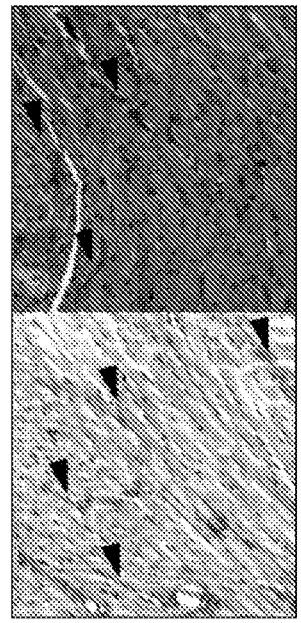
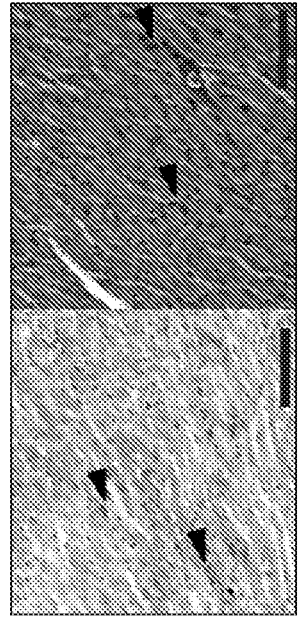
FIG. 7D

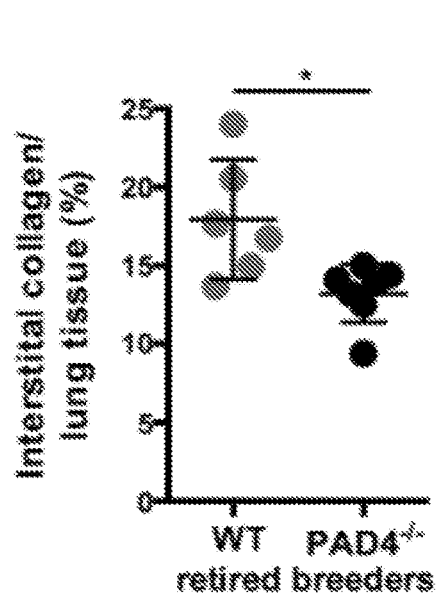
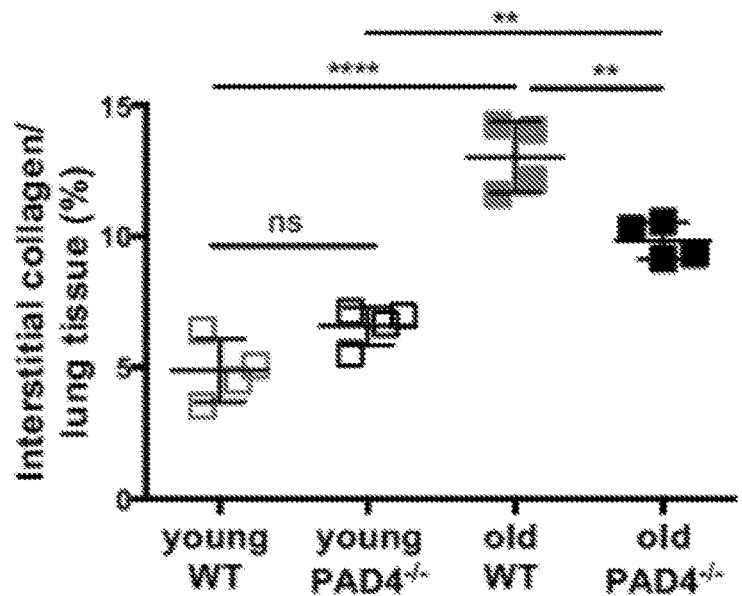
*FIG. 8A*  *FIG. 8B*
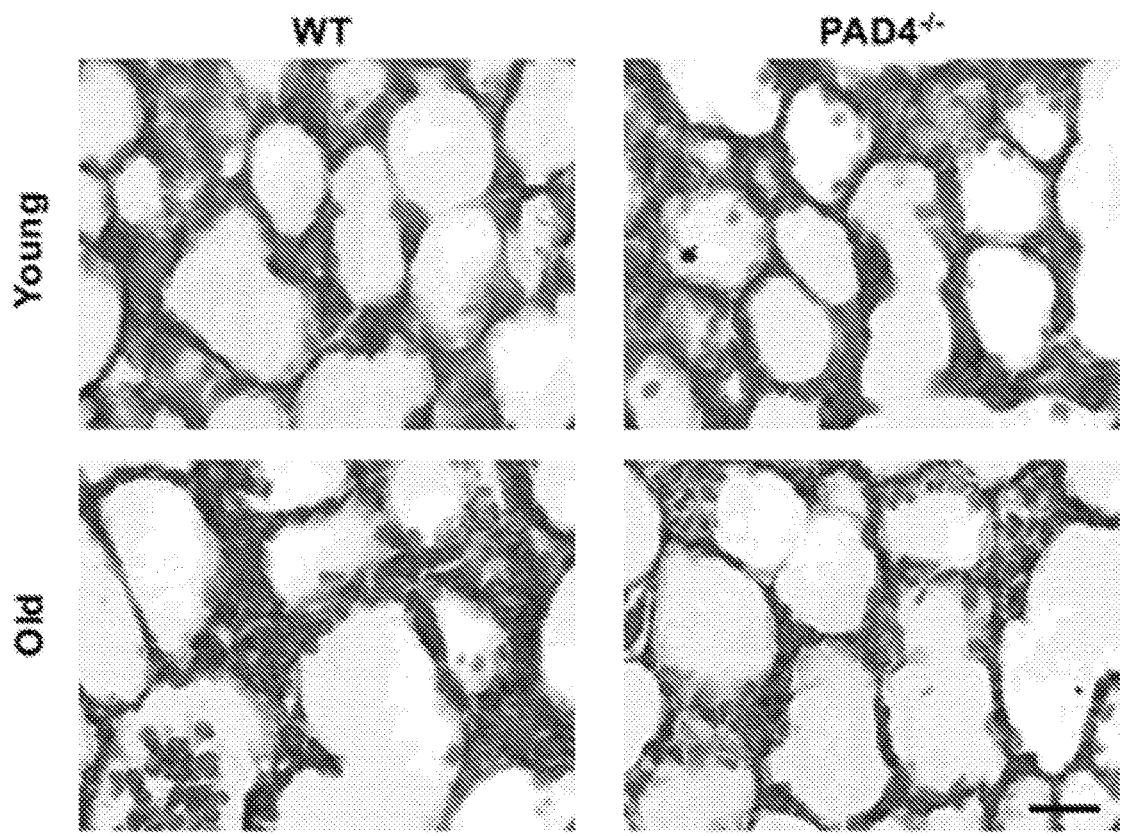
*FIG. 8C*

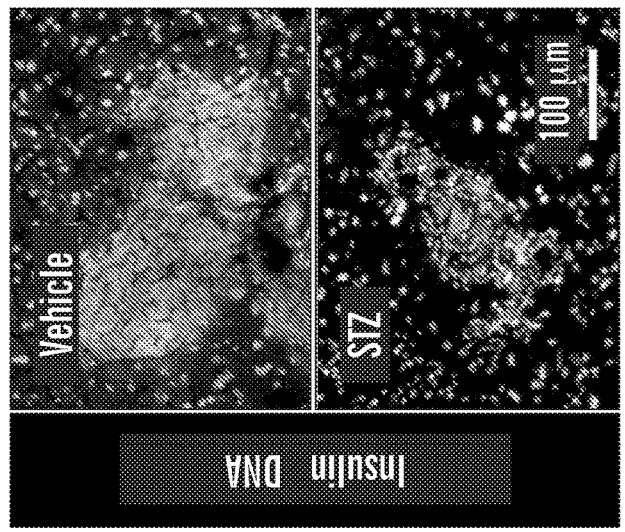
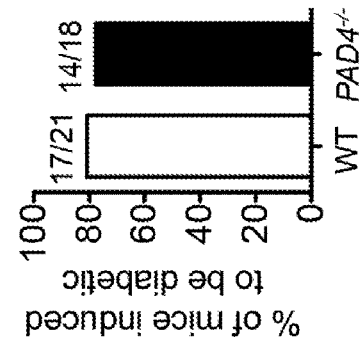
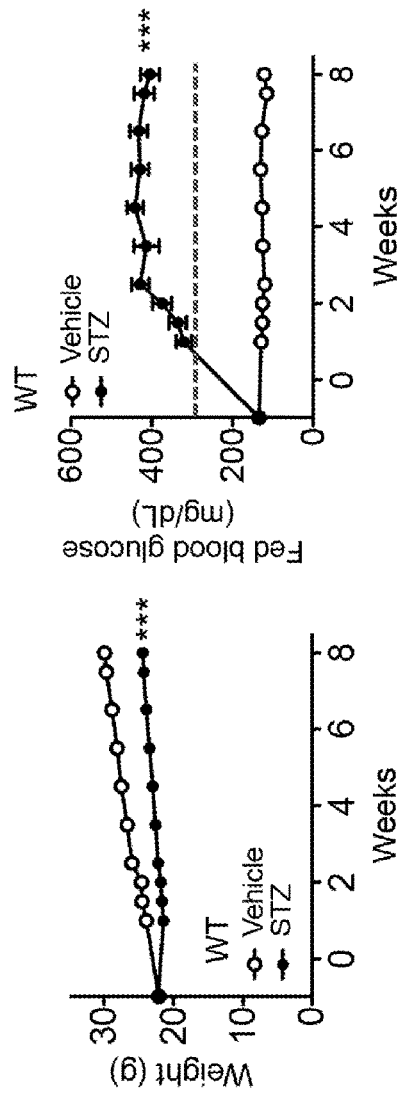
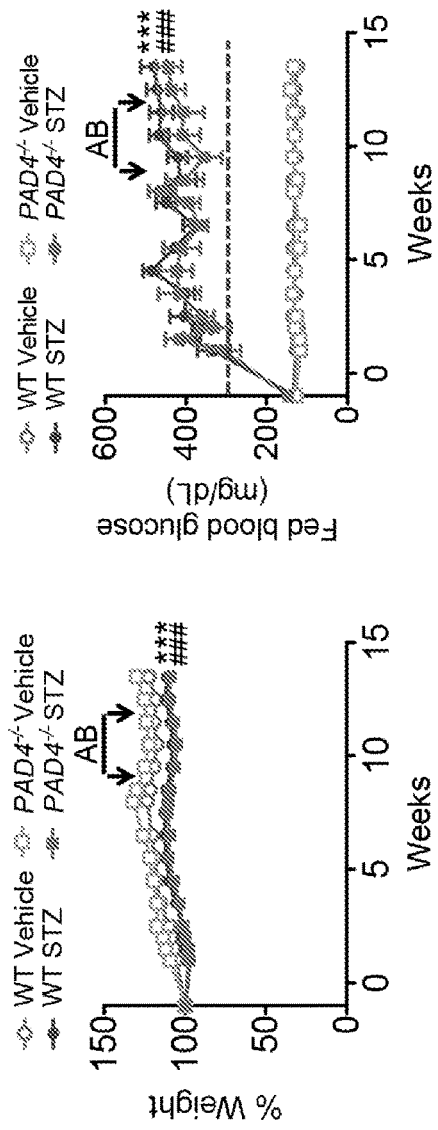
FIG. 9A  FIG. 9B  FIG. 9C
FIG. 9D  FIG. 9E  FIG. 9F Scheme 4. General synthetic scheme of compound 16 [34].

Trabocchi A, Menchi G, Cini N, et al. Click-chemistry-derived triazole ligands of arginine-glycine-aspartate (RGD) integrins with a broad capacity to inhibit adhesion of melanoma cells and both in vitro and in vivo angiogenesis. J Med Chem 2010;53:7119-28.

ANTI-NET COMPOUNDS FOR TREATING AND PREVENTING FIBROSIS AND FOR FACILITATING WOUND HEALING

CROSS-REFERENCE TO RELATED APPLICATIONS

This Application is a 35 U.S.C. § 371 National Phase Entry Application of International Application No. PCT/US2016/013847 filed on Jan. 19, 2016, which claims the benefit under 35 U.S.C. 119(e) of U.S. Provisional Application Ser. No. 62/105,342 filed on Jan. 20, 2015, the contents of which are herein incorporated by reference in their entirety.

FEDERAL FUNDING

This invention was made with federal funding under Grant No: RO1HL102101 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 19, 2016, is named Sequence_Listing.txt and is 8.88 bytes in size.

TECHNICAL FIELD

The technology described herein relates to methods of treating and preventing organ fibrosis due to interstitial collagen deposition and to methods for treatment of wounds, as well as methods for treatment of NET associated complications in diabetes.

BACKGROUND

Fibrosis is the formation of excess extracellular matrix components such as collagen in an organ or tissue. In this process functional parenchymal organ tissue is replaced by fibrotic tissue, which can severely diminish organ function. Fibrosis is typically a result of chronic inflammation induced by a variety of stimuli including persistent infections, autoimmune reactions, allergic responses, chemical insults, radiation and tissue injuries.

In spite of the well-known connection between fibrosis and inflammation, the role of neutrophilic granulocytes in fibrosis in general and in age-related organ fibrosis in particular has remained elusive. Neutrophils constitute the "first line of defense" in inflammatory processes, migrating to the site of injury within minutes after insult. Neutrophils possess a large repertoire of defense mechanisms to combat pathogens, including phagocytosis and the release of bactericidal proteins such as myeloperoxidase (Mayadas et al. (2014) *Annu Rev Pathol* 9:181-218). In response to activating signals, neutrophils in vitro and in vivo efficiently form NADPH oxidase complexes which lead to the production of cell permeable reactive oxygen species (ROS) (Clark R A (1999) *J Infect Dis* 179 Suppl 2:S309-317).

Several years ago, a new defense mechanism of neutrophils, a process termed NETosis, was discovered. Here, neutrophils release their chromatin as neutrophil extracellular traps (NETs) covered with antimicrobial peptides to trap and kill pathogens (Brinkmann V, et al. (2004) *Science* 303(5663):1532-1535). This mechanism critically depends on the enzyme peptidylarginine deiminase 4 (PAD4), which citrullinates specific arginine residues on histone tails, resulting in the decondensation of chromatin which occurs prior to the release of NETs (Wang Y, et al. (2009) *J Cell Biol* 184(2):205-213). Unfortunately, NETosis also occurs under non-infectious conditions such as hypoxia (De Meyer S F et al. (2012) *Arterioscl Thromb Vasc Biol* 32(8):1884-1891) or sterile inflammation as in autoimmune diseases (Kolaczkowska E & Kubes P (2013) *Nat Rev Immunol* 13(3): 159-175). NETs are injurious to the endothelium and underlying tissue as histones are strongly cytotoxic and pro-inflammatory, promoting neutrophil migration and, at high concentrations, even host death (Xu J, et al. (2009) Extracellular Histones Are Major Mediators of Death in Sepsis. *Nat Med* 15(11):1318-1321).

In addition, PAD4$^{-/-}$ mice show decreased neutrophil infiltration into the heart tissue in a model of myocardial ischemia/reperfusion injury (MI/R) (Savchenko A S, et al. (2014) *Blood* 123(1):141-148), providing additional evidence for the pro-inflammatory role of NETs. NET release can also be triggered under many pathological conditions, such as deep vein thrombosis (DVT) (Brill A, et al. (2012) *J Thromb Haemost* 10(1):136-144; Martinod K, et al. (2013) *Proc Natl Acad Sci USA* 110(21):8674-8679; and Fuchs T A, et al. (2010) *Proc Natl Acad Sci USA* 107(36):15880-15885), transfusion-related acute lung injury (Thomas G M, et al. (2012) *Blood* 119(26):6335-6343, MI/R (Savchenko A S, supra.) and cancer (Demers M, et al. (2012) *Proc Natl Acad Sci USA* 109(32):13076-13081; Cools-Lartigue J, et al. (2013) Neutrophil Extracellular Traps Sequester Circulating Tumor Cells and Promote Metastasis. *J Clin Invest.*).

Organ fibrosis is a pathological condition associated with chronic inflammatory diseases and aging. In fibrosis, excessive deposition of extracellular matrix (ECM) severely impairs tissue architecture and function, eventually resulting in organ failure. It has been determined that the process is mediated primarily by the induction of myofibroblasts, which produce large amounts of collagen I, the main component of the ECM (Satoshi Uehal et al., (2012) *Front. Immunol.*, 3:(71)1-6). Accordingly, the origin, developmental pathways, and mechanisms of myofibroblast regulation have attracted attention as potential therapeutic targets, but other pathways may be involved. Gaining an understanding of the mechanisms behind organ fibrosis can provide new targets for the treatment for the devastating affects it has on organ function.

SUMMARY

Herein, we evaluated whether NETosis, which is regulated by ROS prominent in aging (Tabas I & Glass C K (2013) *Science* 339(6116):166-172; and Akong-Moore K, et al. prominent aging (2012) *PloS One* 7(8):e42984), is linked to fibrosis. Embodiments of the invention are based in part on the discovery that peptidylarginine deiminase 4 (PAD4), a key enzyme needed for the formation of NETS, promotes age related organ fibrosis. In particular, we investigated the role of NETs in age-related organ fibrosis and heart dysfunction. We show that neutrophil counts increase in old mice and that these neutrophils are more susceptible to form NETs than neutrophils from young mice. We studied organs of young and old wild-type (WT) and peptidylarginine deiminase 4 (PAD4)-deficient mice that are defective in NETosis. Indeed, PAD4$^{-/-}$ mice were protected from age-related decline in systolic and diastolic heart function as determined by echocardiography. We evaluated left ventricular interstitial fibrosis in both genotypes and found an age-related increase of interstitial collagen only in the hearts of WT mice. The level of fibrosis correlated with the degree of systolic heart dysfunction. A partial protection from fibrosis was found in the lungs of old PAD4$^{-/-}$ mice compared to old WT mice. Accordingly, there is a general role for PAD4/NETs in the etiology of organ fibrosis, thus PAD4/NETs are a novel target for treatment of organ fibrosis.

In one aspect of the invention, provided herein are methods for treating or preventing organ fibrosis. The method comprises administering to a subject in need of treatment, a therapeutically effective amount of at least one anti-NET compound.

In certain embodiments, the subject is diagnosed as having age-related organ fibrosis, or with an organ fibrosis selected from the group consisting of; heart fibrosis, lung fibrosis, liver fibrosis, kidney fibrosis, skin fibrosis, soft tissue fibrosis, and intestine fibrosis.

In certain embodiments, the anti-NET compound is selected from the group consisting of: DNase; a histone-degrading enzyme; an inhibitor of chromatin decondensation; an antibody against a component of a NET; a protease inhibitor, an elastase inhibitor; and a PAD4 inhibitor. In certain embodiments, the PAD4 inhibitor is selected from the group consisting of: Cl-amidine and F-amidine. In certain embodiments, the inhibitors are selective PAD4 inhibitors that are reversible, e.g. including but not limited to GSK484 and GSK199 (Nat. Chem. Biology, in Press).

In certain embodiments, the PAD4 inhibitor is a tetrazole analog, e.g. as described in Subramanian et al., Design, synthesis and biological evaluation of tetrazole analogs of Cl-amidine as protein arginine deiminase inhibitors J. Med. Chem., DOI: 10.1021/jm501636x Publication Date (Web): Jan. 5, 2015.

In one embodiment the tetrazole analog is biphenyl tetrazole tert-butyl Cl-amidine (BTT-Cl-amidine) that exhibits enhanced cell killing in a PAD4 expressing cells also blocks the formation of neutrophil extracellular traps (Subramanian et al., Supra).

In certain embodiments, the PAD4 inhibitor is a peptidomimetic compound, e.g. including but not limited to 1,2,3-triazole peptidomimetic based derivatives incorporating beta-phenylalanine and guanidine scaffolds, e.g. as described in Trabocchi et al. Peptidomimetics as protein arginine deiminase 4 (PAD4) inhibitors, *J. Enzyme Inhib. Med. Chem., early online* 1-6 (2014): DOI:10.3109/147563662014947976. See also FIG. 13 that illustrates chemistry for 16 peptidomimetic PAD4 inhibitors as described in Trabocchi et al. Supra, e.g. 1,2,3-triazole peptidomimetic based derivatives.

In certain embodiments, the anti-NET compound is an inhibitor of NET release from cells, e.g. Cl-amidine blocks NET release from NZM neutrophils in vitro, other inhibitors of NET release are known to those of skill in the art.

In certain embodiments, the PAD4 inhibitor is BB-Cl-amidine (Knight et al. Peptidylarginine deiminase inhibition disrupts NET formation and protects against kidney, skin and vascular disease in lupus-prone MRL/lpr mice *Ann Rheum Dis* doi:10.1136/annrheumdis-2014-205365, online August 2014).

In certain embodiments, the PAD4 inhibitor is YW3-56, as described in Wang et al., (2012) *J. Biol. Chem* 287(31): 25941-53.

In certain embodiments, the therapeutically effective amount of anti-NET compound is administered prophylactically to the subject, e.g. repeated administration for prevention of fibrosis. In certain embodiments, the subject's age is selected from the group consisting of: over 40 years of age, over 30 years of age, over 50 years of age, over 60 years of age, and over 70 years of age, and e.g. prophylactic administration prevents the progression or onset of fibrosis in aging adults.

In certain embodiments, the subject is diagnosed with a disease selected from the group consisting of: heart disease, lung disease, kidney disease, liver disease, and diabetes, and e.g. prophylactic administration thereby prevents the progression or onset of fibrosis in patients having the disease. In certain embodiments, the lung disease is not cystic fibrosis. In certain embodiments, the anti-NET compound is not a PAD4 inhibitor and is selected from the group consisting of a DNase; a histone-degrading enzyme; an inhibitor of chromatin decondensation; an antibody against a component of a NET; a protease inhibitor, and an elastase inhibitor.

In one embodiment, the anti-NET compound is administered locally to one or more target sites in the organ with fibrosis or susceptible to fibrosis, e.g. by injection, or by topical application.

In certain embodiments, the subject with fibrosis does not have cystic fibrosis.

Herein we have also determined that neutrophils isolated from type 1 and type 2 diabetic patients and mice were primed to NETosis. Expression of peptidylarginine deiminase 4 (PAD4), an enzyme important in chromatin decondensation, was 4-fold elevated in neutrophils of diabetics. When subjected to excisional skin wounds, wild-type (WT) mice produced large quantities of NETs at the wound site, but this did not happen in PAD4$^{-/-}$ mice. Higher levels of NET biomarkers were found in the wounds of diabetic mice, accompanied by a significant delay in healing. Impressively, PAD4$^{-/-}$ mice healed faster than WT mice, and their wound healing was not compromised by diabetes. DNase 1, which disrupts NETs, accelerated wound healing in WT mice. We conclude that NETs impair wound healing, especially in diabetes where neutrophils are more susceptible to NETosis. Thus, inhibiting NETosis or cleaving NETs is a therapeutic strategy to improve wound healing and reduce NET-driven chronic inflammation in diabetes.

Accordingly, in another aspect of the invention, methods for facilitating wound healing are provided. The methods comprise administering a therapeutically effective amount of at least one anti-NET compound. In certain embodiments, the anti-NET compound used to facilitate wound healing is not a DNase.

In certain embodiments the subject to be treated with an anti-NET compound in order to facilitate wound healing is diagnosed as having diabetes.

In yet another aspect of the invention, methods for treating NET associated complications in diabetes are provided. The methods comprise administering a therapeutically effective amount of at least one anti-NET compound. In certain embodiments, the inflammation associated with diabetes is decreased by at least 10%, at least 20%, at least 30%, or at least 50%. In certain embodiments, wound healing facilitated by at least 10%, at least 20%, at least 30%, or at least 50%.

In certain embodiments, in each of the above aspects, the anti-NET compound is selected from the group consisting of: DNase; a histone-degrading enzyme; an inhibitor of chromatin decondensation; an antibody against a component of a NET; a protease inhibitor, an elastase inhibitor; and a PAD4 inhibitor.

In certain embodiments, in each of the above aspects, the PAD4 inhibitor is selected from the group consisting of: Cl-amidine and F-amidine. In certain embodiments, the inhibitors are selective PAD4 inhibitors that are reversible, e.g. including but not limited to GSK484 and GSK199 (Nat. Chem. Biology, in Press).

In certain embodiments, in each of the above aspects, the PAD4 inhibitor is a peptidomimetic compound, e.g. including but not limited to 1,2,3-triazole peptidomimetic based derivatives incorporating beta-phenylalanine and guanidine scaffolds, e.g. as described in Trabocchi et al. Peptidomimetics as protein arginine deiminase 4 (PAD4) inhibitors, *J. Enzyme Inhib. Med. Chem.*, early online 1-6 (2014): DOI: 10.3109/147563662014947976. See also FIG. 13 that illustrates chemistry for 16 peptidomimetic PAD4 inhibitors as described in Trabocchi et al. Supra, e.g. 1,2,3-triazole peptidomimetic based derivatives.

In certain embodiments, in each of the above aspects, the PAD4 inhibitor is a tetrazole analog, e.g. as described in Subramanian et al., Design, synthesis and biological evaluation of tetrazole analogs of Cl-amidine as protein arginine deiminase inhibitors J. Med. Chem., DOI: 10.1021/jm501636x Publication Date (Web): Jan. 5, 2015.

In one embodiment, in each of the above aspects, the tetrazole analog is biphenyl tetrazole tert-butyl Cl-amidine (BTT-Cl-amidine) that exhibits enhanced cell killing in a PAD4 expressing cells also blocks the formation of neutrophil extracellular traps (Subramanian et al., Supra).

In certain embodiments, in each of the above aspects, the PAD4 inhibitor is YW3-56, as described in Wang et al., (2012) *J. Biol. Chem* 287(31):25941-53.

In certain embodiments, in each of the above aspects, the PAD4 inhibitor is a peptidomimetic compound, e.g. including but not limited to 1,2,3-triazole peptidomimetic based derivatives incorporating beta-phenylalanine and guanidine scaffolds, e.g. as described in Trabocchi et al. Peptidomimetics as protein arginine deiminase 4 (PAD4) inhibitors, *J. Enzyme Inhib. Med. Chem.*, early online 1-6 (2014): DOI: 10.3109/147563662014947976. See also FIG. 13 that illustrates chemistry for 16 peptidomimetic PAD4 inhibitors as described in Trabocchi et al. Supra, e.g. 1,2,3-triazole peptidomimetic based derivatives.

In certain embodiments, in each of the above aspects, the anti-NET compound is an inhibitor of NET release from cells, e.g. Cl-amidine blocks NET release from NZM neutrophils in vitro, other inhibitors of NET release are known to those of skill in the art.

In certain embodiments in each of the above aspects of the invention the anti-NET compound administered is not a DNase.

In certain embodiments in each of the above aspects of the invention the anti-NET compound is not an elastase inhibitor.

In certain embodiments in each of the above aspects of the invention more than one anti-NET compound is administered, e.g. a PAD4 inhibitor and a DNase, or aPAD4 inhibitor and an elastase inhibitor.

In certain embodiments in each of the above aspects of the invention the therapeutically effective amount of anti-NET compound is administered prophylactically.

In certain embodiments in each of the above aspects of the invention the therapeutically effective amount of anti-NET compound is given as a single dose of administration. In certain embodiments, the dose is given repeatedly.

In certain embodiments in each of the above aspects of the invention the composition comprising at least one anti-NET compound further comprises a pharmaceutically acceptable carrier. In further embodiments, the composition comprising at least one anti-NET compound further comprises another compound that is useful in treating or preventing the condition to be treated, e.g. wounds, fibrosis or NET driven inflammation and delayed wound healing in diabetes.

The details of various embodiments of the invention are set forth in the description below. Other features, objects, and advantages of the invention will be apparent from the description and the drawings, and from the claims. All references cited herein, in this specification, are herein incorporated by reference in their entirety for purposes of disclosure.

DESCRIPTION OF THE DRAWINGS

FIGS. 1a to 1k indicate that diabetes or high glucose concentration in vitro primes human and murine neutrophils to undergo NETosis. FIG. 1a-FIG. 1c are graphs of HbA1c in Healthy subjects (black) and patients with diabetes mellitus (DM) (pink, type 1 DM; purple, type 2 DM) who were recruited and peripheral neutrophils were isolated from fresh whole blood. (FIG. 1a) All diabetic patients had HbA1c>6.5%. FIG. 1b is a graph indicating that more neutrophils isolated from diabetic patients formed NETs in vitro when stimulated with ionomycin (4 μM), and FIG. 1c is a graph indicating these neutrophils expressed more PAD4 when compared to those from healthy subjects as reflected by Western blotting, inlay; diabetic first lane is type 1 diabetes, lane 2 and lane 3 type II diabetes. FIG. 1d is a graph indicting that more high glucose (HG)-treated neutrophils from healthy subjects produced NETs with or without stimulation than those in normal glucose (NG) or mannitol (M). n=5 per condition. FIG. 1e-FIG. 1i are graphs. Neutrophils were isolated from streptozotocin (STZ)-induced diabetic mice (FIG. 1e-FIG. 1g) or db/db diabetic mice (FIG. 1h-FIG. 1i) and stimulated with LPS from *Klebsiella pneumoniae* at indicated concentrations for 2.5 h. More neutrophils from STZ-induced diabetic mice or db/db mice were H3Cit$^{high}$ (FIG. 1e, FIG. 1h) and formed NETs (FIG. 1f, FIG. 1i), when compared to normoglycemic vehicle-treated control (FIG. 1e, FIG. 1f) or m+/db mice (FIG. 1h, FIG. 1i). US, unstimulated. n=12 for Vehicle, n=10 for STZ; n=6-7 for m+/db; n=7-8 for db/db. FIG. 1g are representative images of isolated neutrophils from vehicle- or STZ-treated mice, as labeled. Neutrophils were exposed to LPS (25 μg/mL) for 2.5 h. Arrows indicate NETs. Scale, 50 μm. FIG. 1j and FIG. 1k are graphs illustrating more neutrophils isolated from normoglycemic wild-type mice and exposed to high glucose in vitro were (FIG. 1j) H3Cit$^{high}$ and (FIG. 1k) produced NETs. n=10 per medium condition. *$P<0.05$, $P<0.01$, *$P<0.001$. (FIG. 1a-FIG. 1c, FIG. 1h, FIG. 1i) Mann-Whitney test; (FIG. 1d, FIG. 1j, FIG. 1k) repeated measures ANOVA followed by Bonferroni's post test; (FIG. 1e, FIG. if) Student's t test FIG. 2a is a Western blots showing the time course of H3Cit appearance after skin injury. Wounds were generated with biopsy punches at the dorsal skin of the mice. Scab and the surrounding 0.5 mm skin were collected at the time indicated. H3Cit was detectable starting day 1 post wounding and peaked from day 3 to 7. H3Cit was absent in the control unwounded skin (Ctrl). H3, histone H3. **$P<0.01$ versus Ctrl, Student's t test, n=3-5. Immunofluorescence images of a 3-day wound bed immediately beneath scab showed cells were mostly positive for Ly6G and H3Cit (data not shown). Representative images of a 3-day wound using confocal microscopy showed H3Cit co-localized with extracellular DNA in the Ly6G (red)-positive area in the scab (data not shown). FIG. 2b are Western blots of 3-day wounds collected from mice with defective leukocyte recruitment ($CD18^{-/-}$, left) and mice depleted of neutrophils using an anti-Ly6G antibody (right, representative of n=7). H3Cit was markedly reduced in these wounds. IgG, IgG isotype control for the anti-Ly6G antibody.

FIG. 3a is a representative Western blot of wounds from WT (+/+) and $PAD4^{-/-}$ (−/−) mice. H3Cit was absent in the wounds from $PAD4^{-/-}$ mice. Ly6G levels in wounds were similar in both genotypes (See also FIG. 12a, FIG. 12b). FIG. 3b is a panel of photographs of wounds of WT and $PAD4^{-/-}$ mice. Wounds of $PAD4^{-/-}$ healed faster and both healed without apparent signs of infection. Scale, 5 mm. FIG. 3c is a graph indicating changes in wound area compared to day 0. Wound area reduced faster in $PAD4^{-/-}$ mice starting day 1 post wounding. *P<0.05, P<0.01, *P<0.001 versus WT, Student's t test, n=9-16. FIG. 3d is a graph indicating significantly more $PAD4^{-/-}$ mice had wounds completely closed by day 14. P<0.01, two-tailed Fisher's exact test. FIG. 3e is a graph of re-epithelialization determined from H&E staining on 3-day wounds from WT and $PAD4^{-/-}$ mice (data not shown), re-epithelialization occurred faster in $PAD4^{-/-}$ mice. *P<0.001, Student's t test, n=6-9. Images of H&E staining and confocal microscopy of 3-day wounds from WT and $PAD4^{-/-}$ mice. H&E revealed the presence of extracellular DNA in the scab of WT mice, while neutrophils appeared intact (ring-shaped,) in $PAD4^{-/-}$ scabs (data not shown). Confocal immunofluorescence images (lower panels) showed intact neutrophil morphology and an absence of H3Cit in the scabs of $PAD4^{-/-}$ mice compared to the NETs in the scabs of WT mice (data not shown)

FIGS. 4a to 4i are graphs and Western blots indicating that PAD4 deficiency or DNase 1 treatment enhances wound healing in diabetic mice. WT and $PAD4^{-/-}$ mice were treated with vehicle or STZ. Wounding was performed 8 weeks after diabetic induction. All mice were provided with antibiotics (2.5% Sulfatrim) in the drinking water immediately after wounding. (FIG. 4a-FIG. 4h). FIG. 4a to FIG. 4c are graphs showing wound area reduction. FIG. 4d to FIG. 4f are graphs indicating percent mice with open wounds per time (FIG. 4a-FIG. 4h). Data from all groups were obtained simultaneously in multiple experiments but split into three graphs (FIG. 4a-FIG. 4c and FIG. 4d-FIG. 4f) to facilitate comparison. *P<0.05, P<0.01, *P<0.001 between groups on respective post-wounding day (FIG. 4a-FIG. 4c, Student's t test) or between curves (FIG. 4d-FIG. 4f, log-rank test), n=6-9. (FIG. 4a) Wound healing was impaired in STZ-induced diabetic WT mice compared to normoglycemic mice (vehicle). (FIG. 4b) $PAD4^{-/-}$ mice had much faster wound repair than WT under diabetic conditions. (FIG. 4c) Diabetes did not impair wound repair in $PAD4^{-/-}$ mice. (FIG. 4d) STZ-induced diabetic WT mice had delayed wound closure compared to normoglycemic mice (vehicle). (FIG. 4e) STZ-treated $PAD4^{-/-}$ mice achieved total wound closure earlier than STZ-treated WT mice. (FIG. 4f) Wound closure was not significantly different (NS) between normoglycemic (vehicle) and diabetic (STZ) $PAD4^{-/-}$ mice. FIG. 4g is a representative Western blot and summarized data (normalized to mean of vehicle) showing higher H3Cit levels in wounds from STZ-induced diabetic mice one day post wounding. (FIG. 4h, FIG. 4i) DNase 1 (dornase alfa) treatment facilitated wound area reduction (upper panels) and re-epithelialization (lower panels) in both (FIG. 4h) diabetic and (FIG. 4i) normoglycemic WT mice. (FIG. 4h) DNase 1 treatment did not provide additional benefits in wound healing in diabetic $PAD4^{-/-}$ mice. (FIG. 4h) *P<0.05, ***P<0.001 and NS non-significant using Kruskal-Wallis test followed by Dunn's post test, #P<0.05, ##P<0.01 using Mann-Whitney test, n=5-9. (FIG. 4i) *P<0.05, Student's t-test, n=9-10

FIGS. 5A to 5E are graphs showing that neutrophil and platelet count is increased in aging WT mice and so is neutrophil susceptibility to produce NETs: FIG. 5A is a graph of neutrophil counts in peripheral blood of young (8 weeks) vs. old (24 months) WT mice. n=6-8. FIG. 5B is a graph of platelet counts in young (8 weeks) vs. old (24 months) WT mice. n=6-8. FIG. 5C is a graph of quantification of the percent of H3Cit-positive neutrophils by thresholding analysis of immunostained cytospins of red blood cell-depleted blood cells. n=6-8. FIG. 5D is a graph of quantification of Ly6G-positive neutrophils in the total leukocyte cytospin population. n=6-8. In C and D, young mice were 6-8 weeks and old mice were 15-20 months old. FIG. 5E is a graph of the percentage of NET-forming peripheral blood neutrophils after incubation with vehicle (unstimulated, US), 4 µM ionomycin (iono), or 100 nM phorbol 12-myristate 13-acetate (PMA) for 3.5 h. Neutrophils from old (24-27 months) mice formed significantly more NETs under all conditions than neutrophils from young (2-5 months) mice. n=5. *P<0.05, P<0.01, *P<0.001.

FIG. 6A is 4 graphs of left ventricular ejection fraction (LVEF) as a measure of systolic function and cardiac dimensions (IVS;d, LVPW;d and LVID;d) of WT and $PAD4^{-/-}$ retired breeders (1217 months) were measured by transthoracic echocardiography. WT retired breeders showed a significantly reduced LVEF compared to $PAD4^{-/-}$ retired breeders. Cardiac dimensions were not significantly different between WT and $PAD4^{-/-}$ retired breeders. n=7-11. FIG. 6B is 4 graphs, the same echocardiographic measurements of LVEF and cardiac dimensions were repeated in a group of young (6-8 weeks) and old (14-18 months) WT and $PAD4^{-/-}$ mice that had been kept on standard lab diet. Measurements showed similar results as in the retired breeders with a significant difference between the LVEF of old WT and old $PAD4^{-/-}$ mice (left panel). LVEFs of old $PAD4^{-/-}$ mice were comparable to young $PAD4^{-/-}$ mice. Old WT and $PAD4^{-/-}$ had similar cardiac dimensions. n=4-7. FIG. 6C are representative ultrasound M-mode images of the left ventricle showed better contractility in the $PAD4^{-/-}$ mice compared to the old WT mice. S, systole; D, diastole. FIG. 6D is a graph of ventricular diastolic dysfunction was evaluated in young WT and $PAD4^{-/-}$ (6-8 weeks) mice as well as old WT and $PAD4^{-/-}$ mice (15-20 months). The flow pattern across the mitral valve was assessed using Pulsed Wave Doppler mode and ventricular filling pattern was calculated as the ratio between the E and A wave. Only the old WT mice showed evidence of impaired ventricular relaxation with an average E/A ratio below 1. n=4-6. FIG. 6E is characteristic images of Pulsed Wave Doppler measurements of the E and A wave showed a normal E'A pattern (E>A) in the old $PAD4^{-/-}$ mice and a reversed pattern (E<A) in the old WT mice, leading to a ratio of under 1. *P<0.05, P<0.01, *P<0.001.

FIGS. 7A to 7D are graphs and images indicating that PAD4-deficiency reduced age-related cardiac fibrosis: FIG. 7A is a graph of interstitial collagen, Cardiac interstitial fibrosis was assessed by Sirius Red staining for collagen fibers in sections of the left ventricle of the heart of WT and PAD4$^{-/-}$ retired breeders (1217 months). The percentage of fibrotic area in the heart tissue was quantified by ImageJ shown in FIG. 7C, excluding perivascular fibrosis. In PAD4$^{-/-}$ retired breeders, there was significantly less interstitial fibrosis than in WT retired breeders. n=6. FIG. 7B is a graph showing interstitial collagen. The same analysis was performed for young (6-8 weeks) WT and young PAD4$^{-/-}$ mice as well as for old (14-18 months) WT and old PAD4$^{-/-}$ mice on standard diet. Quantification of Sirius red staining again showed less fibrosis in the old PAD4 mice compared to the old WT mice. In old PAD4$^{-/-}$ mice, the percentage of interstitial collagen remained comparable to young PAD4$^{-/-}$ mice. n=7-8. FIG. 7C are images, Sirius red staining of cardiac tissue showed more fibrotic strands in the myocardium of WT retired breeders compared to the PAD4$^{-/-}$ retired breeders. Composite images of the left ventricle were generated using the ImageJ MosaicJ software; representative mosaics are presented. Scale bar=100 µm. Arrowheads indicate stained collagen strands. FIG. 7D are images, the increase in myocardial interstitial collagen fibers in WT retired breeders compared to PAD4$^{-/-}$ retired breeders was more clearly visible at higher magnification in the Sirius red staining (left) and in Masson's trichrome stain for collagen (right, collagen fibers are blue (see arrows)). Scale bar=100 µm. Arrowheads point to collagen fibers. *P<0.05, **P<0.01

FIGS. 8A to 8C are graphs and images, Old PAD4$^{-/-}$ mice have significantly less collagen staining in their lungs than old WT mice. FIG. 8A is a graph showing the percentage of collagen positive area in lung tissue of WT and PAD4$^{-/-}$ retired breeders (12-17 months) was quantified using Masson's trichrome stain for collagen and subsequently color gating for blue fibers. Retired WT breeders had a significantly higher percentage of collagen in lung tissue than retired PAD4$^{-/-}$ breeders. n=6-7. FIG. 8B is a graph of interstitial collagen/lung tissue %; the same analysis for collagen fibers within the lung tissue was performed for young (6-8 weeks) WT and PAD4$^{-/-}$ mice and old (14-18 months) WT and PAD4$^{-/-}$ mice. While collagen content increased from young mice to old mice in both WT and PAD4$^{-/-}$ mice, this increase was significantly higher in the old WT mice. n=4. FIG. 8C is a panel of representative photographs of lung sections stained with Masson's trichrome stain. Scale bar=20 µm. *P<0.05,  P<0.01, ** P<0.0001.

FIGS. 9a to 9f show graphs and images of the basic parameters of STZ-induced diabetes in WT and PAD4$^{-/-}$ mice. Mice were injected i.p. with vehicle or STZ (50 mg/kg per day) for 5 consecutive days. Body weight and fed blood glucose were examined starting 1 week after completion of injections. FIG. 9a is a graph of weight over time, STZ-treated mice gained less weight compared to the vehicle control. FIG. 9 b is a graph of glucose over time. Diabetes was defined as fed blood glucose >300 mg/dL (indicated by blue dotted line). STZ-treated mice became diabetic the first week after treatment. (FIG. 9a, FIG. 9b) *P<0.001 at all time points starting week 1 between vehicle and STZ, Student's t test, n=15 for Vehicle, n=13 for STZ. FIG. 9c is an image that validates diabetes induction. Representative immunofluorescence images showing a marked reduction of insulin-producing β cells and disrupted islet morphology in the pancreas of STZ-treated mice. FIG. 9d, and FIG. 9e PAD4$^{-/-}$ mice attained body weight (FIG. 9d) and fed blood glucose levels (FIG. 9e) similar to WT after STZ injection. AB indicates the period of antibiotic treatment (after wounding), which did not affect fed blood glucose levels in any group (FIG. 9e). (FIG. 9d, FIG. 9e) *P<0.001 at all time points starting week 1 between WT vehicle and WT STZ, #### P<0.001 at all time points starting week 1 between PAD4$^{-/-}$ vehicle and PAD4$^{-/-}$ STZ, Student's t test, n=7 for WT Vehicle, n=9 for WT STZ, n=5 for PAD4$^{-/-}$ Vehicle, n=6 for PAD4$^{-/-}$ STZ. FIG. 9f is a graph of percent mice induced to be diabetic. Chi-square test indicates no difference between WT and PAD4$^{-/-}$ in diabetes inducibility using STZ. P=1.00

DETAILED DESCRIPTION

Definitions

Figure 1A:
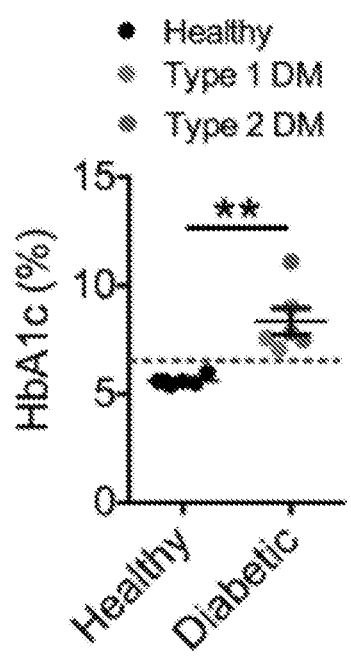

For convenience, the meaning of certain terms and phrases used in the specification, examples, and appended claims, are provided below. If there is an apparent discrepancy between the usage of a term in the art and its definition provided herein, the definition provided within the specification shall prevail.

Definitions of common terms in cell biology and molecular biology can be found in "The Merck Manual of Diagnosis and Therapy", 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are also be found in Benjamin Lewin, Genes IX, published by Jones & Bartlett Publishing, 2007 (ISBN-13: 9780763740634); Kendrew et al. (eds.), Molecular Biology and Biotechnology: a Comprehensive Desk Reference, published by VCH Publishers, Inc., 1995

(ISBN 1-56081-569-8) and Current Protocols in Protein Sciences 2009, Wiley Intersciences, Coligan et al., eds.

Unless otherwise stated, the present invention was performed using standard laboratory techniques found, for example in the Molecular Cloning: A Laboratory Manual, 3rd Ed., Sambrook and Russel, Cold Spring Harbor Laboratory Press, 2001; or e.g. the latest edition of Methods in Enzymology Series. Editor: John Abelson, Melvin Simon, Anna Pyle, Elsevier Science Publishing Inc. New York.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, e.g. in the absence of an agent, for example a decrease by at least about 20%, or at least about 30%, or at least about 40%, or at least about 50%, or at least about 60%, or at least about 70%, or at least about 80%.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, e.g. in the absence of an agent, for example an increase of at least about 20%, or at least about 30%, or at least about 40%, or at least about 50%, or at least about 60%, or at least about 70%, or at least about 80%, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration. In certain embodiments, the anti-NET compound is administered by local administration, e.g. local injection, or other method allowing delivery to a target site within an organ. As used herein, the term "local" means localized to the organ or wound, i.e. not systemic administration.

Some exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, the term "antibody" refers to immunoglobulin molecules and immunologically active portions of immunoglobulin molecules, i.e., molecules that contain an antigen binding site that immunospecifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

As used herein in the context of expression, the terms "treat," "treatment," "treating" and the like, in the context of the present invention insofar as it relates to any of the conditions recited herein (e.g. fibrosis, Diabetes (e.g. NET driven inflammation and delayed wound healing in Diabetes)), mean to relieve, alleviate, ameliorate, inhibit, slow down, reverse, or stop the progression, aggravation, deterioration, progression, anticipated progression or severity of at least one symptom or complication associated with such condition (e.g. fibrosis, Diabetes (e.g. NET driven inflammation and delayed wound healing in Diabetes)). In one embodiment, the symptoms of a condition are alleviated by at least 5%, at least 10%, at least 20%, at least 30%, at least 40%, or at least 50%.

By "lower" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

As used herein, the phrase "therapeutically effective amount" or "effective dose" refers to an amount that provides a therapeutic benefit in the treatment, prevention, or management of a condition caused by NETS (e.g. fibrosis or inhibition of wound healing, or treatment of diabetes), e.g. an amount that provides a statistically significant decrease in at least one symptom of the condition (e.g. collagen deposition or slow wound healing, or inflammation of diabetes). Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "pharmaceutical composition" refers to the active agent in combination with a pharmaceutically acceptable carrier of chemicals and compounds commonly used in the pharmaceutical industry.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

As used herein, a "subject" means a human or animal. In one embodiment, the animal is a vertebrate such as a primate, rodent, domestic animal, avian species, fish or game animal. The terms, "patient", "individual" and "subject" are used interchangeably herein.

Preferably, the subject is a mammal. The mammal can be a human or non-human primate. Mammals other than humans can be advantageously used as subjects that represent animal models of fibrosis, wound healing or diabetic conditions. In addition, the methods described herein can be used to treat domesticated animals and/or pets.

The subject can be one who has been previously diagnosed with an organ fibrosis, or diabetes, or a subject identified as having one or more complications related to an organ fibrosis or diabetes, and optionally, but need not have already undergone treatment for the condition, or the one or more complications related to the condition.

A subject can also be one who is not suffering from the condition, e.g. fibrosis. or diabetes. For example, a subject can be one who exhibits one or more risk factors for fibrosis or diabetes; e.g. having a family history if the disease or being of older age, e.g. a subject over 30 years of age, or over 40 years of age, or over 50 years of age. Accordingly, methods for preventing the formation of organ fibrosis are also provided, the methods comprise treating the subject determined to be at risk for fibrosis, with an anti-NET compound. In certain embodiments, the patient at risk of fibrosis is at least 40 years of age, at least 50 years of age, at least 60 years of age, or at least 70 years of age. In certain embodiments, the patient at risk of fibrosis is a patient that is to be exposed to radiation, e.g. a patient of any age.

NETosis

Embodiments of the technology described herein are based, in part, on the discovery that NETosis in a subject slows the wound healing process and that NETosis is linked with collagen deposition in organ fibrosis. It has also been determined herein that increased NETosis is present in Diabetes.

As used herein, the term "NET" refers to extracellular complexes of nucleosomes and proteins, e.g. proteins having anti-microbial activity. The nucleosomes may be derived from neutrophils, mast cells, eosinophils, monocytes, or leukocytes. "NETosis" refers to the formation of NETS through a unique form of cell death that is characterized by the release of decondensed chromatin and granular contents to the extracellular space.

Herein, we have determined that NETosis is elevated in wounds and in subjects that have diabetes. We have further determined that NETosis is prominent in aging and have found a connection between the prevalence of NETosis and organ fibrosis. In particular, we have determined that peptidylarginine deiminase 4 (PAD4), a key enzyme needed for the formation of NETS, promotes age related organ fibrosis. Thus, methods for treating wounds, diabetes and fibrosis are provided. The methods comprise administrating a therapeutically effective amount of at least one anti-NET compound (e.g. a PAD 4 inhibitor; a DNase, a histone-degrading enzyme; an inhibitor of chromatin decondensation; an antibody against a component of a NET; a protease inhibitor, or an elastase inhibitor, or protease inhibitor) to a subject in need of treatment.

Anti-NET Compounds

Some embodiments are directed to methods for the treatment or prevention of organ fibrosis, or NET associated complications in diabetes (e.g. increased inflammation and delayed wound healing), in a patient with anti-NET compound. Other embodiments are directed to methods for facilitating wound healing in a subject comprising administering an anti-NET compound. In certain embodiments the anti-NET compounds are delivered directly to the wound. As used herein, "anti-NET compounds" can include any compound that degrades or targets for degradation any component of a NET and/or that prevents the formation of NETs (e.g. PAD4 inhibitors). Also included are compounds that otherwise inhibit the activity of a NET component or impair the ability of a cell to form a NET, e.g. inhibition of PAD4, which is required for NET formation. An anti-NET compound can be a nucleic acid (DNA or RNA), small molecule, lipid, carbohydrate, protein, peptide, antibody, or antibody fragment. In some embodiments, an anti-NET compound is an enzyme, e.g. an enzyme which cleaves and/or degrades, e.g. a nucleic acid, protein, polypeptide, or carbohydrate.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

In certain embodiments an anti-NET compound is selected from the group consisting of; DNase, heparin, an antibody (i.e. an antibody to histones or to a particular histone), a histone degrading enzyme (i.e. mast cell proteinase 1 (Gene ID: 1215)), plasmin (Gene ID: 5340), cathepsin D (Gene ID: 1509) or activated protein C (Gene ID:5624)) or an inhibitor of chromatin decondensation (i.e.staurosporine, HDAC inhibitors (i.e. M344), PAD4 inhibitors, protease inhibitors, or elastase inhibitors (i.e. Gelin®)).

In one embodiment, the anti-NET compound is not heparin. In one embodiment, the anti-NET compound is not DNase. In some embodiments, the anti-NET compound is selected from the group consisting of; a histone-degrading enzyme; an inhibitor of chromatin decondensation; an antibody against a component of a NET; a protease inhibitor, an elastase inhibitor; or a PAD4 inhibitor.

Anti-NET compounds can be produced recombinantly using methods well known to those of skill in the art (See Sambrook et al., Molecular Cloning: A Laboratory Manual (2 ed.), Cold Spring Harbor Laboratory Press, Cold Spring Harbor, N.Y., USA (1989)). Alternatively, anti-NET compounds are available commercially e.g. Pulmozyme® (Genentech; San Francisco, Calif.), DNase (#D5319 Sigma-Aldrich; St. Louis, Mo.)(#90083 Thermo Scientific; Rockford, Ill.), RNAse (#R4642 Sigma-Aldrich; St. Louis, Mo.), Heparin® (Celsus; Cincinatti, Ohio), anti-histone antibodies (ab1791, ab8580, ab8898, ab6002, ab1790, ab9053, ab10158, ab71594, ab4269 Abcam; Cambridge, Mass.), mast cell proteinase 1 (5146-SE-010 R&D Systems; Minneapolis, Minn.), thrombin (HCT-0020 Haematologic Technologies; Essex Junction, Vt.), plasmin (HCPM-0140 Haematologic Technologies; Essex Junction, Vt.), cathepsin D (1014-AS-010 R&D Systems; Minneapolis, Minn.), activated protein C (AEZ004B Aniara; Mason, Ohio), staurosporine (S4400 Sigma-Aldrich; St. Louis, Mo.), M344 (M5820 Sigma-Aldrich; St. Louis, Mo.) or Gelin® (G0528 Sigma-Aldrich; St. Louis, Mo.).

In certain embodiments, the anti-NET compound is a monoclonal antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference).

In some embodiments, the anti-NET agent is a PAD4 inhibitor. As used herein, "PAD4" refers to peptidylarginine deiminase 4, an enzyme that converts protein arginine residues to citrulline through a deimination reaction (e.g. SEQ ID NO: 01 (mRNA) and SEQ ID NO: 02 (protein)).

In certain embodiments, the anti-NET agent is a general PAD inhibitor, i.e. is an inhibitor that inhibits more than one type of PAD enzyme, e.g. PAD 1, and/or PAD2, and/or PAD3 or, and/or PAD4. See e.g. Wang et al., Anticancer peptidylarginine deiminase (PAD) inhibitors regulate the autophagy flux and the mammalian target of rapamycin complex 1 activity *J Biol Chem.* 2012 Jul. 27; 287(31): 25941-53; e.g. YW3-56. See also PCT Publication WO/2014/188193 entitled 'peptidylarginine deiminases (pad) inhibitors."

PAD4 is distinguished from other PAD family enzymes by having a nuclear localization signal and thus being able to enter the nucleus and citrullinate histones. As described herein, a loss of PAD4 activity results in decreased NET formation and decreased DVT in mice. A PAD4 inhibitor can decrease the expression or activity of PAD4.

Inhibition of PAD4 can be monitored by measuring PAD4 activity. A non-limiting example of an assay of PAD4 activity is as follows: a candidate inhibitor, in a reaction buffer comprising 100 mM HEPES (pH 7.6), 50 mM NaCl, and 0.5 mM tris(2-carboxyethyl)phosphine (TCEP) can be preincubated with PAD4 (0.2 μM) (in the presence or absence of 10 mM CaCl2) at 37° C. for 15 min prior to the addition of the substrate, N-α-benzoyl-L-arginine ethyl ester (BAEE) (10 mM final concentration) (and 10 mM CaCl2 if CaCl2 was absent in the pre-incubation) to initiate the reaction. After 15 min the reactions can be quenched by flash freezing in liquid nitrogen. For color development, 200 μL of freshly prepared COLDER solution (2.25 M $H_3PO_4$, 4.5 M $H_2SO_4$, 1.5 mM $NH_4Fe(SO_4)$, 20 mM diacetyl monoxime, and 1.5 mM thiosemicarbazide) can be added to each of the quenched reactions, vortexed to ensure complete mixing, and then incubated at 95° C. for 30 minutes. The absorbance at 540 nm can then measured and compared to a citrulline standard curve to determine the concentration of citrulline produced during the course of the reactions (PAD4 deiminates the BAEE substrate). IC50 values can be determined by fitting the concentration-response data to Eq. (1)

Fractional activity of PAD4=1/(1+([candidate inhibitor]/IC50)) (Eq. 1)

The concentration of an inhibitor that corresponds to the midpoint (fractional activity=0.5) can be referred to as the IC50. Kits for measuring PAD4 activity are also commercially available, e.g. Cat No. 7000560, Cayman Chemical; Ann Arbor, Mich.

Any inhibitors of PAD4 can be used in the methods described herein. For example, in some embodiments, a PAD4 inhibitor can be a small molecule inhibitor. Small molecule inhibitors of PAD4 are known in the art (see, for example, Luo et al. Biochemistry 2006; U.S. Pat. No. 7,964,636; and U.S. Patent Publications 2007/0276040 and 2011/0142868; each of which is incorporated by reference herein in its entirety) and include, by way of non-limiting example, Cl-amidine and F-amidine. In some embodiments, the PAD4 inhibitor can be specific for PAD4. In some embodiments, the PAD4 inhibitor can be a PAD family inhibitor. PAD4 inhibitors are commercially available, e.g. Cl-amidine (Catalog number 10599, CAS 913723-61-2, Cayman Chemical; Ann Arbor, Mich.) and F-amidine (Catalog number 10610; Cayman Chemica; Ann Arbor, Mich.).

As used herein, "Cl-aminidine" refers to a compound having the structure of formula I:

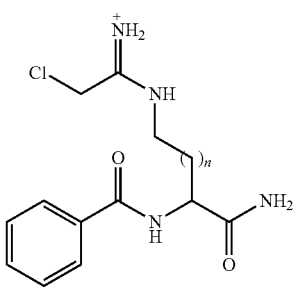

Formula I n = 1, 2, 3

As used herein, "Fl-amidine" refers to a compound having the structure of formula II:

Formula II

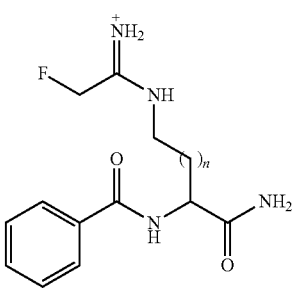

n = 1, 2, 3

In some embodiments, the PAD4 inhibitor can be an antibody, a polypeptide comprising a fragment of an antibody, or a nucleic acid. Antibodies, and methods of making them are described above herein.

In certain embodiments, the inhibitors are selective PAD4 inhibitors that are reversible, e.g. including but not limited to GSK484 and GSK199 (*Nat. Chem. Biology*, in Press).

In certain embodiments, the PAD4 inhibitor is a tetrazole analog, e.g. as described in Subramanian et al., Design, synthesis and biological evaluation of tetrazole analogs of Cl-amidine as protein arginine deiminase inhibitors J. Med. Chem., DOI: 10.1021/jm501636x Publication Date (Web): Jan. 5, 2015.

In one embodiment the tetrazole analog is biphenyl tetrazole tert-butyl Cl-amidine (BTT-Cl-amidine) that exhibits enhanced cell killing in a PAD4 expressing cells also blocks the formation of neutrophil extracellular traps (Subramanian et al., Supra).

Figure 13:
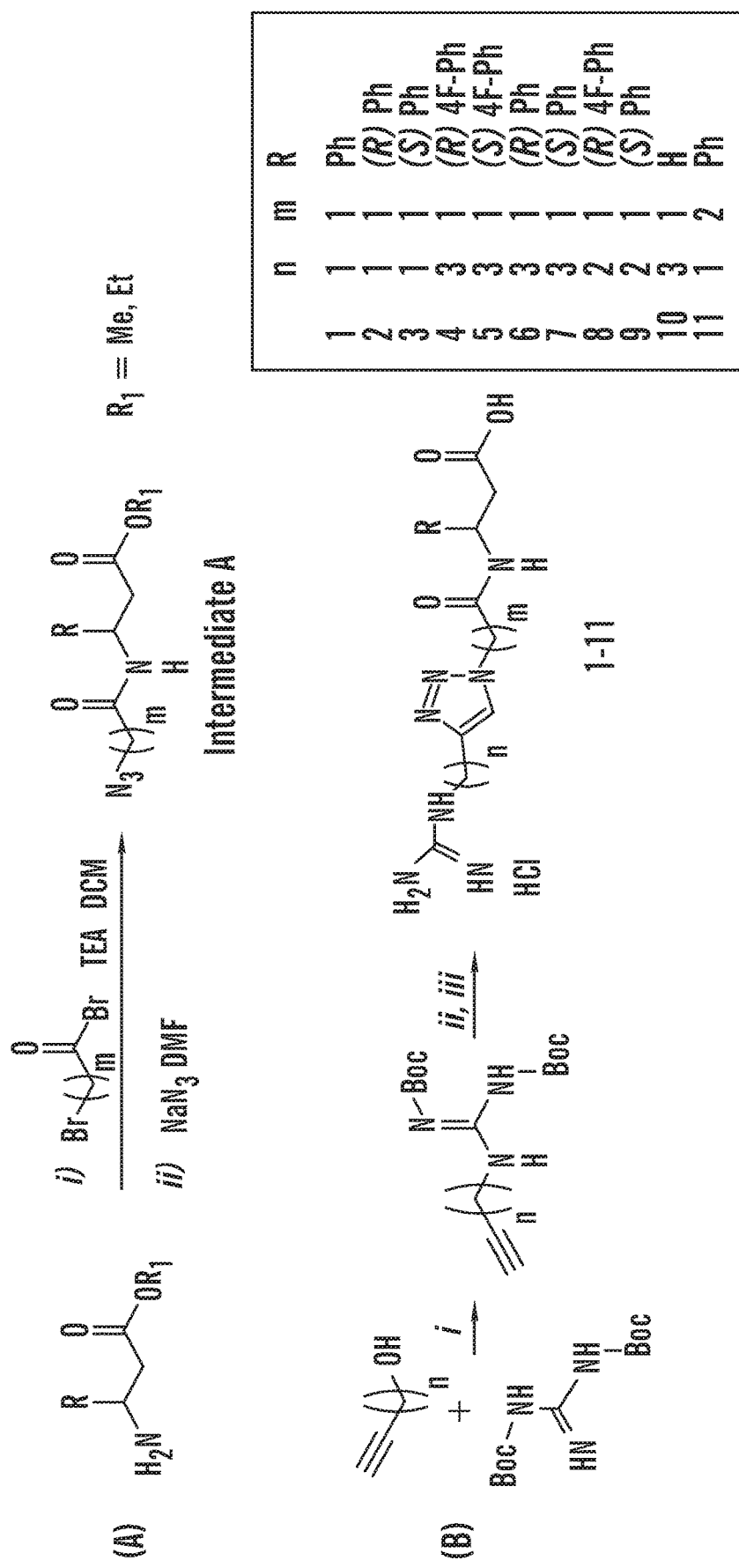
FIG. 13 is a schematic of chemical reactions to obtain peptidomimetic PAD4 inhibitors useful in the instant invention, e.g. compounds 1-16. This figure was obtained from Trabocchi et al. *J. Enzyme Inhib. Med. Chem.*, early online 1-6 (2014): DOI: 10.3109/147563662014947976, in order to illustrate compounds 1-16 described therein.
Figure 13:
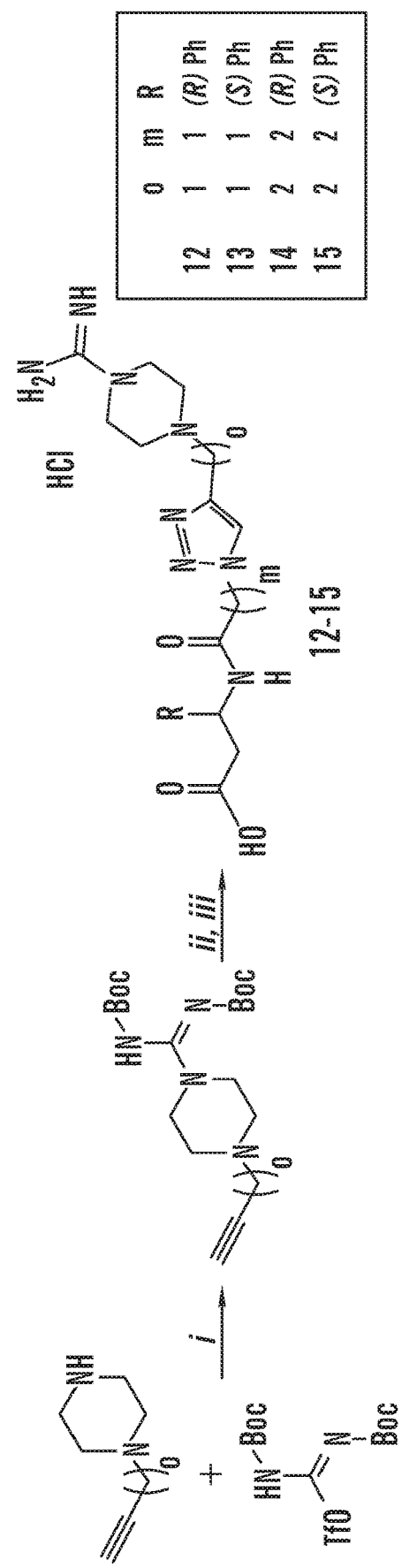
Figure 13:
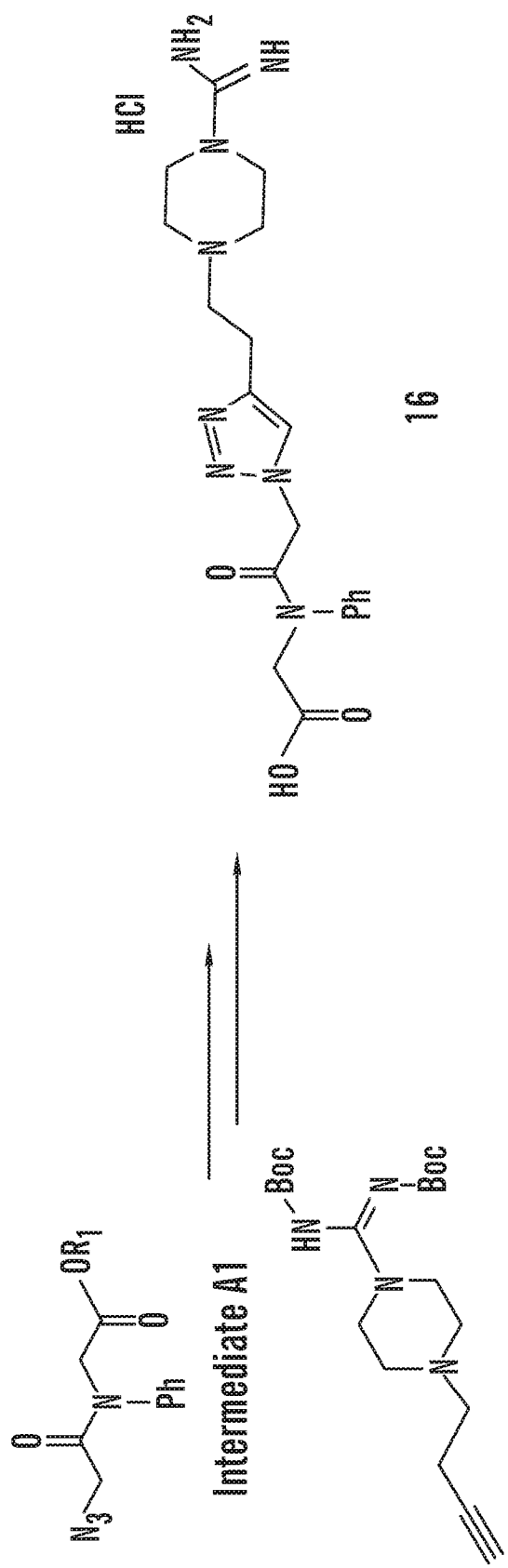

In certain embodiments, the PAD4 inhibitor is a peptidomimetic compound, e.g. including but not limited to 1,2,3-triazole peptidomimetic based derivatives incorporating beta-phenylalanine and guanidine scaffolds, e.g. as described in Trabocchi et al. Peptidomimetics as protein arginine deiminase 4 (PAD4) inhibitors, *J. Enzyme Inhib. Med. Chem.*, early online 1-6 (2014): DOI:10.3109/14756366.2014.947976. See also FIG. 13 that illustrates chemistry for 16 peptidomimetic PAD4 inhibitors as described in Trabocchi et al. Supra, e.g. 1,2,3-triazole peptidomimetic based derivatives.

In certain embodiments, the anti-NET compound is an inhibitor of NET release from cells, e.g. Cl-amidine blocks NET release from NZM neutrophils in vitro, other inhibitors of NET release are known to those of skill in the art.

In certain embodiments, the PAD4 inhibitor is BB-Cl-amidine (Knight et al. Peptidylarginine deiminase inhibition disrupts NET formation and protects against kidney, skin and vascular disease in lupus-prone MRL/lpr mice. *Ann Rheum Dis* doi:10.1136/annrheumdis-2014-205365, online August 2014).

In certain embodiments, the PAD4 inhibitor is YW3-56, as described in Wang et al., (2012) *J. Biol. Chem* 287(31): 25941-53.

PAD4 inhibitors which comprise a nucleic acid can be RNAi agents and/or gene silencing agents. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99% or more of the mRNA level found in the cell without the presence of the miRNA or RNA interference molecule. In one preferred embodiment, the mRNA levels are decreased by at least about 70%, about 80%, about 90%, about 95%, about 99% or more.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to an agent of the invention, are used interchangeably herein.

As used herein an "siRNA" refers to a nucleic acid that forms a double stranded RNA, which double stranded RNA has the ability to reduce or inhibit expression of a gene or target gene when the siRNA is present or expressed in the same cell as the target gene, sEH. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA, ribosomal DNA and cDNA. Other suitable nucleic acid molecules are RNA, including mRNA, rRNA and tRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid which is or which encodes a PAD4 inhibitor further comprises a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. As used herein, the term "viral vector" refers to a nucleic acid vector construct that includes at least one element of viral origin and has the capacity to be packaged into a viral vector particle. The viral vector can contain the PAD4 inhibitor in place of non-essential viral genes. The vector and/or particle may be utilized for the purpose of transferring any nucleic acids into cells either in vitro or in vivo. Numerous forms of viral vectors are known in the art. Vectors useful in the methods described herein can include, but are not limited to, plasmids, retroviral vectors, adenoviral vectors, adeno-associated viral vectors, and pox virus vectors.

The term "replication incompetent" when used in reference to a viral vector means the viral vector cannot further replicate and package its genomes. For example, when the cells of a subject are infected with replication incompetent recombinant adeno-associated virus (rAAV) virions, the heterologous (also known as transgene) gene is expressed in the patient's cells, but, the rAAV is replication defective (e.g., lacks accessory genes that encode essential proteins for packaging the virus) and viral particles cannot be formed in the patient's cells. The term "transduction" as used herein refers to the use of viral particles or viruses to introduce exogenous nucleic acids into a cell. The term "transfection" as used herein in reference to methods, such as chemical methods, to introduce exogenous nucleic acids, such as the nucleic acid sequences encoding an agent which decreases the activity and/or level of PAD4 as described herein, into a cell. As used herein, the term transfection does not encompass viral-based methods of introducing exogenous nucleic acids into a cell. Methods of transfection include physical treatments (electroporation, nanoparticles, magnetofection), and chemical-based transfection methods. Chemical-based transfection methods include, but are not limited to those that use cyclodextrin, polymers, liposomes, nanoparticles, cationic lipids or mixtures thereof (e.g., DOPA, Lipofectamine and UptiFectin), and cationic polymers, such as DEAE-dextran or polyethylenimine.

Methods of making RNAi agents which inhibit the expression and/or activity of PAD4 are well known in the art. Sequences complementary to the mRNA encoding PAD4 (i.e. SEQ ID NO: 1) can be used to design RNAi agents as described above herein.

The disruption of NETS can be monitored in vivo or in vitro. In one embodiment, the disruption of NETS is monitored by assessing the level of NET release in stored blood in the presence and absence of a test compound, e.g. by ELISA and/or determination of DNA concentration as described herein. In one embodiment, the ability of a test compound to disrupt NETS is monitored in vivo, e.g. by determining the ability to prevent platelet adhesion and aggregation.

Methods of Treatment

Described herein are methods of treating conditions such as diabetes (e.g. NET associated inflammation and delayed wound healing in diabetes), fibrosis, and skin wounds. As determined herein, these conditions are associated with an increased NETosis, and thus NETS can be targeted for treatment of theses disorders.

In one embodiment, a method of treating or preventing organ fibrosis in a subject is provided. The method comprises administering to a subject in need of treatment, a therapeutically effective amount of at least one anti-NET compound.

As used herein "Organ fibrosis" refers to fibrotic deposition that can occur in any organ. Fibrotic deposition (fibrosis) is a pathological condition characterized by excessive synthesis and accumulation of extracellular matrix proteins, loss of tissue homeostasis and organ failure.

As used herein "age-related organ fibrosis" refers to fibrosis that occurs in organs that has not been associated with any underlying disease, i.e. fibrosis occurring as a consequence of aging, e.g. idiopathic organ fibrosis, a non-limiting example; idiopathic pulmonary fibrosis (IPF).

As used herein, the term "preventing" as it relates to fibrosis refers to inhibition of intersiatial collagen deposition. In one embodiment, the deposition of collagen is decreased by at least 10%, at least 20%, at least 30%, at least 40%, or at least 50%. Deposition of collagen can be determined using methods well known to those of skill in the art, e.g. as described in Example 2, or by monitoring mRNA (See e.g. Casey et al. (1996) Biology of Reproduction, 55, 1253-1260). Collagen deposition can also be monitored using histology assays, e.g. in tissue samples. Collagen antibodies are commercially available from Rockland immunochemical corporation (Limerick, Pa.) e.g, COLLAGEN Type I Antibody 600-401-103-0.5, or from Santa Cruz Biotechnology (Dallas, Tex.).

As used herein, "treating" as it relates to organ fibrosis refers to reducing at least one measurable symptom of organ fibrosis. In one embodiment, the measurable symptom is loss of organ function. Accordingly, in certain embodiments, the symptoms of fibrosis are dependent upon the organ affected, e.g. kidney, liver, heart, lung. Those of skill in the art are well versed in detecting proper organ function. Non limiting examples include assessing blood to determine kidney glomerular filtration rate (kidney function), or level of liver enzymes (liver function), or determine levels of oxygen and $CO_2$ in the blood (lung function); or performing e.g. echocardiograms, or EKG's of the heart, in the case of e.g. age related fibrosis of the heart. Techniques for measuring organ function are standard in the art. In certain embodiments, organ function is increased or improved by least 10%, at least 20%, at least 30%, at least 40%, or at least, 50% as compared to function prior to treatment with the anti-NET compound.

Methods for diagnosis of fibrosis are well known and include for example examination of tissue sections for collagen deposition, imaging studies, and assessment of organ function.

Diabetes

Also provided are methods for treating NET associated complications in diabetes (e.g inflammation and delayed wound healing). The methods comprise administering a therapeutically effective amount of at least one anti-NET compound. In some embodiments, the subject has been diagnosed with Type 1, Type 1.5 or Type 2 diabetes, or has been determined to have a pre-diabetic condition.

The terms "diabetes" and "diabetes mellitus" are used interchangeably herein. A "pre-diabetic condition" refers to a metabolic state that is intermediate between normal glucose homeostasis, metabolism, and states seen in frank Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL)(whole blood 6.1 mmol/L; 110 mg/dL). Metabolic Syndrome according to National Cholesterol Education Program (NCEP) criteria are defined as having at least three of the following: blood pressure 130/85 mm Hg or higher; fasting plasma glucose 6.1 mmol/L or higher; waist circumference >102 cm (men) or >88 cm (women); triglycerides 1.7 mmol/L or higher; and HDL cholesterol <1.0 mmol/L (men) or 1.3 mmol/L (women).

Type 1 diabetes is an autoimmune disease that results in destruction of insulin-producing beta cells of the pancreas. Lack of insulin causes an increase of fasting blood glucose (around 70-120 mg/dL in nondiabetic people) that begins to appear in the urine above the renal threshold (about 190-200 mg/dl in most people). The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level of 11.1 mmol/L or higher (200 mg/dL or higher).

Type 1 diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycated). An A1C level of 6.5 percent or higher on two separate tests is indicative of diabetes. A result between 6 and 6.5 percent is considered prediabetic, which indicates a high risk of developing diabetes.

The Random Blood Glucose Test comprises obtaining a blood sample at a random time point from a subject suspected of having diabetes. Blood glucose values can be expressed in milligrams per deciliter (mg/dL) or millimoles per liter (mmol/L). A random blood glucose level of 200 mg/dL (11.1 mmol/L) or higher indicates the subject likely has diabetes, especially when coupled with any of the signs and symptoms of diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of diabetes. Type 1 diabetes can be distinguished from type 2 diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 diabetes as it appears that the immune system is involved in Type 1 diabetes etiology. Type 1.5 (also known as LADA Diabetes) is performed by determining the presence of anti-LADA antibodies.

Each of the diabetic conditions have overlapping symptoms. Exemplary symptoms of diabetes include, but are not limited to, excessive thirst (polydipsia), frequent urination (polyuria), extreme hunger (polyphagia), extreme fatigue, weight loss, hyperglycemia, low levels of insulin, high blood sugar (e.g., sugar levels over 250 mg, over 300 mg), presence of ketones present in urine, fatigue, dry and/or itchy skin, blurred vision, slow healing cuts or sores, more infections than usual, numbness and tingling in feet, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, and combinations thereof.

A therapeutically effective amount of an anti-NET compound is the amount of a compound administered to a subject that is sufficient to produce a statistically significant, measurable change in a symptom of Type 1, Type 1.5 or Type 2 diabetes that has NET involvement, e.g. increased inflammation or delayed wound healing.

In certain embodiments, the symptom of diabetes that has NET involvement is ameliorated by at least 10%, at least 20%, at least 30%, at least 40%, or at least 50%, as compared to the symptom prior to treatment with the anti-NET compound.

In certain embodiments, the symptom of diabetes having NET involvement is delay of wound healing.

In certain embodiments, the symptom of diabetes having NET involvement is inflammation. Reduction in inflammation can be monitored by physical examination, as well as the reduction in the presence of inflammatory markers. Acute inflammatory markers known to the person skilled in the art include C-reactive protein (CRP), fibrinogen, D-dimer, serum amyloid A (SAA), pregnancy-associated polypeptide A (PAPP-A), intercellular adhesion molecules (e.g. ICAM-1, VCAM-1), IL-1-beta, IL-6, IL-8, IL-17 IL-18/IL-18b; TNF-alpha; myeloperoxidase (MPO); TF; monocyte chemoattractant protein 1 (MCP-1); P-selectin; E-selectin; platelet activating factor acetyl hydrolase (PAF-AH); von Willebrand Factor (vWF). Preferred markers of acute inflammation for use in a method described herein are CRP, fibrinogen, D-dimer and SAA, of which CRP and D-dimer are more preferably used. D-Dimer is a marker of thrombolysis and its generation may be NET-dependent.

In certain embodiments, a method for treatment of diabetes is provided that comprises the administration of a therapeutically effective amount of an agent used to treat diabetes and at least one anti-NET compound. In one embodiment, the agent used to treat diabetes is insulin. Other agents used to treat diabetes include, but are not limited to, Biguanides, Metformin (Glucophage), Metformin liquid (Riomet), Metformin extended release (Glucophage XR, Fortamet, Glumetza), Sulfonylureas, Glimepiride (Amaryl), Glyburide (Diabeta, Micronase), Glipizide (Glucotrol, Glucotrol XL), Micronized glyburide (Glynase), Meglitinides, Repaglinide (Prandin), D-Phenylalanine Derivatives, Nateglinide (Starlix), Thiazolidinediones, Pioglitazone (TZDs), Pioglitazone, (Actos), DPP-4 Inhibitor, Sitagliptin (Januvia), Saxagliptin (Onglyza), Linagliptin (Tradjenta), Alpha-glucosidase, Acarbose (Precose), Miglitol (Glyset), Bile Acid Sequestrants, Colesevelam (Welchol), Pioglitazone & metformin) (Actoplus Met), Glyburide & metformin (Glucovance), Glipizide & metformin (Metaglip), Sitagliptin & metformin (Janumet), Saxagliptin & metformin (kombiglyze), Repaglinide & metformin (Prandimet) and, Pioglitazone & glimepiride (Duetact).

Wound Healing

Also provided are methods for treatments of wounds. In certain embodiments the patient that is administered an anti-net compound for the treatment of wounds, has previously been diagnosed with diabetes.

As used herein "wound healing" refers to the intricate process where the skin (or another organ-tissue) repairs itself after injury. The classic model of wound healing is divided into three or four sequential, yet overlapping, phases: (1) hemostasis, when clot stops bleeding, (2) inflammation, (3) proliferation and (4) remodeling. Upon injury to the skin, a set of complex biochemical events takes place in a closely orchestrated cascade to repair the damage (See e.g., Stadelmann, W K; Digenis, A G; Tobin, G R (1998). "Physiology and healing dynamics of chronic cutaneous wounds". American journal of surgery 176 (2A Suppl): 26S-38S). During the inflammation phase, bacteria and cell debris are phagocytosed and removed from the wound by white blood cells. Platelet-derived growth factors (stored in the alpha granules of the platelets) are released into the wound that cause the migration and division of cells during the proliferative phase. The proliferation phase is characterized by angiogenesis, collagen deposition, granulation tissue formation, epithelialization, and wound contraction (Midwood, K. S.; (2004). "Tissue repair and the dynamics of the extracellular matrix". The International Journal of Biochemistry & Cell Biology 36 (6): 1031-1037). New blood vessels are formed and fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

The growth of tissue around the wound site is a result of the migration of cells and collagen deposition by these cells. The alignment of collagen describes the degree of scarring; basket-weave orientation of collagen is characteristic of normal skin, whereas aligned collagen fibers lead to significant scarring.

As used herein the term "facilitating wound healing" refers to an acceleration the process of normal wound healing and/or inhibiting the amount of formation of scar tissue that occurs from the wound healing process.

In certain embodiments, effective treatment can also be determined by measuring the diameter of the wound over time. In certain embodiments, the diameter of the wound is decreased by at least 10%, at least 20%, at least 30%, at least 40%, or at least 50%/per unit time as compared to the diameter decrease per unit time usually observed in patients in the process of wound healing.

In certain embodiments, the formation of scar tissue is reduced by at least 10%, at least 20%, at least 30%, at least 40%, or at least 50%, as compared to an expected healing process in the absence of the anti-NET compound.

In certain embodiments, the anti-NET compound is provided in a pharmaceutically acceptable carrier that is time released, or that is integrated in a skin graft, or delivery device.

In certain embodiments, the treatment of a wound is assessed by monitoring dissolution of NETS in the wound.

Some embodiments relate to the use of at least one anti-NET compound and compositions containing at least one such anti-NET compound for the treatment of diabetes, treatment of fibrosis, or for facilitating wound healing. A composition containing an anti-NET compound is used to reduce the severity, duration, or number of symptoms associated with the condition to be treated.

In one embodiment, a single administration of an anti-NET compound decreases the level of an indicator, symptom, or marker of fibrosis by at least 10%, e.g., by at least 20%, at least 30%, at least 50%, at least 75%, at least 75%, at least 90%, at least 95%, at least 99% or more as compared to the level of the indicator, symptom, or maker of a cardiovascular condition prior to treatment with the anti-NET compound.

In certain embodiments, a single administration of an anti-NET compound to a patient decreases the deposition of interstiatial collagen in the patient's organ by at least 10%, e.g., by at least 20%, at least 30%, at least 50%, at least 75%, at least 75%, at least 90%, at least 95%, at least 99% or more as compared to the presence of collagen in the absence of treatment with the anti-NET compound.

In one embodiment, a single administration of an anti-NET compound to a group of patients facilitates wound healing by at least 10%, e.g., by at least 10%, by at least 20%, at least 30%, at least 50%, at least 75%, a at least 75%, at least 90%, at least 95%, at least 99% or more as compared to the rate of wound healing in a group of patients not administered the anti-NET compound.

The methods described herein relate to the use of at least one anti-NET compound or a pharmaceutical composition for treatment. In certain embodiments the at least one anti-NET compound is administered as a prophylactic, i.e. a patient exhibiting symptoms, markers, or indications of a condition described herein can be treated with at least one anti-NET compound in order to prevent or reverse the progression of the condition or to lessen the severity of future symptoms, markers, or indicators of the condition.

In certain embodiments the methods provided herein involve the use of at least one anti-NET compound. In further embodiments, the method provided herein involves the use of two or more anti-NET compounds, non limiting examples –a PAD4 inhibitor and a DNase.

In certain embodiments, the effective dose of at least one anti-NET compound is administered to a patient repeatedly.

In certain embodiments, administering a single dose of an anti-NET compound to a patient decreases the concentration of NETs at a target site (e.g. organ or wound) by least 10%, e.g., by at least 20%, at least 30%, at least 50%, at least 75%, or more as compared to the level of NETs prior to treatment with the anti-NET compound.

In one embodiment, a single administration of an anti-NET compound to a patient decreases the level of an indicator, symptom, or marker of a condition described herein by at least 10%, e.g., by at least 20%, at least 30%, at least 50%, at least 75%, at least 90% more as compared to the level of the indicator, symptom, or maker of the condition prior to treatment with the anti-NET compound.

In certain embodiments the composition comprising at least one anti-NET compound further comprises a pharmaceutically acceptable carrier. Non-limiting examples of antibiotics include, e.g., kanamycin, actinomycin D, doxorubicin, bleomycin, and mithramycin. Antibiotics are well known to those of skill in the art.

In some embodiments, the at least one anti-NET compound or a pharmaceutical composition thereof, is administered with another pharmaceutically active agent, e.g. a pharmaceutically active agent for treating a patient with a wound, fibrosis or diabetes. The anti-NET compound can be administered in combination with other pharmaceuticals and/or other therapeutic methods of treatment concurrently.

In some embodiments, the additional agent administered is an antibiotic, e.g. when the anti-NET compound is used for facilitating wound healing.

In some embodiments, the additional agent administered is an anti-inflammatory agent, anti-A number of anti-inflammatory agents are known in the art, non-limiting examples of which are Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone, Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

In some embodiments the additional agent administered is an anti-fibrolytic agent is administered. Additional anti-fibrinolytic agents include, for example, Plasminogen, prekallikrein, kininogens, Factors XII, XIIIa, plasminogen proactivator, tissue plasminogen activator[TPA], Streptokinase; Urokinase: Anisoylated Plasminogen-Streptokinase Activator Complex; Pro-Urokinase; (Pro-UK); rTPA (alteplase or activase; r denotes recombinant), rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; tenecteplase, retaplase; Trifenagrel; Warfarin; Dextrans.

In some embodiments, the additional agent administered is agent to treat diabetes. Such agents include those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyclopyramide, and Glimepiride), meglitinides ("glinides") (e.g., Nateglinide, Repaglinide and Mitiglinide), glucagonlike peptide-1 (GLP-1) and analogs (e.g., Exendin-4, Exenatide, Liraglutide, Albiglutide), insulin and insulin analogs (e.g., Insulin lispro, Insulin aspart, Insluin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapgliflozin, Remogliflozin and Sergliflozin) and others (e.g. Benfluorex and Tolrestat).

The anti-NET compound and the pharmaceutically active agent can be administrated to the subject in the same pharmaceutical composition or in different pharmaceutical compositions (at the same time or at different times). When administrated at different times, an anti-NET compound and the pharmaceutically active agent can be administered within 5 minutes, 10 minutes, 20 minutes, 60 minutes, 2 hours, 3 hours, 4, hours, 8 hours, 12 hours, 24 hours of administration of the other. When the anti-NET compound, and the pharmaceutically active agent are administered in different pharmaceutical compositions, routes of administration can be different. For example, the anti-NET compound is administered by any appropriate route known in the art including, but not limited to oral or parenteral routes, including intravenous, intramuscular, subcutaneous, transdermal, airway (aerosol), pulmonary, nasal, rectal, and topical (including buccal and sublingual) administration, and pharmaceutically active agent is administration by a different route, e.g. a route commonly used in the art for administration of said pharmaceutically active agent. In a non-limiting example, an anti-NET compound can be administered orally, while a pharmaceutically active agent can be administrated subcutaneously.

Efficacy of treatment or prevention of disease can be assessed, for example by measuring a marker, indicator, or symptom of the condition, or any other measurable parameter appropriate. It is well within the ability of one skilled in the art to monitor efficacy of treatment or prevention by measuring any one of such parameters, or any combination of parameters.

A treatment is evident when there is a statistically significant improvement in one or more parameters of health, or by a failure to worsen or to develop symptoms where they would otherwise be anticipated. As an example, a favorable change of at least 10% in a measurable parameter of fibrosis, wound healing, or diabetes, and preferably at least 20%, 30%, 40%, 50% or more can be indicative of effective treatment. Efficacy for a given anti-NET compound or formulation of that drug can also be judged using an experimental animal model for a condition described herein as known in the art. When using an experimental animal model, efficacy of treatment is evidenced when a statistically significant increase in a marker is observed.

The dosage ranges for the administration of an anti-NET compound depend upon the form of the compound, its potency, and the extent to which symptoms, markers, or indicators of a condition described herein are desired to be reduced, for example the percentage reduction desired for collagen deposition, inflammation, scar size. The dosage should not be so large as to cause adverse side effects, such as hyperviscosity syndromes, pulmonary edema, congestive heart failure, and the like. Generally, the dosage will vary with the age, condition, and sex of the patient and can be determined by one of skill in the art. The dosage can also be adjusted by the individual physician in the event of any complication.

Patients can be administered a therapeutic amount of an anti-NET compound, such as 0.5 ng/kg, 1.0 ng/kg, 2.0 ng/kg, 2.5 ng/kg, 5 ng/kg, 10 ng/kg, 15 ng/kg, 20 ng/kg, 25 ng/kg, 30 ng/kg, 40 ng/kg or 50 ng/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg or 50 mg/kg. The anti-NET compound can be administered, for example, by intravenous infusion over a period of time, such as over a 5 minute, 10 minute, 15 minute, 20 minute, or 25 minute period. The administration is repeated, for example, on a regular basis, such as hourly for 3 hours, 6 hours, 12 hours or longer or such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the anti-NET compound can reduce levels of a marker or symptom of a condition described herein, e.g., inflammation or collagen deposition by at least 10%, at least 15%, at least 20%, at least 25%, at least 30%, at least 40%, at least 50%, at least 60%, at least 70%, at least 80% or at least 90% or more.

Before administration of a full dose of the anti-NET compound, patients can be administered a smaller dose, such as a 5% infusion, and monitored for adverse effects, such as an allergic reaction.

In general, the efficacy of a given treatment can be monitored by assessing the disruption of NETs, as increased NETs have been associated with the conditions described herein. A reduction in NETs can be determined by tissue analysis and anti-Net antibodies. However, a treatment is considered "effective treatment," as the term is used herein, if any one or all of the signs or symptoms of a condition described herein are altered in a beneficial manner, other clinically accepted symptoms are improved, or even ameliorated, e.g., by at least 10% following treatment with a compound as described herein. Efficacy can also be measured by a failure of an individual to worsen as assessed by hospitalization, or need for medical interventions (i.e., progression of the disease is halted). Another marker of the efficacy of treatment as described herein is survival. Statistical survival rates for specific conditions described herein are well established—when an individual or group of individuals treated according to the methods described herein survives beyond the expected time or at a greater than expected rate, the treatment can be considered effective.

Pharmaceutical Compositions

For administration to a subject, the compounds can be provided in pharmaceutically acceptable compositions. These pharmaceutically acceptable compositions comprise a therapeutically-effective amount of at least one anti-NET compound described above, formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally. Additionally, compounds can be implanted into a patient or injected using a drug delivery system. Coated delivery devices can also be useful. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; 6,747,014; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, binding agents, fillers, lubricants, coloring agents, disintegrants, release agents, coating agents, sweetening agents, flavoring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "pharmaceutically acceptable carrier" or the like are used interchangeably herein.

Many organized surfactant structures have been studied and used for the formulation of drugs. These include monolayers, micelles, bilayers and vesicles. Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S.T.P. Pharma. Sci., 1994, 4, 6, 466). Liposomes can comprise a number of different phospholipids, lipids, glycolipids, and/or polymers which can impart specific properties useful in certain applications and which have been described in the art (Allen et al., FEBS Letters, 1987, 223, 42; Wu et al., Cancer Research, 1993, 53, 3765; Papahadjopoulos et al. Ann. N.Y. Acad. Sci., 1987, 507, 64; Gabizon et al. PNAS, 1988, 85, 6949; Klibanov et al. FEBS Lett., 1990, 268, 235; Sunamoto et al. Bull. Chem. Soc. Jpn., 1980, 53, 2778; Illum et al. FEBS Lett., 1984, 167, 79; Blume et al. Biochimica et Biophysica Acta, 1990, 1029, 91; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions described herein can be prepared and formulated as emulsions or microemulsions. Emulsions are typically heterogeneous systems of one liquid dispersed in another in the form of droplets usually exceeding 0.1 μm in diameter and have been described in the art. microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

In one embodiment, the liposome or emulsion formulation comprises a surfactant. Surfactants find wide application in formulations such as emulsions (including microemulsions) and liposomes. The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285). Suitable surfactants include fatty acids and/or esters or salts thereof, bile acids and/or salts thereof. In certain embodiments, the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

In some embodiments, various penetration enhancers can be employed to effect the efficient delivery of anti-NET compounds across cell membranes. Penetration enhancers can be classified as belonging to one of five broad categories, i.e., surfactants, fatty acids, bile salts, chelating agents, and non-chelating non-surfactants all of which have been described elsewhere (see e.g., Malmsten, M. Surfactants and polymers in drug delivery, Informa Health Care, New York, N.Y., 2002; Lee et al., Critical Reviews in Therapeutic Drug Carrier Systems, 1991, p.92; Takahashi et al., J. Pharm. Pharmacol., 1988, 40, 252; Touitou, E., et al. Enhancement in Drug Delivery, CRC Press, Danvers, Mass., 2006; Muranishi, Critical Reviews in Therapeutic Drug Carrier Systems, 1990, 7, 1-33; El Hariri et al., J. Pharm. Pharmacol., 1992, 44, 651-654; Brunton, Chapter 38 in: Goodman & Gilman's The Pharmacological Basis of Therapeutics, 9th Ed., Hardman et al. Eds., McGraw-Hill, New York, 1996, pp. 934-935; Swinyard, Chapter 39 In: Remington's Pharmaceutical Sciences, 18th Ed., Gennaro, ed., Mack Publishing Co., Easton, Pa., 1990, pages 782-783; Yamamoto et al., J. Pharm. Exp. Ther., 1992, 263, 25; Yamashita et al., J. Pharm. Sci., 1990, 79, 579-583; Jarrett, J. Chromatogr., 1993, 618, 315-339; Katdare, A. et al., Excipient development for pharmaceutical, biotechnology, and drug delivery, CRC Press, Danvers, Mass., 2006; Buur et al., J. Control Rel., 1990, 14, 43-51)

Oral formulations and their preparation are described in detail in U.S. Pat. No. 6,887,906, US Publication. No. 20030027780, and U.S. Pat. No. 6,747,014, each of which is incorporated herein by reference. Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran. The suspension can also contain stabilizers.

A composition comprising at least one anti-NET compound can be administered directly to the airways of a subject in the form of an aerosol or by nebulization. For use as aerosols, an anti-NET compound in solution or suspension may be packaged in a pressurized aerosol container together with suitable propellants, for example, hydrocarbon propellants like propane, butane, or isobutane with conventional adjuvants. An anti-NET compound can also be administered in a non-pressurized form such as in a nebulizer or atomizer.

An anti-NET compound can also be administered directly to the airways in the form of a dry powder. For use as a dry powder, an anti-NET compound can be administered by use of an inhaler. Exemplary inhalers include metered dose inhalers and dry powdered inhalers.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The compositions can also be delivered by injection, e.g. locally to fibrotic tissue and organs. In certain embodiments, the compositions are delivered using a device, or bandage, used in the process of treatment of a wound.

The compositions described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions described herein, such as dyes, flavoring agents, preservatives, antioxidants, opacifiers, thickening agents and stabilizers. However, such materials, when added, should not unduly interfere with the biological activities of the components of the compositions described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the anti-NET compound(s) of the formulation.

As used herein, the phrase "subject in need of treatment" refers to a subject who is diagnosed with or identified as suffering from, having or at risk for developing the condition to be treated, e.g. fibrosis, diabetes or wounds.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred. Murine genetics and surgical techniques have generated a number of mouse models for the study of fibrosis and diabetes or mice impaired in the ability to limit the concentration of NETs. Such models can be used for in vivo testing of anti-NET compounds, as well as for determining a therapeutically effective dose. A suitable mouse model is, for example, the DNase$^{-/-}$ mouse described herein or the mouse model of stroke described herein.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The amount of an anti-NET compound which can be combined with a carrier material to produce a single dosage form will generally be that amount of the compound which produces a therapeutic effect. Generally out of one hundred percent, this amount will range from about 0.1% to 99% of compound, preferably from about 5% to about 70%, most preferably from 10% to about 30%.

The dosage can be determined by a physician and adjusted, as necessary, to suit observed effects of the treatment. Generally, the compositions are administered so that the anti-NET compound is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg etc. . . . It is to be further understood that the ranges intermediate to the given above are also within the scope of the methods and compositions described herein, for example, in the range 1 mg/kg to 10 mg/kg, dose ranges such as 2 mg/kg to 8 mg/kg, 3 mg/kg to 7 mg/kg, 4 mg/kg to 6 mg/kg etc.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the anti-NET compound. The desired dose can be administered at one time or divided into subdoses, e.g., 2-4 subdoses and administered over a period of time, e.g., at appropriate intervals through the day or other appropriate schedule. Such subdoses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more. The desired dose can be administered using continuous infusion or delivery through a controlled release formulation. In that case, the anti-NET compound contained in each sub-dose must be correspondingly smaller in order to achieve the total daily dosage. The dosage unit can also be compounded for delivery over several days, e.g., using a conventional sustained release formulation which provides sustained release of the anti-NET compound over a several day period. Sustained release formulations are well known in the art and are particularly useful for delivery of agents at a particular site, such as could be used with the agents described herein. In this embodiment, the dosage unit contains a corresponding multiple of the daily dose.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the anti-NET compounds described herein can be made using conventional methodologies or on the basis of in vivo testing using an appropriate animal model, as described elsewhere herein.

A Method of Assessing Efficacy of Anti-NET Treatments

As described herein, the inventors have found that increased levels of NETs are associated with impaired wound healing, diabetes and fibrosis, and have provided methods of treating or preventing these disorders by administering one or more anti-NET compounds. Accordingly, some embodiments are generally related to assays and methods for assessing the efficacy of the administration of one of more anti-NET compounds. In certain embodiments, the assays and methods are directed to determination of the level of NETs in a biological sample of a subject.

The methods and assays described herein include determining the level of NETs in samples obtained from a patient before and after treatment with one or more anti-NET compounds, wherein a reduction in the level of NETs following the treatment with the anti-NET compound is indicative of efficacy.

The sample obtained from a patient can include, but is not limited to, blood or blood products. Blood products in the context of samples obtained from a patient can include, but are not limited to, any component of a patient's blood (e.g. plasma) and/or blood or a component thereof that has been treated or processed (e.g. with an anti-coagulant or preservative).

In certain embodiments, the sample obtained from the patient prior to treatment with one or more anti-NET compounds can be obtained at any time prior to administration of the anti-NET compound, for example, about 1 minute prior to treatment, about 10 minutes prior to treatment, about 1 hour prior to treatment, about 1 day prior to treatment, about 1 week prior to treatment, about 2 weeks prior to treatment, about 1 month prior to treatment, or earlier. In certain embodiments, the sample obtained from the patient after treatment with one or more anti-NET compounds can be obtained at any time after administration of the anti-NET compound, for example, about 10 minutes after treatment, about 1 hour after treatment, about 1 day after treatment, about 1 week after treatment, about 2 weeks after treatment, or later.

In certain embodiments, the level of NETs is determined using labeled DNA detection reagents (i.e. Hoechst 33258 or SytoxGreen), immunodetection of citullinated histones, detection of nucleosomes and/or components thereof (i.e. Cell death detection kit, Roche), or electrophoresis of plasma DNA.

Some embodiments of the present invention may be defined in any of the following numbered paragraphs:

Paragraph 1. A method of treating or preventing organ fibrosis in a subject, the method comprising:
administering to a subject in need of treatment, a therapeutically effective amount of at least one anti-NET compound.

Paragraph 2. The method of paragraph 1, wherein the at least one anti-NET compound is selected from the group consisting of:
DNase; a histone-degrading enzyme; an inhibitor of chromatin decondensation; an antibody against a component of a NET; a protease inhibitor, an elastase inhibitor; and a PAD4 inhibitor.

Paragraph 3. The method of any of paragraphs 1 to 2, wherein the PAD4 inhibitor is selected from the group consisting of:
Cl-amidine and F-amidine.

Paragraph 4. The method of any of paragraphs 1 to 3, wherein said therapeutically effective amount of anti-NET compound is administered prophylactically.

Paragraph 5. The method of any of paragraphs 1 to 4, wherein the subjects age is selected from the group consisting of: over 40 years of age, over 30 years of age, over 50 years of age, over 60 years of age, and over 70 years of age.

Paragraph 6. The method of any of paragraphs 1 to 5, wherein the subject is diagnosed with a disease selected from the group consisting of: heart disease, lung disease, kidney disease, liver disease, and diabetes.

Paragraph 7. The method of any of paragraphs 1 to 6, wherein said therapeutically effective amount of anti-NET compound is given repeatedly.

Paragraph 8. The method any of paragraphs 1 to 7, wherein the subject is diagnosed as having age-related organ fibrosis.

Paragraph 9. The method of any of paragraphs 1 to 8, wherein the subject is diagnosed with an organ fibrosis selected from the group consisting of: heart fibrosis, lung fibrosis, liver fibrosis, kidney fibrosis, skin fibrosis, soft tissue fibrosis, and intestine fibrosis.

Paragraph 10. The method of any of paragraphs 1 to 9, wherein the administration is local administration to one or more target sites in an organ having fibrosis.

Paragraph 11. The method of any of paragraphs 1 to 10, wherein the subject does not have cystic fibrosis.

Paragraph 12. A method for facilitating wound healing comprising administering a therapeutically effective amount of at least one anti-NET compound.

Paragraph 13. The method of claim 12, wherein the anti-NET compound is selected from the group consisting of:
DNase; a histone-degrading enzyme; an inhibitor of chromatin decondensation; an antibody against a component of a NET; a protease inhibitor, an elastase inhibitor; and a PAD4 inhibitor.

Paragraph 14. The method of any of paragraphs 12 to 13, wherein a DNAse and an additional anti-NET compound selected from the group consisting of; a histone-degrading enzyme; an inhibitor of chromatin decondensation; a NET release inhibitor; an antibody against a component of a NET; a protease inhibitor, an elastase inhibitor; and a PAD4 inhibitor, are administered.

Paragraph 15. The method of any of paragraphs 12 to 13, wherein the anti-NET compound is not a DNase.

Paragraph 16. The method of any of paragraphs 12 to 15, wherein the PAD4 inhibitor is selected from the group consisting of: Cl-amidine and F-amidine.

Paragraph 17. The method of any of paragraphs 12 to 16, wherein said therapeutically effective amount of anti-NET compound is administered prophylactically.

Paragraph 18. The method of any of paragraphs 12 to 17, wherein said therapeutically effective amount of anti-NET compound is given repeatedly.

Paragraph 19. The method of any of paragraphs 12 to 18, wherein the subject is diagnosed as having diabetes.

Paragraph 20. A method for treating NET associated inflammation and complications in diabetes comprising administering a therapeutically effective amount of at least one anti-NET compound.

Paragraph 21. The method of claim 20, wherein the anti-NET compound is selected from the group consisting of:
DNase; a histone-degrading enzyme; an inhibitor of chromatin decondensation; a NET release inhibitor; an antibody against a component of a NET; a protease inhibitor, an elastase inhibitor; and a PAD4 inhibitor.

Paragraph 22. The method of any of paragraphs 20 to 21, wherein the anti-NET compound is not a DNase.

Paragraph 23. The method of any of paragraphs 20 to 22, wherein the anti-NET compound is not an elastase inhibitor.

Paragraph 24. The method any of paragraphs 20 to 23, wherein the PAD4 inhibitor is selected from the group consisting of:
Cl-amidine and F-amidine.

Paragraph 25. The method of any of paragraphs 20 to 24, wherein said therapeutically effective amount of anti-NET compound is administered prophylactically.

Paragraph 26. The method of any of paragraphs 20 to 25, wherein said therapeutically effective amount of anti-NET compound is given repeatedly.

Paragraph 27. The method of any of paragraphs 20 to 26, wherein the subject is diagnosed as having diabetes type 1.

Paragraph 28. The method of any of paragraphs 20 to 27, wherein the subject is diagnosed as having diabetes type II.

Paragraph 29. The method of any of paragraphs 20 to 28, wherein inflammation is reduced by at least 10%, at least 20%, at least 30%, or at least 50% as compared to inflammation prior to treatment.

EXAMPLES

Example 1: Nets Impair Wound Healing, Especially in Diabetes

Methods

Animals.

All animal procedures were reviewed and approved by the Institutional Animal Care and Use Committee of Boston Children's Hospital. $CD18^{-/-}$ mice and $PAD4^{-/-}$ mice were on a C57BL/6J background and were routinely crossed to WT mice from the Jackson Laboratory (Bar Harbor, Me.). Age- and gender-matched control mice included the WT littermates of the two strains and C57BL/6J purchased from the Jackson Laboratory. Nine-week old male diabetic db/db mice and the normoglycemic control m+/db mice were purchased from Jackson Laboratory. All mice were fed standard lab diet and maintained under standard laboratory conditions free of specific pathogens. Sample size was chosen based on previous experience with the animal strains and animal models. Genotypes of animals were open to investigators.

Human Blood Cell Samples.

The study was approved by the Institutional Review Board of Boston Children's Hospital and Joslin Diabetes Center, and conformed to the principles outlined in the Declaration of Helsinki. Blood samples were obtained after written informed consent was obtained. Diabetic patients were recruited only if they were below 70 years old, not on steroid or other immunosuppressive medications, not presenting any signs of active infection (fever, high leukocyte count and diagnosis of infection), no diagnosis of cancer in the past 5 years and no overt heart failure.

Induction of Diabetic Murine Model.

Mice were induced to be diabetic using multiple low dose injections of streptozotocin (STZ). Six to 8-week old male C57BL/6 or PAD4$^{-/-}$ mice were randomized into treatment groups of either vehicle or STZ according to their blood glucose levels and body weight at baseline. Mice were fasted for 5 hours and then injected with vehicle or STZ (i.p., 50 mg/kg per day, pH 4, dissolved in 0.1 M sodium citrate buffer) for 5 consecutive days. Fed blood glucose level was measured starting 1 week afterwards. Mice with fed blood glucose level above 300 mg/dL were considered diabetic and used for further experiments. Pancreatic islets were stained for insulin using a rabbit polyclonal anti-insulin antibody (1:500, Cell Signaling, Cat. no. 4590).

Measurement of Basal H3Cit on Mouse Cytospins.

Murine whole blood was collected via the retro-orbital venous plexus. Red blood cells were lysed using ACK lysing buffer. After centrifugation, cells were resuspended in 7.5% BSA/PBS and spun at 1600 rpm for 4 minutes onto slides and instantly fixed with 4% PFA at 4° C. overnight and then stained using rabbit polyclonal anti-H3Cit (1:1,000, abcam, Cat. no. ab5103) and rat monoclonal anti-mouse Ly6G (1:500, BD Pharmingen, Cat. no. 551459). H3Cit+ neutrophils were determined by thresholding analysis using ImageJ software (NIH).

Mouse Neutrophil Isolation and NETosis Assay.

Peripheral blood neutrophils were isolated with Percoll (GE Healthcare) gradients as described[39]. Purity of cells was >90% as determined by Wright-Giemsa staining. Neutrophils were resuspended in HBSS (with calcium, magnesium and 5.5 mM glucose) for experiments involving high glucose; otherwise they were resuspended in HEPES-buffered RPMI medium. Neutrophils were plated at 50,000 cells/well in 96-well glass-bottomed plates and stimulated with *Klebsiella pneumoniae* LPS (Sigma) at indicated concentrations for 2.5 hours. For high glucose experiments, neutrophils were isolated from normoglycemic mice and pre-incubated for 1 h in media with normal (5.5 mM) or high (22 mM) glucose concentration. Twenty-two mM corresponds to 396 mg/dL, which is similar to the fed blood glucose level in STZ-induced mice 8 weeks post-induction (376.3±26.9 mg/dL). Mannitol (16.5 mM in medium with 5.5 mM glucose) was employed as an osmotic control. LPS (in respective medium) was added and neutrophils were further incubated for 2.5 h. Cells were then fixed in 2% PFA, permeabilized, blocked, stained with anti-H3Cit (1:1,000, abcam, Cat. no. ab5103), Alexa Fluor 488-conjugated anti-rabbit secondary antibody (1:1,500, Invitrogen) and Hoechst 33342 (1:10,000, Invitrogen). Percentages of H3Cit$^{high}$ cells and NETs were determined from 5-6 non-overlapping fields per well and the average was taken from duplicates or triplicates for each condition in every experiment. Exposure time for H3Cit and DNA were identical for all treatments within the same experiment. Spread NETs were counted in a single channel for DNA. Images of this channel were exported in black-and-white for better contrast for quantification.

Human Neutrophil Isolation and NETosis Assay.

Blood was drawn from healthy subjects or diabetic patients into EDTA-coated tubes. Neutrophils were isolated using Histopaque®-1119 (Sigma) and Percoll Plus® (GE Healthcare) gradients as described[19], a method that cause minimal activation of neutrophils during isolation. Purity of cells was >95% as determined by Wright-Giemsa staining. For experiments involving high glucose, neutrophils were resuspended in glucose-free HEPES-buffered RPMI supplemented with glucose at 5.5 mM (normal), 22 mM (high) or 5.5 mM plus 16.5 mM mannitol (osmotic control) and 2% heat-inactivated fetal bovine serum. Neutrophils were plated at 10,000 cells/well in 96-well Cellbind® plates (Corning). After incubation in respective media for 1 h, cells were stimulated with ionomycin (4 µM) or PMA (100 nM) for 2.5 hours. For experiments that did not involve high glucose, cells were resuspended in HEPES-buffered RPMI medium (11 mM glucose) supplemented with 2% heat-inactivated fetal bovine serum, plated at 10,000 cells/well and incubated with ionomycin (4 µM) for 2.5 h. Cells were then instantly fixed in 2% PFA with Hoechst 33342 (1:10,000) for NET quantification. Percentage of NETs was determined from 6 non-overlapping fields per well and the average was taken from triplicates for each condition in every experiment. Analysis was performed by an experimenter blinded to treatment conditions.

Wounding and Macroscopic Healing Assessment.

Full-thickness excisional wounds were made on the dorsal skin under aseptic conditions as described[22]. Mice were anesthetized with ketamine and xylazine (100 mg/kg and 10 mg/kg, respectively, i.p.). Hair was removed and the skin was cleaned with 70% ethanol and betadine. A fold of the dorsal skin was then picked up along the midline, placed over dental wax and punched through with a 4-mm disposable sterile biopsy punch (Miltex) such that 2 wounds were generated in one punch. The procedure was repeated, thus 4 wounds were made per mouse. The mice were housed individually after wounding. In experiments involving diabetic mice, all mice were provided ad libitum with antibiotics (2.5% Sulfatrim) in drinking water. Wounds were digitally photographed using a Sony Camcorder and total wound areas were calculated using ImageJ software. Wound area was expressed as a percentage compared to the area on day 0 when the wounds were made.

Western Blot Analysis.

Levels of H3Cit and Ly6G of mouse wounds and PAD4 expression in human neutrophils were quantified by Western blot. After collection of mouse wounds or isolation of human neutrophils, the samples were snap frozen and homogenized in RIPA buffer supplemented with protease inhibitor cocktails (Sigma) on ice. After centrifugation at 20,000 g for 20 min at 4° C., the protein content of the supernatant was determined by bicinchoninic acid protein assay and an equal amount of protein per sample was resolved on gradient gels (4-20%, Lonza) and electrobloted on PVDF membranes, which were then incubated with primary antibodies (rabbit polyclonal anti-H3Cit, 1:1,000, abcam, Cat. no. ab5103; rabbit polyclonal anti-H3, 1:6,000, abcam, Cat. no. ab1791; rat monoclonal anti-mouse Ly6G, 1:500, BD Pharmingen, Cat. no. 551459; mouse monoclonal anti-human PAD4, 1:2,000, abcam, Cat. no. ab128086) at 4° C. overnight and subsequently with appropriate HRP-conjugated secondary antibodies for 2 h at room temperature. The blots were developed with enhanced chemiluminescence substrate. Equal loading was confirmed by probing for GAPDH (1:40,000, Ambion; Cat. no. AM4300). Blots were quantified using ImageJ software.

Immunofluorescence Widefield and Confocal Microscopy.

Localization of H3Cit and neutrophils in the wounds were examined by immunofluorescence microscopy. Wounds were dissected, cut in half and instantly embedded in OCT. The tissue was cryosectioned into 10 µm and 20 µm sections for wide-field and confocal immunofluorescence microscopy, respectively. The sections were post-fixed in zinc fixative (100 mM Tris-HCl, 37 mM zinc chloride, 23 mM zinc acetate, 3.2 mM calcium acetate), permeabilized and incubated with primary antibodies against H3Cit (1:1,000, abcam, Cat. no. ab5103) and Ly6G (1:500, BD Pharmingen, Cat. no. 551459) at 4° C. overnight and then Alexa Fluor-conjugated secondary antibodies (1:1,500, Invitrogen) for 2 hours at room temperature. Hoechst 33342 (1:10,000) was used to stain for DNA. Images were acquired with Zeiss Axiovision software using an Axiovert 200 wide-field fluorescence microscope (Zeiss) coupled to an Axiocam MRm monochromatic CCD camera (Zeiss) or with Olympus Fluoview software using the Olympus IX 81 confocal microscope.

Histological Examination.

Neutrophil recruitment and re-epithelialization were examined in H&E-stained sections. Wounds were cut in half, fixed overnight in zinc fixative and embedded in paraffin. The tissue was sectioned at 10 µm and stained with H&E. Images were acquired with the Zeiss Axiovision software using an Axioplan light microscope coupled to a color Zeiss HRc camera.

Neutrophil Depletion.

Neutrophils of 10-week old WT mice were depleted one day before wounding by i.v. injection of a specific anti-neutrophil antibody (ultra-low endotoxin and azide free rat anti-Ly6G, 1A8 clone, Biolegend, Cat. no. 127632) at a dose of 5 µg/g mouse. Control mice were injected with rat IgG. The mice were re-dosed at 2.5 µg/g mouse 2 days after the first injection. Levels of circulating neutrophils were evaluated by flow cytometry (BD FACSCanto II) using a FITC-conjugated rat monoclonal anti-mouse neutrophil antibody (1:300, anti-7/4, abcam, Cat. no. ab53453) and analyzed using FlowJo software. About 80% of circulating neutrophils were depleted throughout the 3-day wound healing period.

DNase 1 Treatment.

Normoglycemic and diabetic WT mice, randomized by blood glucose levels before assigning to treatments, were injected with 10 µg i.v. and 50 µg i.p. DNase 1 (dornase alfa, Genentech) 30 min before wounding and then 50 µg i.p. every 12 hours until wound collection on day 3. Control mice were injected with vehicle (8.77 mg/mL sodium chloride and 0.15 mg/mL calcium chloride)[40].

Statistical Analysis

Data are presented as mean±s.e.m. of at least two independent experiments, and were analyzed using Mann-Whitney test, two-tailed Student's t-test (unpaired), Kruskal-Willis test followed by Dunn's post test, or repeated measures ANOVA with Bonferroni's post test, where appropriate. Percentage of mice with total wound closure and rate of diabetes induction between WT and PAD4$^{-/-}$ were analyzed with two-tailed Fisher's exact test of contingency tables. Percentage of mice with open wounds was analyzed with the log-rank test after constructing the Kaplan-Meier curves. All analyses were performed using GraphPad Prism software (Version 5.0). Results were considered significant when P<0.05.

NETs were originally recognized as a host defense mechanism in which neutrophils release their nuclear and granular contents to contain and kill pathogens[1]. Bacterial endotoxins, such as lipopolysaccharides (LPS), stimulate the release of NETs[1] that form extensive webs of DNA coated with cytotoxic histones and microbicidal proteases[1,2]. A prerequisite for NETosis is modification of arginine residues of histones to citrulline by PAD4, which changes the charge of the histones, leading to massive chromatin decondensation[3,4]. Recently it became evident that NETs also form during sterile inflammation[5]. NETs are a key scaffold in pathologic thrombi and fuel cardiovascular, inflammatory and thrombotic diseases in mice and humans[5,6].

Figure 1B:
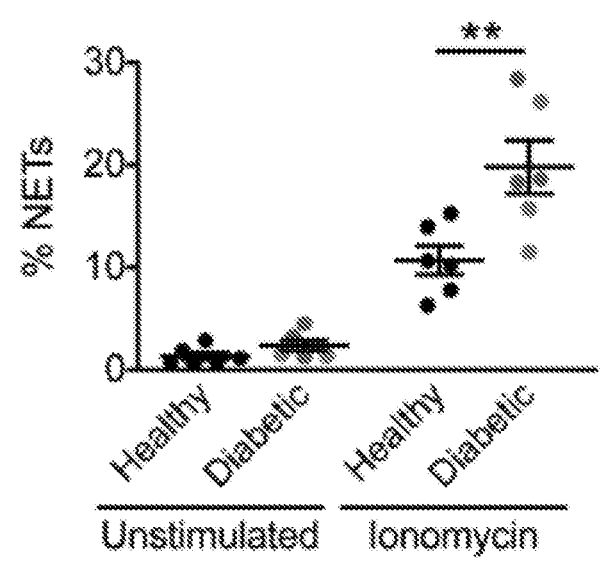
Figure 1C:
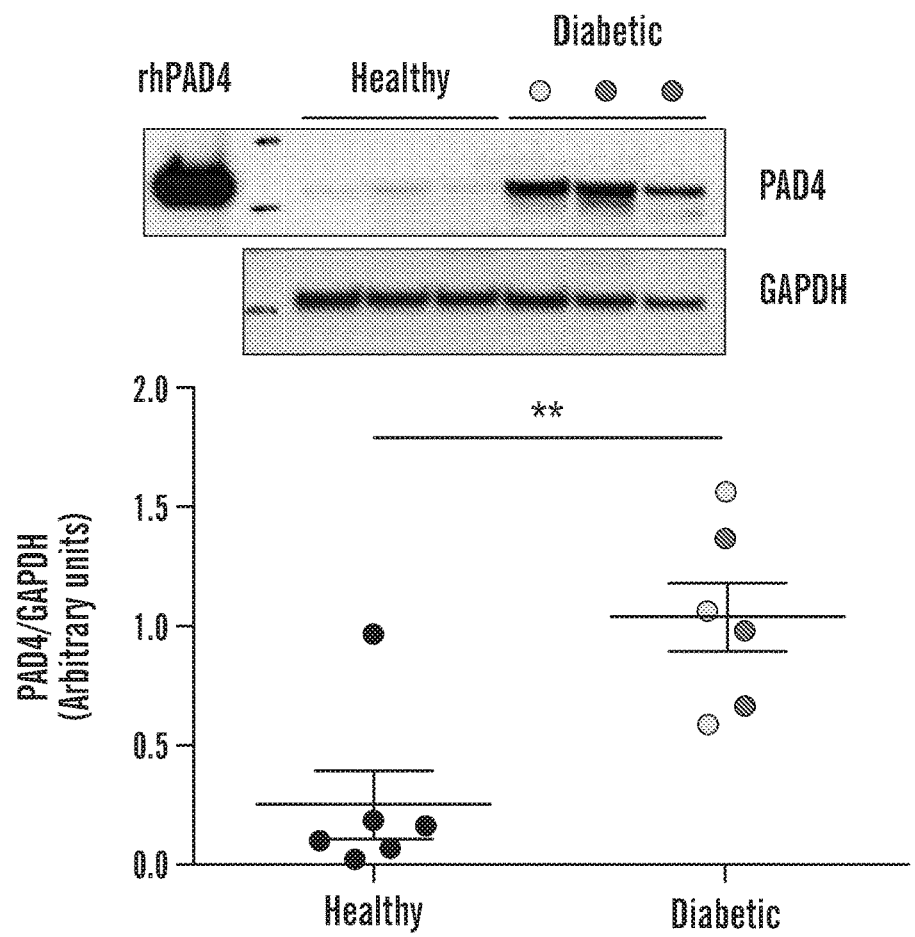

Under diabetic conditions, neutrophils produce more superoxide[7] and cytokines[8]. Tumor necrosis factor-α, which primes neutrophils for NETosis[9,10], is increased in diabetic patients[11]. The diabetic microenvironment is thus pro-NETotic. To test whether diabetes predisposes neutrophils to NETosis, we isolated neutrophils from the fresh whole blood obtained from both type 1 and type 2 diabetic patients whose glycated hemoglobin (HbA1c) was >6.5%, indicating mild prolonged hyperglycemia (FIG. 1a). Neutrophils from these patients were indeed more susceptible to NETosis when stimulated with the calcium ionophore, ionomycin (FIG. 1b). PAD4 is a calcium-dependent enzyme[12] that is key in mediating NETosis[13]. Western blotting revealed a 4-fold upregulation of PAD4 protein expression in the neutrophils from diabetic patients (FIG. 1c), which may explain their higher susceptibility to NET formation. Our present findings are complemented by a recent report showing that circulating NET-related biomarkers, nucleosomes, cell-free double-strand DNA and neutrophil elastase, are increased in type 2 diabetic patients' serum, and that nucleosomes positively correlate with the patients' HbA1c levels[14].

Figure 1D:
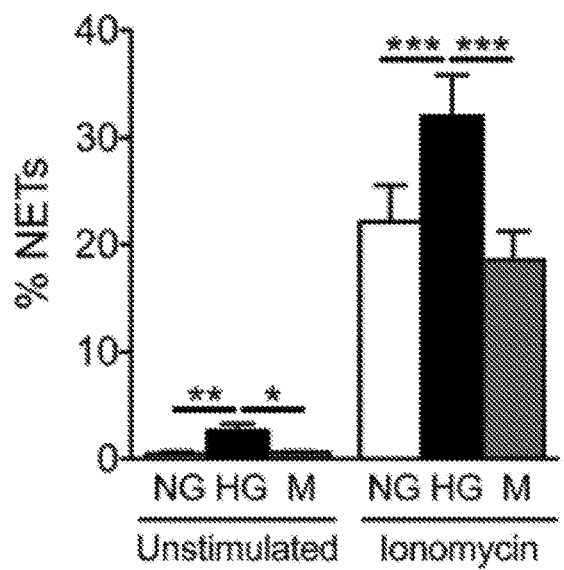

Because hyperglycemia is common to both type 1 and type 2 diabetes, as indicated by the significantly higher HbA1c in the diabetic cohort compared to the healthy controls (FIG. 1a, [Table 1]), we hypothesized that high glucose may contribute to neutrophil priming. We therefore isolated neutrophils from healthy donors and pre-incubated them in media with normal or high glucose concentrations prior to stimulation with ionomycin or phorbol 12-myristate 13-acetate (PMA) which triggers production of reactive oxygen species (ROS). Both ionomycin and PMA stimulated more of the high glucose-exposed neutrophils to produce NETs compared to pre-incubation with normal glucose or equal concentrations of the non-metabolizable sugar alcohol, mannitol (FIG. 1d, and data not shown). Thus, the increased susceptibility of diabetic neutrophils to NETosis is at least in part due to elevations in blood glucose. Our observations differ from earlier reports[15,16] which suggested that high glucose/diabetes does not affect or impairs NETosis. This difference is likely due to the pre-activation of human neutrophils during isolation with dextran sedimentation, a method that can induce ROS production and NET formation[17,18] prior to culture, which could result in the loss of the primed neutrophil population during the preparatory process in the previous studies. Using Histopaque/Percoll gradients for human neutrophil isolation[19], we found a clear priming effect by diabetes or high glucose on NETosis.

TABLE 1

Parameters of healthy subjects and diabetic patients

| | Healthy Subjects | Diabetic Patients |
|---|---|---|
| Age (years) | 36 ± 6 | 40 ± 6 |
| Leukocyte count (K/µL) | 6.00 ± 0.70 | 6.58 ± 1.07 |
| Platelet count (K/µL) | 299.20 ± 20.00 | 276.20 ± 12.20 |
| HbA1c (%) | 5.62 ± 0.08 | 8.35 ± 0.61 ** |
| Glucose (mg/dL) | 88.50 ± 3.13 | 134.20 ± 21.67 (a) |
| Cholesterol (mg/dL) | 178.30 ± 16.28 | 179.50 ± 16.07 |

TABLE 1-continued

Parameters of healthy subjects and diabetic patients

|  | Healthy Subjects | Diabetic Patients |
|---|---|---|
| Triglycerides (mg/dL) | 102.30 ± 26.24 | 259.20 ± 97.35 |
| HDL (mg/dL) | 72.50 ± 14.31 | 54.67 ± 11.79 |
| LDL (mg/dL) | 86.17 ± 9.01 | 97.83 ± 16.00 |

** $P < 0.01$,
(a) $P = 0.0542$ versus healthy subjects

Figure 1H:
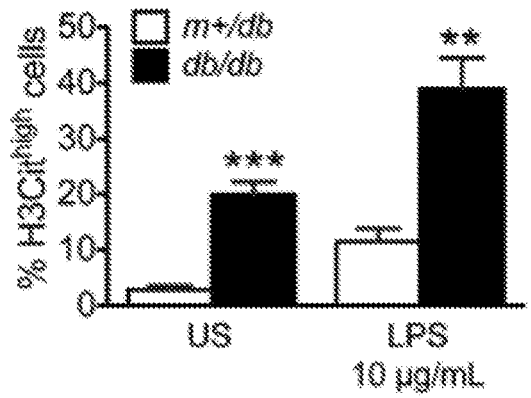
Figure 1I:
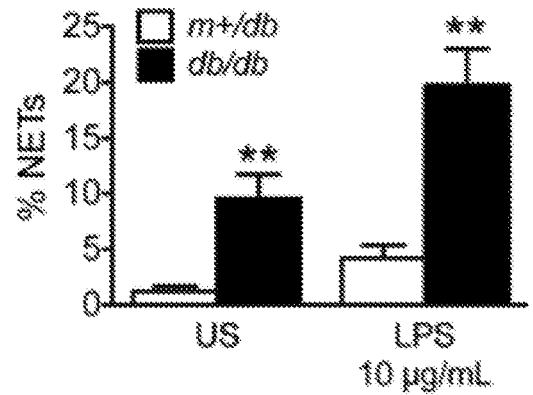
Figure 1J:
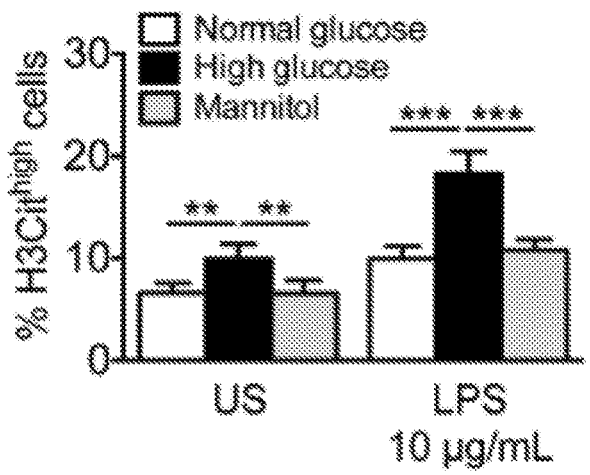
Figure 1K:
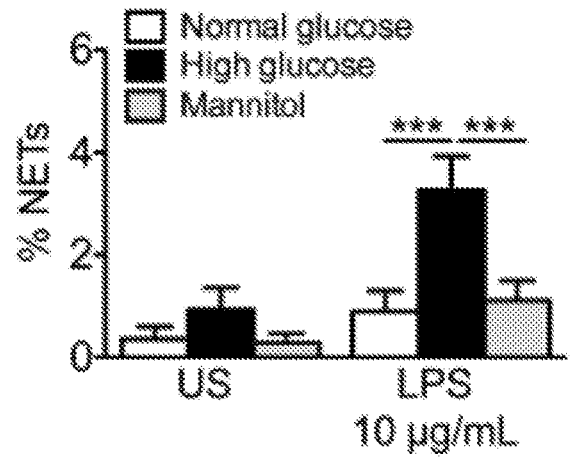

We then examined the susceptibility to NETosis in diabetic mouse models, which are amenable to experimentation needed to study the role of PAD4 and impact of NETs on diabetic wound healing. Immunostaining of fresh blood cells from streptozotocin (STZ)-induced diabetic mice (a model of type 1 diabetes) (data not shown) revealed a ~4 fold increase in neutrophils positive for citrullinated histone H3 (H3Cit), a biomarker of NETosis, compared to normoglycemic mice (data not shown). About 4.5 fold more isolated neutrophils from diabetic mice were H3Cit$^{high}$ (FIG. 1e) and ~2% produced NETs after incubation in vitro without stimulation, while <0.2% NETs were seen in the normoglycemic controls (FIG. 1f). LPS further stimulated more neutrophils from the STZ-induced diabetic mice to be H3Cit$^{high}$ (FIG. 1e, FIG. 1g) and form NETs (FIG. 1f, FIG. 1g) compared to vehicle-treated normoglycemic mice. Thus, similar to humans, diabetes has inflammatory or metabolic components that predispose mouse neutrophils to NETosis. Although there is no specific anti-mouse PAD4 antibody to evaluate whether PAD4 protein expression is increased by diabetes, neutrophil priming could be also attributable to an increased PAD4 activity as indicated by elevated histone H3 citrullination[4] (FIG. 1e, data not shown). Similar NETosis assays were performed with neutrophils from genetically modified db/db mice (data not shown), a type 2 diabetic model. These neutrophils were also predisposed to hypercitrullinate histone H3 and form NETs (FIG. 1h, FIG. 1i) when compared to the neutrophils from normoglycemic control m+/db mice, indicating enhanced NETosis is a common phenomenon in murine diabetes regardless of the type or etiology as we observed in the human condition. LPS again stimulated more of the high glucose-exposed neutrophils from normoglycemic WT mice to histone hypercitrullination (FIG. 1j) and NET production (FIG. 1k), indicating a possible priming role of high glucose. Thus the mouse models of diabetes represent well the human condition in respect to susceptibility to NETosis and induction of PAD4 activity.

Figure 2A:
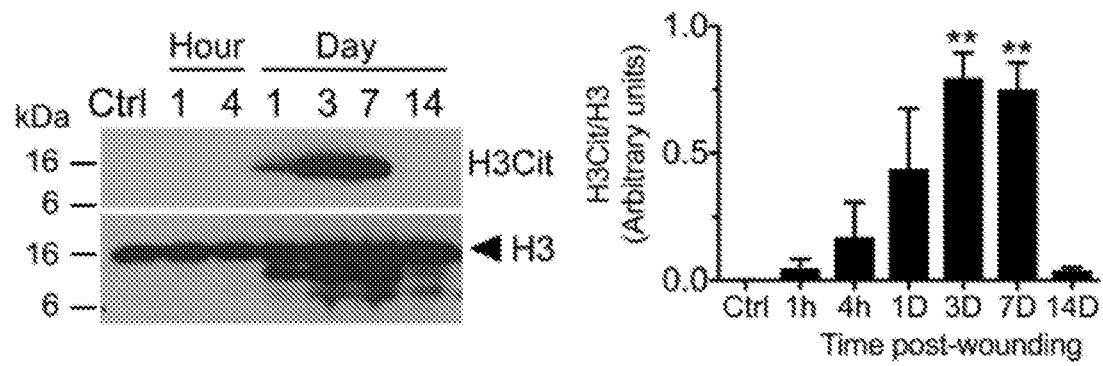
FIGS. 2a to 2b are Western blot and graphs illustrating that neutrophil H3Cit and extracellular chromatin are observed in the wounds of WT mice, indicating the formation of NETs.
Figure 2B:
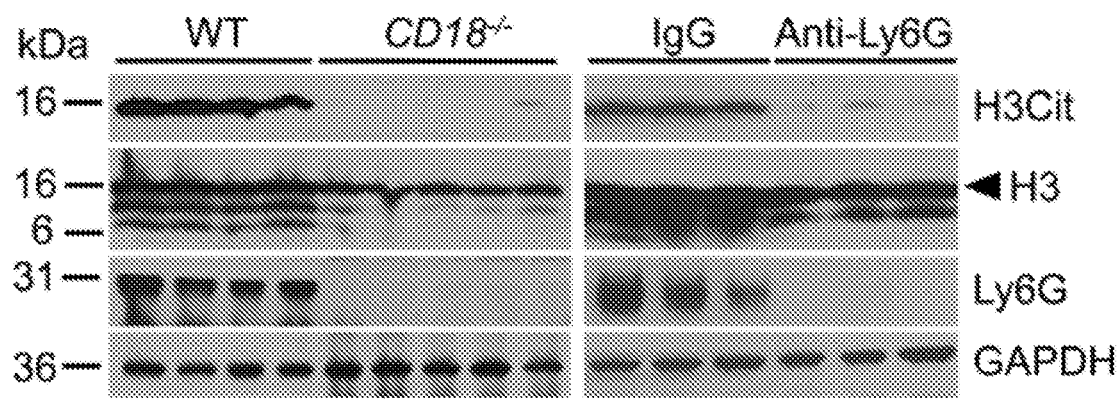

Depletion of neutrophils in mice was previously shown to accelerate re-epithelialization of uninfected diabetic wounds[20]. Because NETs can be injurious to tissues[21], we asked whether NETs form in wounds and impact healing. We examined excisional wounds[22] from normoglycemic WT mice. H&E staining confirmed that recruitment of leukocytes, mainly neutrophils, overlaps with the keratinocyte proliferation stage that leads to re-epithelialization (data not shown). Therefore, neutrophils or NETs could interfere with healing. Analysis of wound proteins by Western blotting showed a progressively increasing level of H3Cit that peaked from 3 to 7 days after wounding (FIG. 2a). Immunofluorescence images of 3-day wounds showed that hypercitrullinated neutrophils were present in the wound bed immediately beneath the scab (data not shown). Confocal microscopy substantiated the presence of NETs in skin wounds. Externalized DNA colocalized with H3Cit in areas associated with intense staining of the neutrophil membrane marker, Ly6G (data not shown). Of note, H3Cit and neutrophils were absent in the surface layers of unwounded skin (data not shown). Skin expresses PAD isoforms 1-3[23] which could citrullinate extracellular proteins in the scab. To verify the cellular source of H3Cit, we subjected CD 18 (132 integrin)-deficient (CD18$^{-/-}$) mice, which are defective in leukocyte recruitment, to wounding. In these mice, both H3Cit and Ly6G were undetectable by Western blotting in 3-day wounds (FIG. 2b, left panels), a time when H3Cit was maximal in the WT wounds (FIG. 2a), indicating that H3Cit is of leukocyte origin. H&E staining and immunofluorescence microscopy showed that the few CD18$^{-/-}$ neutrophils present in these wounds were H3Cit+ and produced NETs (data not shown). Indeed, CD18$^{-/-}$ neutrophils produced NETs efficiently in vitro (data not shown), showing that 132 integrins were not required for NETosis. Wounds from WT mice with depleted neutrophils also showed markedly reduced H3Cit (FIG. 2b, right panels). Thus, our data indicate that neutrophils are the source of the H3Cit present in the wounds.

Figure 3A:
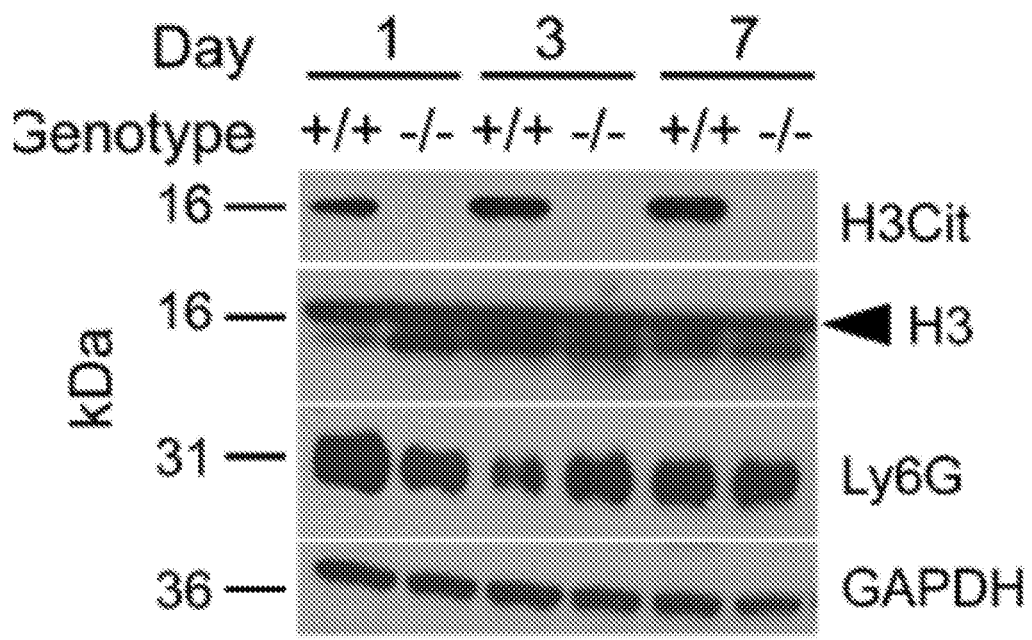
FIGS. 3a to 3e indicate that PAD4 deficiency facilitates wound repair in normoglycemic mice.
Figure 3B:
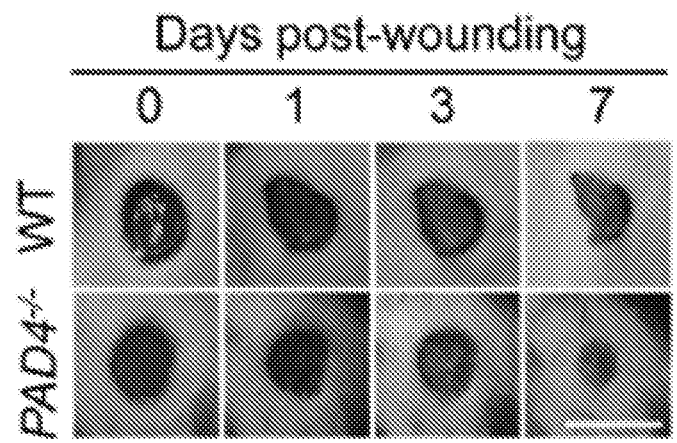
Figure 3C:
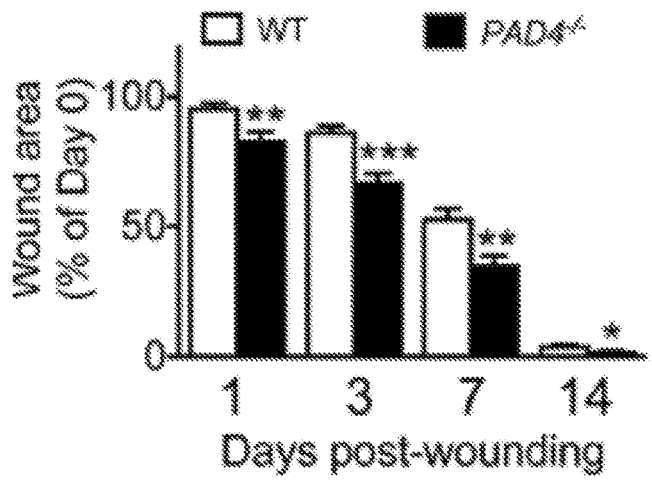
Figure 3D:
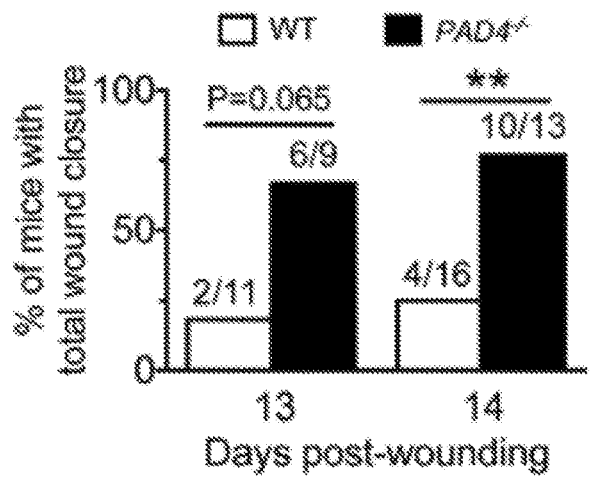
Figure 3E:
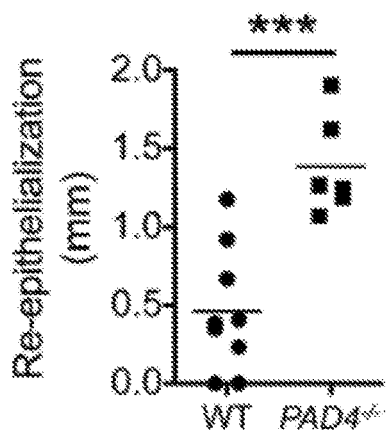

To establish the role of NETs in wound healing, we compared wounds of WT to PAD4$^{-/-}$ mice. Prominent extracellular DNA structures observed by H&E were absent in PAD4$^{-/-}$ scabs (data not shown), as were the H3Cit and extracellular chromatin patterns seen in WT mice by confocal microscopy (data not shown). In contrast to the robust H3Cit signals in WT wounds, no H3Cit was detected in wounds from PAD4$^{-/-}$ mice despite normal neutrophil recruitment (FIG. 3a and data not shown). Unlike neutrophil recruitment-defective P-/E-selectin double mutants that have opportunistic infections[24] and impaired wound healing[22], wounds in PAD4$^{-/-}$ mice did not show overt signs of infection (FIG. 3b) and healed faster than WT (FIG. 3b, FIG. 3c). This is likely because other neutrophil functions such as phagocytosis[13], degranulation and ROS production (our unpublished observations) are intact in PAD4$^{-/-}$ neutrophils so that these neutrophils are fully capable of performing other host defense mechanisms. About 80% of PAD4$^{-/-}$ mice had all wounds healed on day 14 compared to only 25% of WT controls (FIG. 3d). The beneficial effect of PAD4 deficiency on wound healing was observed very early after injury (FIG. 3c), indicating that NETs might impair the onset of initial healing processes such as keratinocyte migration. In line with this hypothesis, re-epithelialization progressed 3-fold faster in PAD4$^{-/-}$ mice compared to WT (FIG. 3e, and data not shown). Immunofluorescence staining of Ki67 (a proliferation marker) and TUNEL (indicator of apoptosis) was not different between 3-day wounds from WT and PAD4$^{-/-}$ mice (data not shown). It is thus likely that migration per se is affected, perhaps due to a modification of matrix proteins induced by NETs. Although WT and PAD4$^{-/-}$ neutrophils also express PAD2 and PAD3[13], our data demonstrate that PAD4, the only nuclear PAD, is essential for the histone H3 citrullination and NETosis in skin wounds. Coudane et al.[25] reported that PAD4 is the main PAD isoform detected in scabs of wounds from WT mice, and that PAD2 is unnecessary for citrullination of scab proteins as observed in PAD2-deficient mice, further strengthening the unique deimination role of PAD4 in the wounds.

We next examined whether NETs interfere with diabetic wound healing. Type 1 diabetes was induced in WT and PAD4$^{-/-}$ mice by STZ and 8 weeks later these mice were subjected to wounding. Changes in body weight, fed blood glucose and diabetes induction rate were similar between the two genotypes (FIG. 9d-f). As expected, diabetic WT mice healed more slowly than normoglycemic controls (FIG. 4a).

Figure 10A:
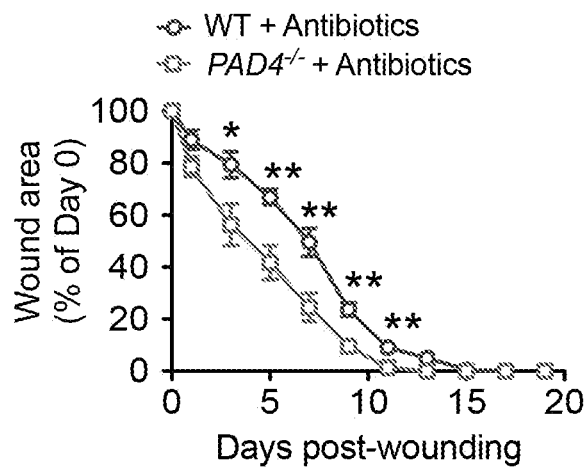
FIGS. 10a to 10b are graphs of wound healing over time. Antibiotics do not abrogate the beneficial effect of PAD4 deficiency on wound healing. Under antibiotic treatment, PAD4$^{-/-}$ mice still fared better in terms of (FIG. 10a) wound area reduction and (FIG. 10b) days required for total wound closure. *P<0.05, **P<0.01 between groups on the same day or between curves, Student's t test, n=7 for WT Vehicle, n=5 for PAD4$^{-/-}$ Vehicle.
Figure 10B:
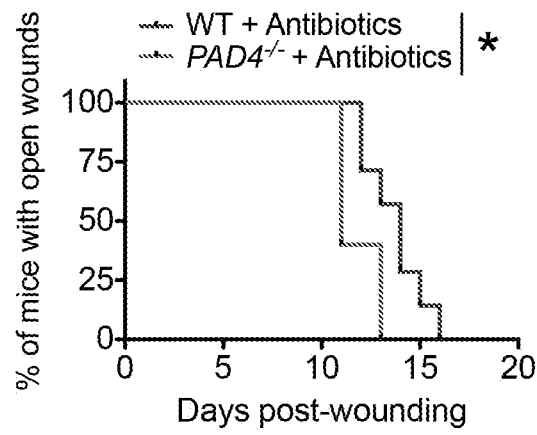
Figure 11:
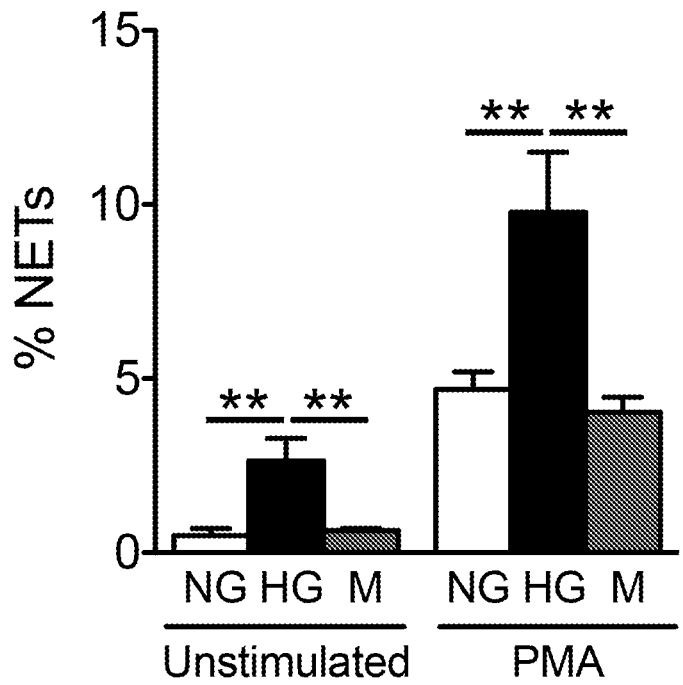
FIG. 11 shows a graph of percent NETS. High glucose (HG) enhances PMA (100 nM)-stimulated NET formation in neutrophils isolated from healthy subjects compared to neutrophils exposed to normal glucose (NG) medium or mannitol (M), osmotic control. **P<0.01, repeated measures ANOVA, n=5 per condition.
Figures 12A, 12B:
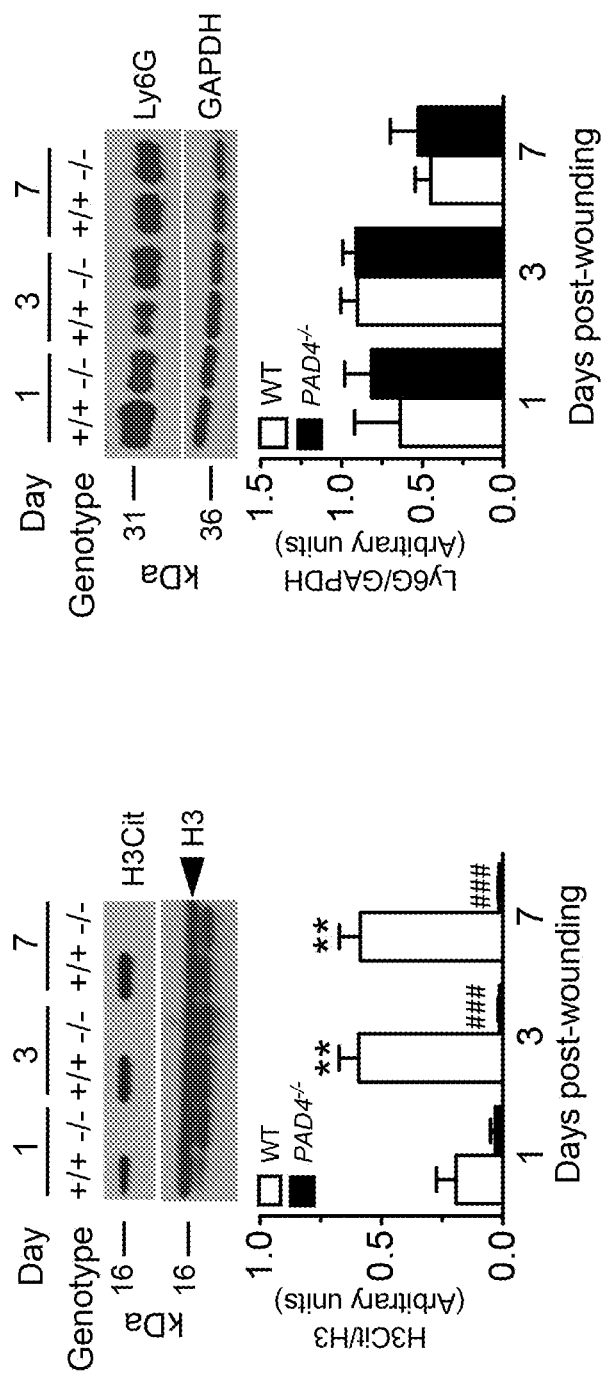
FIGS. 12a and 12b are Western blots and quantitative graphs indicating H3Cit (FIG. 12a) is absent while neutrophil recruitment (FIG. 12b) is unaffected in wounds of PAD4$^{-/-}$ mice. Summarized Western blot data of FIG. 3a+/+, WT; −/−, PAD4$^{-/-}$. **P<0.01 versus day 1 WT, #### P<0.001 versus WT on respective day, Student's t test, n=5-8 for WT, n=5-9 for PAD4$^{-/-}$.

All normoglycemic WT mice healed by day 16, while ~20% of diabetic mice still had open wounds on day 19 (FIG. 4d). Diabetic PAD4$^{-/-}$ mice healed >3 5% faster than diabetic WT mice on day 7 (FIG. 4b) and had all wounds closed by day 15 (FIG. 4e). Notably, diabetes did not impair wound healing in PAD4$^{-/-}$ mice (FIG. 4c,f), which underscores NETs as the major determinant delaying healing in the diabetic mice. Higher H3Cit levels were detected in wounds of STZ-induced diabetic mice compared to the normoglycemic WT mice 1 day post wounding (FIG. 4g). The enhanced NETosis in vivo recapitulates our in vitro observations (FIG. 1e-g), further supporting the role of NETs in the delay in diabetic wound repair. Antibiotics, provided to mimic the medical regimen of diabetic patients with chronic wounds, did not abolish the beneficial effect of PAD4 deficiency ([Supplementary FIG. 10]).

Enhanced wound healing in PAD4$^{-/-}$ mice suggests that NETs may be a redundant host defense mechanism that compromises wound repair. NETs and histones directly induce epithelial and endothelial cell death[21], and cause cytotoxicity in vitro and in vivo via calcium influx[26]. High neutrophil elastase concentration, a component of NETs[1,2], can cause degradation of the wound matrix and delay healing[27]. Such a cytotoxic environment produced by NETs may explain the slower keratinocyte repopulation in the wound beds of WT mice. Because PAD4 is not expressed in the skin[23], its negative effect on wound healing is most likely due to infiltrating neutrophils. In fact, using NETs to defend against microbes may not be very effective during wound healing as *Staphylococcus* species, which are very abundant in diabetic wounds[28], degrade NETs to escape trapping[29], and the NET degradation products can affect the proper healing process[30,31]. Thus, the non-selective cytotoxicity of NETs and/or their degradation products resulting from bacterial infection may profoundly delay wound healing.

Farrera and Fadeel reported that pre-digestion of NETs with DNase 1 accelerated their clearance by macrophages in vitro[32]. Facilitated clearance of NETs in wounds may reduce their toxicity and diminish wound matrix degradation that is essential for the directional migration of keratinocytes[33]. We thus tested whether systemic DNase 1 treatment could accelerate wound healing in diabetic mice that were maintained on antibiotics. Without DNase 1 treatment, diabetic PAD4$^{-/-}$ mice healed better in terms of both a greater reduction in wound area (FIG. 4h, upper panel) and more re-epithelialization (FIG. 4h, lower panel) compared to the diabetic WT mice as examined on day 3 post wounding. Administration of DNase 1 promoted wound area reduction by >20% and enhanced re-epithelialization by >75% in diabetic WT mice, an extent similar to that of DNase 1-treated normoglycemic WT mice (FIG. 4h). Interestingly, DNase 1 treatment did not provide further benefits in healing the wounds of diabetic PAD4$^{-/-}$ mice (FIG. 4h). These data indicate that NETs are the major source of extracellular DNA that hinders wound healing. Such beneficial effects of DNase 1 were not confined to diabetic wounds. Three days post wounding, wound areas in normoglycemic mice treated with DNase 1 were smaller than in those treated with vehicle (FIG. 4i, upper panel). Re-epithelialization was also enhanced by ~54% in the DNase 1-treated group (FIG. 4i, lower panel), while neutrophil recruitment was not affected (data not shown). Our current findings corroborate positive results from pilot clinical trials with activated protein C (APC), which cleaves and reduces the cytotoxicity of histones[34] and facilitates healing of chronic wounds[35] and diabetic ulcers[36]. Topical treatment with an ointment containing fibrinolysin and DNase (Elase) is used clinically for wound debridement. In addition to removing necrotic tissue, our findings suggest that the DNase component may also cleave NETs to reduce cytotoxicity and enhance wound recovery.

In summary, our data demonstrate that diabetes activates neutrophils to overproduce PAD4 and NETs and identify NETs as a key factor delaying wound healing. PAD4 inhibition and cleavage of NETs by DNase 1 could be novel therapeutic approaches to wound resolution, not only in diabetes, but also to wounds resulting from aseptic procedures such as surgeries of normoglycemic patients. We further validate the importance of PAD4 in human disease, and report the upregulation of PAD4 in diabetic patients, thus providing new rationale to develop specific PAD4 inhibitors. Because PAD4 and NET formation contribute to inflammatory and thrombotic diseases[5,6] that are prominent in diabetics[37,38], anti-NET therapy could have additional benefits. The increased NETosis in diabetes suggests that NETs may fuel these disorders and inhibiting NETosis or cleavage of NETs may lessen them.

Example 1 References

1. Brinkmann, V., et al. Neutrophil extracellular traps kill bacteria. Science 303, 1532-1535 (2004)
2. Urban, C. F., et al. Neutrophil extracellular traps contain calprotectin, a cytosolic protein complex involved in host defense against Candida albicans. PLoS Pathog 5, e1000639 (2009).
3. Wang, Y., et al. Histone hypercitrullination mediates chromatin decondensation and neutrophil extracellular trap formation. J Cell Biol 184, 205-213 (2009).
4. Wang, Y., et al. Human PAD4 regulates histone arginine methylation levels via demethylimination. Science 306, 279-283 (2004).
5. Yipp, B. G. & Kubes, P. NETosis: how vital is it? Blood 122, 2784-2794 (2013).
6. Martinod, K. & Wagner, D. D. Thrombosis: tangled up in NETs. Blood 123, 2768-2776 (2014).
7. Karima, M., et al. Enhanced superoxide release and elevated protein kinase C activity in neutrophils from diabetic patients: association with periodontitis. J Leukoc Biol 78, 862-870 (2005).
8. Hanses, F., Park, S., Rich, J. & Lee, J. C. Reduced neutrophil apoptosis in diabetic mice during staphylococcal infection leads to prolonged TNF-? production and reduced neutrophil clearance. PLoS One 6, e23633 (2011).
9. Khandpur, R., et al. NETs are a source of citrullinated autoantigens and stimulate inflammatory responses in rheumatoid arthritis. Sci Transl Med 5, 178ra140 (2013).
10. Thomas, G. M., et al. Extracellular DNA traps are associated with the pathogenesis of TRALI in humans and mice. Blood 119, 6335-6343 (2012).
11. Alexandraki, K. I., et al. Cytokine secretion in longstanding diabetes mellitus type 1 and 2: associations with low-grade systemic inflammation. J Clin Immunol 28, 314-321 (2008).
12. Luo, Y., et al. Inhibitors and inactivators of protein arginine deiminase 4: functional and structural characterization. Biochemistry 45, 11727-11736 (2006).
13. Li, P., et al. PAD4 is essential for antibacterial innate immunity mediated by neutrophil extracellular traps. J Exp Med 207, 1853-1862 (2010).

14. Menegazzo, L., et al. NETosis is induced by high glucose and associated with type 2 diabetes. Acta Diabetol (2014). [epub ahead of print]
15. Joshi, M. B., et al. High glucose modulates IL-6 mediated immune homeostasis through impeding neutrophil extracellular trap formation. FEBS Lett 587, 2241-2246 (2013).
16. Riyapa, D., et al. Neutrophil extracellular traps exhibit antibacterial activity against *Burkholderia pseudomallei* and are influenced by bacterial and host factors. Infect Immun 80, 3921-3929 (2012).
17. Fuchs, T. A., et al. Novel cell death program leads to neutrophil extracellular traps. J Cell Biol 176, 231-241 (2007).
18. Rebecchi, I. M., Ferreira Novo, N., Julian, Y. & Campa, A. Oxidative metabolism and release of myeloperoxidase from polymorphonuclear leukocytes obtained from blood sedimentation in a Ficoll-Hypaque gradient. Cell Biochem Funct 18, 127-132 (2000).
19. Brinkmann, V., Laube, B., Abu Abed, U., Goosmann, C. & Zychlinsky, A. Neutrophil extracellular traps: how to generate and visualize them. J Vis Exp (2010).
20. Dovi, J. V., He, L. K. & DiPietro, L. A. Accelerated wound closure in neutrophil-depleted mice. J Leukoc Biol 73, 448-455 (2003).
21. Saffarzadeh, M., et al. Neutrophil extracellular traps directly induce epithelial and endothelial cell death: a predominant role of histones. PLoS One 7, e32366 (2012).
22. Subramaniam, M., et al. Role of endothelial selectins in wound repair. Am J Pathol 150, 1701-1709 (1997).
23. Nachat, R., et al. Peptidylarginine deiminase isoforms 1-3 are expressed in the epidermis and involved in the deimination of K1 and filaggrin. J Invest Dermatol 124, 384-393 (2005).
24. Frenette, P. S., Mayadas, T. N., Rayburn, H., Hynes, R. O. & Wagner, D. D.
Susceptibility to infection and altered hematopoiesis in mice deficient in both P- and E-selectins. Cell 84, 563-574 (1996).
25. Coudane, F., et al. Deimination and expression of peptidylarginine deiminases during cutaneous wound healing in mice. Eur J Dermatol 21, 376-384 (2011).
26. Abrams, S. T., et al. Circulating histones are mediators of trauma-associated lung injury. Am J Respir Crit Care Med 187, 160-169 (2013).
27. Herrick, S., et al. Up-regulation of elastase in acute wounds of healthy aged humans and chronic venous leg ulcers are associated with matrix degradation. Lab Invest 77, 281288 (1997).
28. Grice, E. A., et al. Longitudinal shift in diabetic wound microbiota correlates with prolonged skin defense response. Proc Natl Acad Sci USA 107, 14799-14804 (2010).
29. Berends, E. T., et al. Nuclease expression by *Staphylococcus aureus* facilitates escape from neutrophil extracellular traps. J Innate Immun 2, 576-586 (2010).
30. Thammavongsa, V., Missiakas, D. M. & Schneewind, O. *Staphylococcus aureus* degrades neutrophil extracellular traps to promote immune cell death. Science 342, 863866 (2013).
31. Ishida, Y., Gao, J. L. & Murphy, P. M. Chemokine receptor CX3CR1 mediates skin wound healing by promoting macrophage and fibroblast accumulation and function. J Immunol 180, 569-579 (2008).
32. Farrera, C. & Fadeel, B. Macrophage clearance of neutrophil extracellular traps is a silent process. J Immunol 191, 2647-2656 (2013).
33. Pilcher, B. K., et al. The activity of collagenase-1 is required for keratinocyte migration on a type I collagen matrix. J Cell Biol 137, 1445-1457 (1997).
34. Xu, J., et al. Extracellular histones are major mediators of death in sepsis. Nat Med 15, 1318-1321 (2009).
35. Whitmont, K., et al. Treatment of chronic leg ulcers with topical activated protein C. Arch Dermatol 144, 1479-1483 (2008).
36. Whitmont, K., et al. Treatment of chronic diabetic lower leg ulcers with activated protein C: a randomised placebo-controlled, double-blind pilot clinical trial. Int Wound J (2013).
37. Laakso, M. & Kuusisto, J. Insulin resistance and hyperglycaemia in cardiovascular disease development. Nat Rev Endocrinol 10, 293-302 (2014).
38. Morel, O., Jesel, L., Abbas, M. & Morel, N. Prothrombotic changes in diabetes mellitus. Semin Thromb Hemost 39, 477-488 (2013).
39. Demers, M., et al. Cancers predispose neutrophils to release extracellular DNA traps that contribute to cancer-associated thrombosis. Proc Natl Acad Sci USA 109, 13076-13081 (2012).
40. Brill, A., et al. Neutrophil extracellular traps promote deep vein thrombosis in mice. J Thromb Haemost 10, 136-144 (2012).

Example 2: PAD4 Promotes Fibrosis

Methods
Animals.
Twenty-four to 27-month-old C57BL/6 mice for in vitro NETosis studies were obtained from the Aged Rodent Colony of the National Institute on Aging of the National Institutes of Health, maintained at Charles River Laboratories. Young mice (8-16 weeks old) for these experiments were obtained from the same colony.

$PAD4^{-/-}$ and corresponding wild-type (WT) mice were on a C57BL/6J background. Retired breeders had been kept on LabDiet PicoLab Mouse Diet 20, which is fortified with a higher fat content for growth and reproduction (21.635% calories provided by fat), from 6-10 weeks of age until the time of sacrifice. Non-breeders and all young mice were kept on a standard laboratory diet (LabDiet Prolab IsoPro RMH 3000, 14.276% calories provided by fat) throughout their life. Young animals were 6-8 weeks, retired breeders were 12-17 months old and old mice that had been kept on standard lab diet were 14-18 months old. Old mice for the diastolic measurements were 18 months old for the $PAD4^{-/-}$ mice and between 15 and 20 months old for the old WT mice, while young mice in this experiment were 8 weeks old.

All groups were age and sex matched, and were fed ad libitum with free access to water. All experimental procedures were reviewed and approved by the Institutional Animal Care and Use Committee of Boston Children's Hospital (protocol no. 14-03-2631R).

Analysis of Peripheral Blood and Cytospin.
Blood was collected from anesthetized mice via the retroorbital sinus into EDTA-coated capillary tubes and was analyzed by a Hemavet 950FS (Drew Scientific) for complete blood counts.

Twenty-five microliters of whole blood was incubated in ACK (ammonium chloride potassium) lysis buffer for 10 min on ice, then cytocentrifuged using a Statspin Cytofuge 2. Samples were immediately fixed in 4% paraformaldehyde for 2 h at room temperature and then immunostained for H3Cit and Ly6G as previously described (16). Images were acquired of cells from 10-15 fields of view at 200× magnification using a Zeiss Axiovert inverted epifluorescence microscope and Zeiss Axiovision software. Thresholding analysis was performed using ImageJ software to calculate the population of H3Cit-positive neutrophils in each sample.

Peripheral Blood Neutrophil Isolation and NET Induction.

Peripheral blood neutrophils were isolated as described (16) and stimulated with calcium ionophore (4 µM) or PMA (100 nM) for 3.5 h. Cells were fixed with 2% (vol/vol) paraformaldehyde, and DNA was stained with Hoechst 33342 (Invitrogen) for visualization of NETs using an epifluorescent Axiovert microscope (Zeiss). NETs were counted from five distinct fields of view in triplicate wells and expressed as percentage of NET-forming cells per total number of cells in the field.

Plasma Collection.

Blood was collected from the retroorbital plexus of anesthetized mice (using 3.5% isoflurane) into sodium citrate anticoagulant (10% vol/vol). Whole blood was centrifuged at 6000 rpm for 5 min, plasma was collected and again centrifuged at 13200 rpm for 5 min to remove any remaining cellular components. Plasma samples were immediately stored at −80° C. until analysis.

Echocardiography.

Cardiac function and heart dimensions were measured as described (11). The M-mode was used to evaluate left ventricular (LV) internal dimension (LVID), LV interventricular septum (LVIS), and LV posterior wall thickness (LVPW) at end diastole and end systole. Echocardiograms were stored digitally and ejection fraction (LVEF; percentage) was calculated using Vevostrain software (VisualSonics). Flow pattern across the mitral valve was measured in the 4-chamber view using the Pulsed Wave (PW) Doppler mode to determine evidence of impaired ventricular relaxation. Ventricular filling pattern is expressed as the ratio between the E and the A wave (E/A).

Blood Pressure Measurements.

Systolic blood pressure was measured using a IITC 12M22931 non-invasive blood pressure system (IITC Life Science). Mice were trained twice several days before the measurements to accustom them to measurement conditions. For measurements, the mice were placed into restrainers and allowed to settle down for 10 min. Systolic blood pressure was determined by the tail cuff in a chamber at 34° C. Blood pressure was measured 5 times, and the mean of the obtained values is presented (Table 2).

TABLE 2

| | WT | PAD4$^{-/-}$ | P-value |
|---|---|---|---|
| Total leukocytes (×103/µl) | 7.902 ± 1.033, n = 9 | 9.068 ± 1.123, n = 8 | 0.4174 |
| Neutrophils (×10$^3$/µl) | 1.762 ± 0.276, n = 9 | 2.285 ± 0.373, n = 8 | 0.1662 |
| Platelets (×10$^6$/µl) | 1062 ± 43.67, n = 9 | 1002 ± 38.42, n = 8 | 0.5240 |
| Weights (g) | 39.70 ± 1.283, n = 10 | 36.43 ± 1.525, n = 7 | 0.0951 |
| Blood pressure (mm Hg) | 93.38 ± 1.590, n = 9 | 95.48 ± 2.953, n = 10 | 0.6464 |

Tissue Preparation and Analysis.

Anesthetized mice were sacrificed by cervical dislocation, lungs and hearts removed and preserved in 10% neutral buffered formalin solution for at least 24 h. Organs were embedded in paraffin, sectioned and rehydrated. To assess collagen content in heart tissue, Sirius red staining solution was prepared with 0.5 g Direct Red 80 (Sigma) powder in 500 ml of saturated aqueous solution of picric acid (Sigma). Sirius red stains collagen I, II and III by reacting, via its sulphonic acid groups, with basic groups of the collagen molecule (32). Slides were stained for 60 min, washed twice in acidified water (5% v/v acetic acid), dehydrated and mounted using a resinous mounting medium. At least 5 photographs of left ventricular heart tissue were taken at 250× magnification in brightfield microscopy in a blinded manner. The content of red fibers (collagen) per section was determined using ImageJ software, and perivascular fibrosis was excluded from the calculation. A subset of slides was stained with Weigert's hematoxylin before Sirius red staining and was used for the generation of representative pictures of heart tissue. For quantification, slides without nuclear staining were used to avoid interference of hematoxylin with the quantification algorithm. Mosaics of representative areas of the left ventricle were generated using the MosaicJ plugin of ImageJ (33). For trichrome staining of lung tissue the Masson trichrome stain kit (Sigma) was used according to the manufacturer's protocol. Nuclei were not stained with hematoxylin to avoid interference with the quantification of collagen content. For quantification, at least 6 photographs of lung parenchyma were taken by brightfield microscopy by an investigator blinded to the identity of the samples. The area of blue fibers (collagen) per lung tissue (excluding empty alveolar spaces) was calculated using ImageJ software. Staining of heart tissue by trichrome stain was carried out in parallel. As these latter slides were not used for quantification, nuclei were stained using Weigert's hematoxylin.

Statistical Analysis.

Data are presented as means±SEM. For statistical tests, a two-tailed Student's t-test or Mann-Whitney U-test was used when two groups were compared. For comparison of more than two groups, the one-way ANOVA with Bonferroni's post-test was applied. Correlation analysis was performed between the level of heart fibrosis and EF using GraphPad Prism 6.0d software. All P values below 0.05 were considered significant.

Both fibrosis and inflammation are closely associated with aging (18). The complex mechanisms involved in cellular deterioration with aging include the accumulation of DNA damage, mitochondrial dysfunction, increased susceptibility to apoptosis, telomere length shortening, epigenetic changes as well as oxidative stress (19, 20). It is known that elderly people experience significant changes in the function of their immune system, including a decline in the adaptive immune system, which creates an imbalance between adaptive and innate immune responses (21). Generally, aging leads to a more pro-inflammatory environment (22), with higher numbers of neutrophils and an increase in ROS production (5, 20) coupled with an increased susceptibility to pathogens and a higher incidence of inflammatory diseases (21), such as neurodegenerative disorders, rheumatoid arthritis, osteoporosis, diabetes, cardiovascular disease as well as thrombosis (23). Intriguingly, many of these illnesses have been reported to involve NETs.

Both the heart and the lung appear to be susceptible to age-related fibrosis. In cardiac aging, fibrotic remodeling may lead to diastolic dysfunction due to increased ventricular stiffness and, possibly, systolic heart failure (26), which is the most common cause for hospitalization for patients older than 65 years (27). In addition, cardiac injury by coronary artery disease or perimyocarditis can add to the fibrotic changes of the aging heart, making it even more important to understand the mechanisms underlying this process.

Fibrotic lung diseases are characterized by enhanced collagen deposition in the airways, including the alveolar walls, and subsequent disturbance of pulmonary gas-exchange. Excessive fibrotic tissue remodeling is a predominant feature of many chronic lung diseases. Fibrotic lung diseases affect a large part of the older population (28-30) and include chronic obstructive pulmonary disease (COPD), fibrotic reactions after acute or chronic lung infections, inhalation of pulmonary irritants, autoimmune or allergic diseases and idiopathic pulmonary fibrosis (IPF) an aggressive form of lung fibrosis with no proven treatment option. Importantly, both COPD and IPF are again clearly associated with aging (30, 31). Given the need for a better understanding of the complex mechanisms linking inflammation to fibrosis and aging, the goal of this study was to determine if there is interplay between PAD4/NETs, fibrosis and aging.

Results

Neutrophil Susceptibility to Form NETs Increases with Mouse Age

There are many changes that occur in the aging immune system, including an increase in hematopoietic stem cells of the myeloid lineage versus cells of the lymphoid lineage (34). To further study the effect of aging in mice, we examined blood and neutrophils from young (8-16 weeks) and old (24-27 months) mice obtained from the NIH's NIA C57BL/6 Aged Rodent Colony. We were able to confirm that in these mice, neutrophil counts were elevated with age (FIG. 5A), along with platelet counts (FIG. 5B). Using citrullinated histone H3 (H3Cit) as a biomarker of PAD4 activity and neutrophil priming for NETosis, we examined basal levels of circulating H3Cit+ cells and found that a greater percentage of neutrophils were primed toward NETosis in the old mice (FIG. 5C). We also saw that a higher percentage of circulating leukocytes were neutrophils in the old mice using the neutrophil-specific marker Ly6G (FIG. 5D). To evaluate whether neutrophils from the older animals had a greater tendency to release NETs, we isolated peripheral blood neutrophils and stimulated them with calcium ionophore or PMA. We found that after incubation, both with or without stimulation neutrophils from older mice had a greater propensity to form NETs as quantified by microscopy (FIG. 5E). Taken together, these observations indicate that in aging mice, NET formation is likely to be exacerbated. We hypothesized that increased NETosis, and the deleterious effects of NET formation, may lead to organ fibrosis. To study this, we focused on spontaneous organ fibrosis that occurs with natural aging in mice.

PAD4$^{-/-}$ Mice are Protected from Age-Related Decline in Heart Function

Figure 6A:
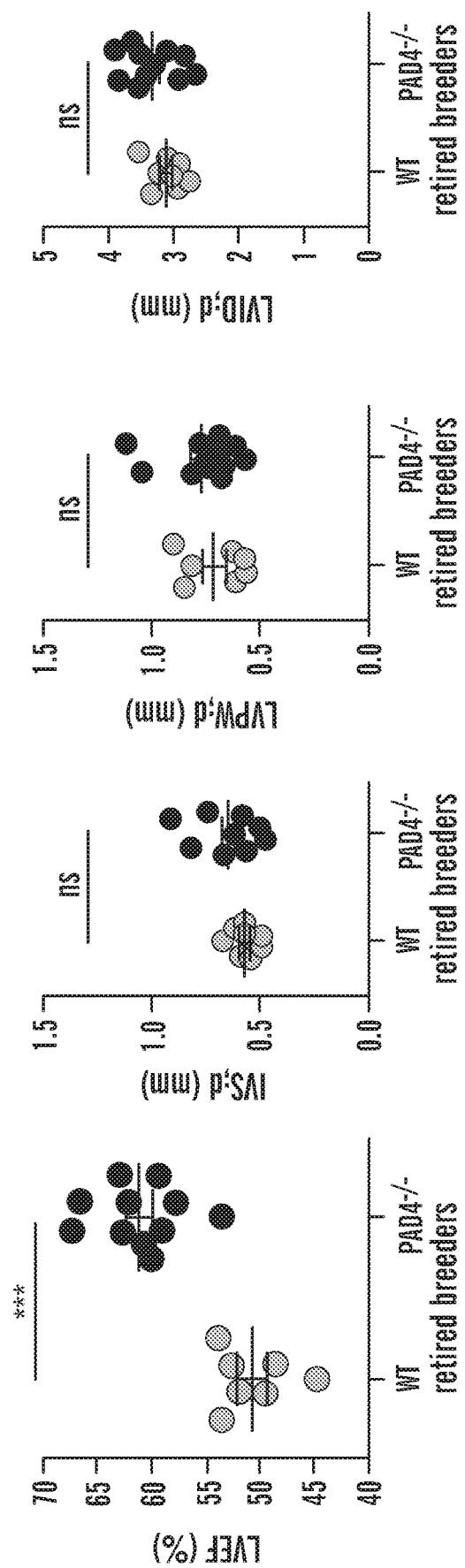
FIGS. 6A to 6E are graphs and images indicating that $PAD4^{-/-}$ mice are protected from age-related decline in systolic and diastolic heart function compared to WT mice.
Figure 6B:
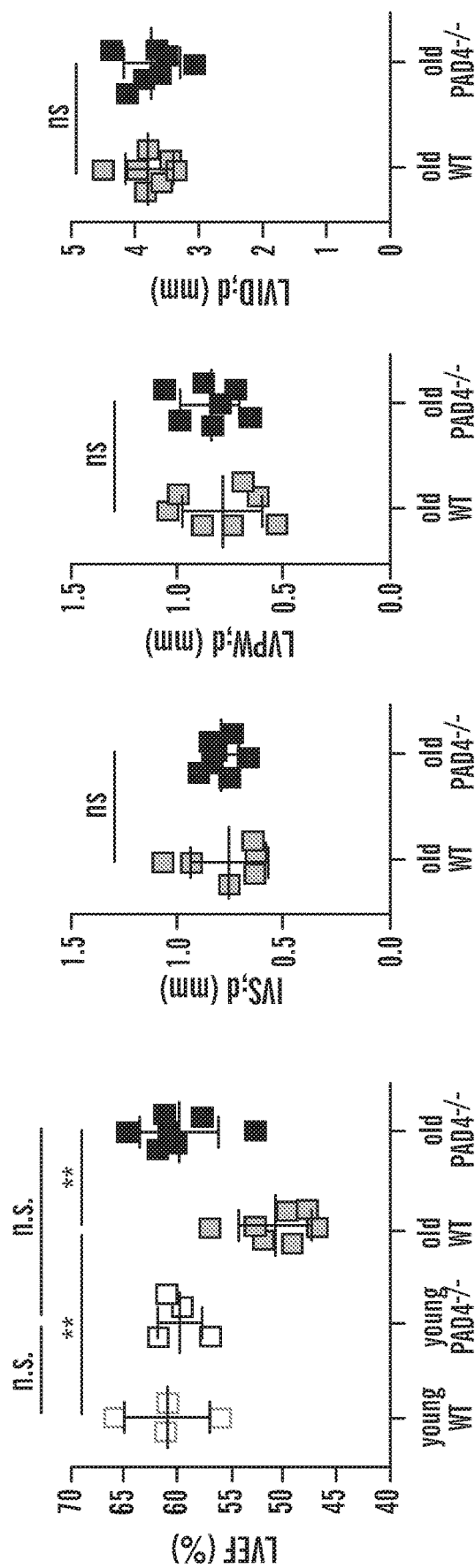

In C57BL/6 mice, NETosis is dependent on the histone modifying enzyme PAD4. Using PAD4$^{-/-}$ mice or DNase 1 infusion in WT mice, our group has previously shown that extracellular DNA/NETs have deleterious effects on heart function in the setting of acute myocardial injury (11). Therefore, we hypothesized that increased NETosis in old WT mice might constitute a chronic insult to the myocardium, resulting in a decline of heart function, and that reduction of NETosis in PAD4$^{-/-}$ mice might have protective effects. We performed echocardiography on WT and PAD4$^{-/-}$ retired breeders (12-17 months old), using age- and sex-matched groups of males and females. The mice were housed in the same animal room and had received an enriched "reproduction diet" throughout their life. Blood cell counts, body weights and blood pressure were not significantly different between the two genotypes (Table 2). We evaluated the left ventricular ejection fraction (LVEF) of these animals (FIG. 6A) and found that WT retired breeders showed a decline in their LVEF to 50.7%, consistent with literature on heart function in aging WT mice (35). Surprisingly, however, old PAD4$^{-/-}$ retired breeders retained a significantly better heart function with an average LVEF of 61.2%, comparable to the LVEF of young mice (FIG. 6B, first panel). No differences were seen between male and female mice. End-diastolic dimensions of the heart such as the diameter of the interventricular septum (IVS;d), the left ventricular posterior wall (LVPW;d) and left ventricular inner diameter (LVID;d) were assessed in both groups of mice (FIG. 2A) to check for possible significant dimensional differences such as severe ventricular dilation or wall hypertrophy that could underlie the observed changes in heart function. None of the measured structural parameters yielded significant differences between the two genotypes, suggesting that myocardial contractility and thus heart function itself is compromised in old WT but not PAD4$^{-/-}$ breeders.

Figure 6D:
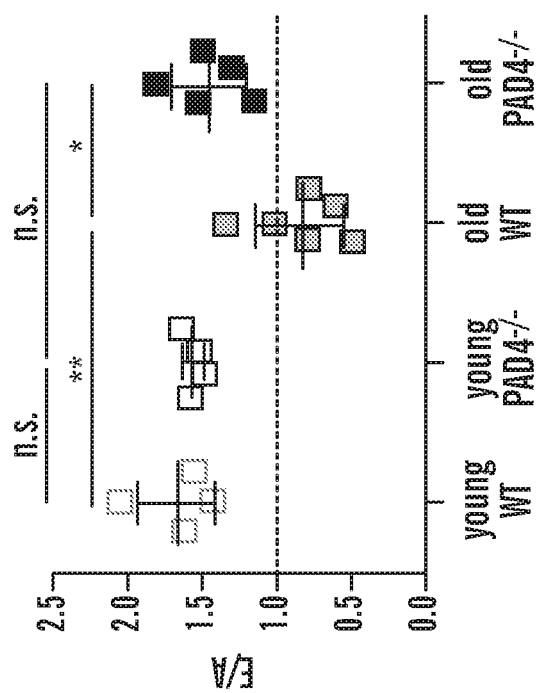
Figure 6C:
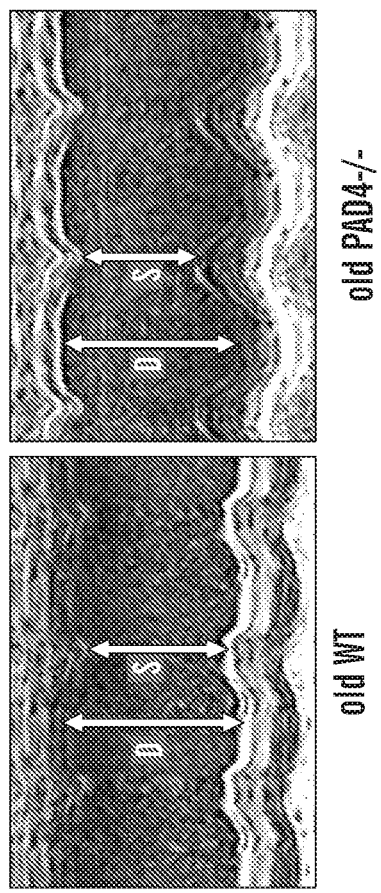

To exclude the possible effects of the reproduction diet received by the retired breeders, we repeated all echocardiographic measurements on groups of WT and PAD4$^{-/-}$ mice that were allowed to age on standard lab diet (FIG. 6B, 6C). Old WT and PAD4$^{-/-}$ mice were 14-18 months old, age- and sex-matched and housed in the same animal room. In addition, LVEF was measured in young gender-matched mice (6-8 weeks) on standard diet. Again, the old WT mice showed a decline in LVEF (FIG. 6B) compared to the young WT mice, with similar LVEF values to those observed in the retired WT breeders. This indicates that the reduction in heart function in old mice was independent of the dietary factors in our study. In this second group, the old PAD4$^{-/-}$ mice again had a significantly higher mean LVEF that was comparable to the means seen in young PAD4$^{-/-}$ or WT mice (FIG. 6B, first panel), corroborating that PAD4$^{-/-}$ mice are protected from an age-dependent decline in systolic heart function. Measurement of structural parameters again showed similar heart dimensions for old WT and PAD4$^{-/-}$ mice on standard diet with no significant differences for IVS;d, LVPW;d and LVID;d (FIG. 6B, 6C).

Figure 6E:
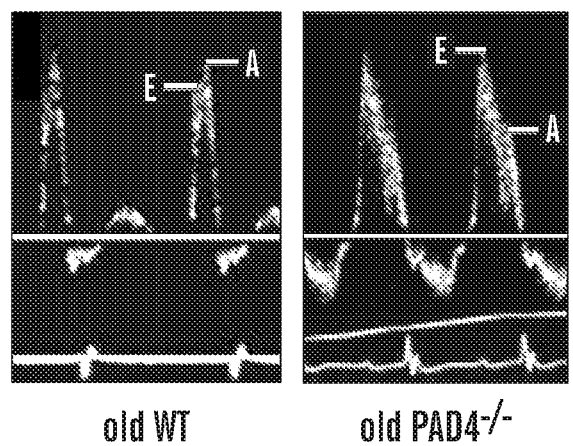
Figure 7A:
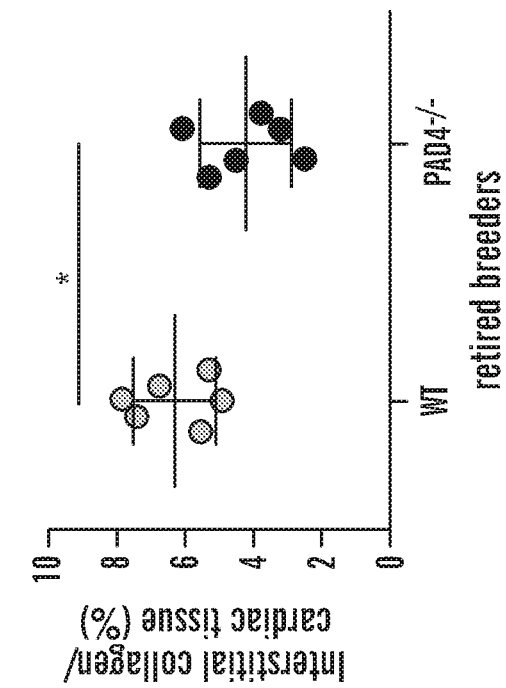
Figure 7B:
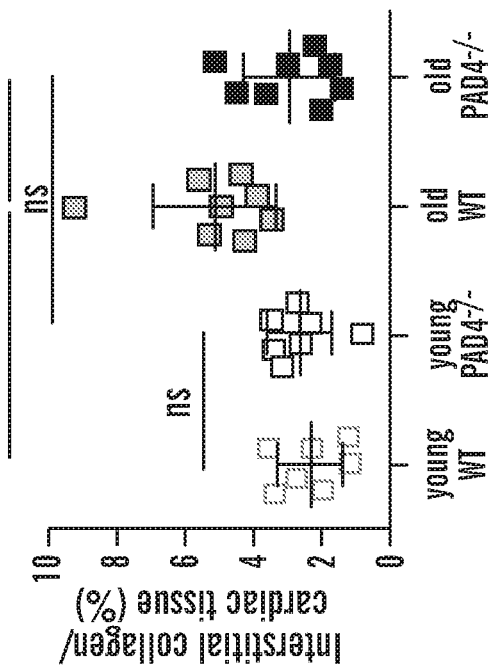

In contrast to the notable decline in LVEF seen in mice with old age, in humans, age-associated decline of heart function is mostly associated with diastolic dysfunction (36, 37). For that reason, we evaluated signs of diastolic dysfunction in a set of old WT (14-20 months) and old PAD4$^{-/-}$ (18 months) mice on standard diet and compared to young WT and PAD4$^{-/-}$ (2 months) mice. Specifically, the mitral inflow pattern was measured by echocardiography (FIGS. 6D and 6E) and the ratio between the E wave (representing the early, passive filling of the ventricle during diastole) and the A wave (representing the active filling of the ventricle by atrial contraction) was calculated. Representative images are shown in FIG. 6E. Generally, an E'A ratio of less than 1 is considered a sign of impaired ventricular relaxation and, hence, diastolic dysfunction, which can be caused by increased stiffness of the heart. In the old WT non-breeder mice, the average E'A ratio was 0.83, corroborating our previous observation of heart dysfunction in these mice (FIGS. 6D and 6E left panel). In contrast, none of the PAD4$^{-/-}$ old non-breeders showed signs of diastolic dysfunction: the average E'A ratio was 1.44 and significantly higher compared to old WT mice (FIGS. 6D and 6E, right panel). Unlike the old WT mice, old PAD4 did not have a significant decline in E'A ratio compared to young PAD4$^{-/-}$ mice. Thus, only in the PAD4$^{-/-}$ mice was the heart function preserved in old age PAD4$^{-/-}$ Mice have Significantly Less Interstitial Myocardial Fibrosis than WT Mice As old WT mice had clearly reduced heart function compared to old PAD4$^{-/-}$ mice without significant changes in heart dimensions, we aimed to determine if there were tissue changes in the myocardium. As organ fibrosis is a form of tissue remodeling often associated with old age and chronic inflammation, it seemed possible that the functional changes were due to an increase in myocardial fibrosis with age. We therefore harvested the hearts of WT and PAD4 retired breeders (n=6) and assessed interstitial heart fibrosis by Sirius red stain, which is used to identify and quantify collagen in cardiac tissue (32, 38, 39) (FIGS. 7A, 7C and 7D left panels). Perivascular staining was excluded from this analysis. Interestingly, WT retired breeders showed significantly more interstitial fibrosis than the age-matched 12-17 months PAD4$^{-/-}$ mice (FIG. 7A). In contrast, Sirius red-positive collagen fibers in the PAD4$^{-/-}$ breeder hearts were mainly located around vessels with little interstitial fibrosis (FIG. 7C). We performed the same analysis in the old WT and PAD4$^{-/-}$ non-breeders and found a similar difference between the WT and the PAD4$^{-/-}$ mice (FIG. 7B). Additionally, the hearts of young WT and PAD4$^{-/-}$ mice were assessed to determine whether a fibrosis difference between the genotypes was already present at an early age. At 6-8 weeks WT and PAD4$^{-/-}$ mice had comparably low interstitial heart fibrosis (FIG. 7B), indicating that the observed difference between WT and PAD4 $^{-/-}$ mice was indeed an age-related phenomenon. Remarkably, in the old PAD4 $^{-/-}$ non-breeders, the amount of fibrotic tissue remained similar to that of young PAD4$^-$ or WT mice, indicating that those old mice were protected from age-related myocardial interstitial fibrosis. Increased fibrosis in old WT compared to old PAD4$^{-/-}$ myocardium could also be observed qualitatively by Masson's trichrome staining (FIG. 7D, right panels), another type of staining commonly used to visualize collagen and fibrotic tissue changes (40, 41).

In spite of the significant visible difference in interstitial fibrosis between old WT and PAD4$^{-/-}$ mice, the determined percentage of interstitial fibrotic area appeared low. Therefore, we wondered whether the difference in fibrotic tissue within the heart could explain the difference in functionality in the two groups. Correlation analysis of level of heart fibrosis and LVEF of all mice was performed and indeed showed a significant (P<0.03) negative correlation, with a correlation coefficient (r) of −0.44. Although this result does not exclude additional factors in the development of heart dysfunction, it is highly probable that fibrosis determines tissue properties such as stiffness (26, 42) and thus organ function in these mice.

Age-Related Interstitial Pulmonary Fibrosis is Reduced in PAD4$^{-/-}$ Mice Compared to WT Mice After the surprising finding that PAD4$^{-/-}$ mice were protected from myocardial interstitial fibrosis in old age, we sought to extend our study to a second organ system that is highly susceptible to age-/inflammatory disease-related fibrosis. We assessed pulmonary interstitial fibrosis for both WT and PAD4$^{-/-}$ genotypes in the retired breeders and also in the old non-breeders and in young mice. The lungs of retired PAD4$^{-/-}$ breeders also had significantly less organ fibrosis as assessed by Masson's trichrome stain, compared to WT retired breeders (FIG. 8A) In the old mice on standard lab diet, the difference was also highly significant (FIG. 8B, 8C). Compared to young mice, both WT and PAD4$^{-/-}$ old mice showed an age-related increase in collagen deposition in the lung (FIG. 8A) However, in the WT mice, this increase was more pronounced.

Thus, our data show that aging is associated with an increase of interstitial fibrosis in different organs as determined by two different histochemical stains for collagen. PAD4$^{-/-}$ mice are, to a great degree, protected from this age-associated fibrosis.

DISCUSSION

Understanding the mechanisms leading to age-related organ dysfunction is essential for providing adequate care for our rapidly aging population. Thus, the goal of the present study was to investigate the interplay between aging, PAD4/NETs and organ function.

In spite of their proposed protective role in infectious diseases (6), NETs and their components are cytotoxic, pro-inflammatory and pro-thrombotic (10, 12, 43). Elevated levels of NETs are associated with a number of non-infectious diseases such as autoimmune disease (44-46), arteriosclerosis (47), cancer (16), DVT (14, 48) and myocardial infarction (11), all of which present a growing challenge to the health care system as the incidence of these diseases increases dramatically with age. Excessive NET formation is not only a side-product of these diseases, but NETs themselves can also negatively impact organ function as we have recently shown in an acute model of MI/R (11). Mice with a defect in forming NETs because they lack the enzyme PAD4 maintain a significantly better heart function after acute MI/R (11) and are also protected from venous thrombosis (13) that too may be triggered by hypoxia (49).

While these diseases in which NETs are implicated have a higher incidence in old age, neutrophil function and the predisposition to form NETs itself may be altered in the aging individual. It is known that the balance between innate immunity and adaptive immunity shifts towards innate immunity with a decrease in lymphocytes accompanied by either an increase or no change in neutrophil counts in older people (50, 51). An increase in neutrophil counts and neutrophil percent of total leukocytes was found in the old mice in our study compared to young mice. In humans, the expansion of the neutrophil population is accompanied by an increase in ROS production by the neutrophils (5). Interestingly, ROS have been shown to be inducers of NETosis (25, 52), thus providing a possible link between old age and NETosis. In addition, aging humans are known to have elevated platelet counts, as was also shown in our animal model. Interestingly, activation of platelets through TLR4 and their subsequent interactions with neutrophils have been proposed to stimulate NETosis (53). In our study, the propensity of neutrophils from older mice for PAD4-mediated histone citrullination and NET formation was significantly elevated compared to young mice after exposure to PMA, a ROS-dependent inducer of NETosis, and ionomycin, a ROS-independent stimulator that directly induces calcium influx into the cells and activates PAD4 (25). Even without stimulation, neutrophils from old mice had higher baseline values of H3Cit and produced more NETs after isolation. To our knowledge this is the first study evaluating NET formation in peripheral blood neutrophils from aging mice. One previous publication showed that neutrophils that had extravasated into the peritoneum had a reduced propensity to form NETs in older mice (54), but this recruited peritoneal neutrophil population is likely modified/activated by the transmigration and less likely to form NETs (55).

To assess whether organ function in old age was affected by the excessive ability of the old mice to form cytotoxic NETs, we measured heart function in old mice that either could form NETs (WT) or were defective in NETosis (PAD4$^{-/-}$), both in retired breeders and in mice that had received standard lab diet throughout their life. We chose this organ system as our group has previously shown in an acute model of MI/R that the PAD4$^{-/-}$ mice are protected from a decline in heart function compared to WT mice. Aging can cause myocardial damage via excessive ROS production by mitochondria-rich cardiomyocytes (56), and extracellular ROS augment neutrophil-endothelial interactions (57). We were thus interested whether in old age, which is accompanied by an elevated activation of NETosis, a long-term release of NETs would also lead to differences in heart function. Interestingly, we observed a significant difference between both the systolic and the diastolic functional measurements in old WT versus old PAD4$^{-/-}$ mice. While WT mice had an age-related, expected decline of LVEF with values very similar to those previously reported in the literature (35), LVEF in the old PAD4$^{-/-}$ mice remained comparable to that of young mice, both for systolic (LVEF) as well as diastolic (E/A ratio;) parameters. Therefore, the aging mouse heart could be undergoing chronic injury due to NET formation over time, negatively affecting heart function even in the absence of a specific event such as myocardial infarction.

Age-related structural remodeling of the human heart and decline of heart function is associated with cardiomyocyte hypertrophy and interstitial fibrosis. In young, healthy hearts, myocytes and myocardial bundles are surrounded by thin layers of connective tissue, the endomysium and perimysium, respectively. In contrast, with age, extracellular matrix proteins accumulate in the interstitium and result in endomysial and perimysial fibrosis (42). We used Sirius red staining to identify collagen in the myocardium and to assess interstitial fibrosis in the old and young WT mice. We found an increase in interstitial fibrosis in the old WT mice. However, such an age-related increase was absent in old PAD4$^{-/-}$ mice. While collagen and other extracellular matrix (ECM) components play an important role in maintaining tissue integrity and provide "healthy signaling," it is likely that excessive ECM accumulation reduces ventricular compliance and impairs cardiac function, both diastolic and systolic (42), as we have seen in the old WT mice. That an increase in interstitial fibrosis is a relevant factor in the age-related functional decline of the WT hearts was further corroborated by an inverse correlation between the extent of interstitial fibrosis and the LVEF of mice.

Another organ highly susceptible to fibrosis is the lung (28, 30). Here, however, the age-related fibrosis we observed was only in part dependent on PAD4 expression. Respiration exposes the airways of the lung to the outside world and injury leading to fibrosis could be contributed by minor infections resulting in injurious cytokine production and/or inhalation of particulate matter. However, even in the old lungs PAD4-deficiency significantly reduced fibrosis, which might lead to improved lung performance.

The reduction of interstitial collagen in the PAD4$^{-/-}$ mice and the protection from heart malfunction is striking and brings up the question as to why PAD4$^{-/-}$ mice would be protected from fibrosis in old age. As mentioned above, histones, the main protein component of NETs (58), have been shown to have cytotoxic effects on endothelium and epithelium (10, 59). Chronic elevation of these components in tissue might therefore lead to perpetual injury and the formation of excess ECM. Furthermore, neutrophil elastase, a protease which is released along with NETs, has been shown to directly contribute to lung fibrosis in an animal model of bleomycin-induced lung injury (60). A recently published study proposed a direct link between NETs and fibrosis (61). In this study, NETs promoted differentiation of lung fibroblasts in culture into a myofibroblast phenotype which in turn demonstrated increased connective tissue growth factor expression, collagen production and proliferation/migration. It is therefore reasonable to hypothesize that in vivo, NETs may similarly modify cellular behavior, thus promoting fibrosis.

Our results suggest that old age per se can be seen as a "NET-inducing state" with NET-dependent consequences to the organism. However, examining the organ function of old mice or aging humans, the damage to any organ system is likely the sum of insults over a lifetime. The NET-inducing events that might contribute to organ dysfunction include hypoxia, mechanical injury and various types of infections. As humans are much more exposed to such stressors than mice living in a protected specific pathogen-free environment, one would expect the unfavorable effects of life to be of even more consequence in humans than in laboratory mice.

Our study on aging in mice indicates that limiting PAD4 activity and excessive NET production in known NET-inducing diseases, especially in old age, would be beneficial. NET-targeted therapeutics could involve digesting NETs with DNases, inhibiting their formation with agents such as PAD4 inhibitors, or neutralizing their toxic components such as histones or elastase (10, 62). These approaches will have positive long-term effects on organ function and perhaps even longevity of individuals.

Example 2 References

1. Mayadas T N, Cullere X, & Lowell C A (2014) The Multifaceted Functions of Neutrophils. *Annu Rev Pathol* 9:181-218.
2. Clark R A (1999) Activation of the Neutrophil Respiratory Burst Oxidase. *J Infect Dis* 179 Suppl 2:S309-317.
3. Siwik D A, Pagano P J, & Colucci W S (2001) Oxidative Stress Regulates Collagen Synthesis and Matrix Metalloproteinase Activity in Cardiac Fibroblasts. *Am J Physiol Cell Physiol* 280(1):C53-60.
4. Sirker A, Zhang M, Murdoch C, & Shah A M (2007) Involvement of Nadph Oxidases in Cardiac Remodelling and Heart Failure. *Am J Nephrol* 27(6):649-660.
5. Ogawa K, Suzuki K, Okutsu M, Yamazaki K, & Shinkai S (2008) The Association of Elevated Reactive Oxygen Species Levels from Neutrophils with Low-Grade Inflammation in the Elderly. *Immun Ageing* 5:13.
6. Brinkmann V, et al. (2004) Neutrophil Extracellular Traps Kill Bacteria. *Science* 303(5663):1532-1535.
7. Wang Y, et al. (2009) Histone Hypercitrullination Mediates Chromatin Decondensation and Neutrophil Extracellular Trap Formation. *J Cell Biol* 184(2):205-213.
8. De Meyer S F, Suidan G L, Fuchs T A, Monestier M, & Wagner D D (2012) Extracellular Chromatin Is an Important Mediator of Ischemic Stroke in Mice. *Arterioscl Thromb* Vasc Biol 32(8): 1884-1891.
9. Kolaczkowska E & Kubes P (2013) Neutrophil Recruitment and Function in Health and Inflammation. *Nat Rev Immunol* 13(3): 159-175.

10. Xu J, et al. (2009) Extracellular Histones Are Major Mediators of Death in Sepsis. *Nat Med* 15(11): 1318-1321.
11. Savchenko A S, et al. (2014) Vwf-Mediated Leukocyte Recruitment with Chromatin Decondensation by Pad4 Increases Myocardial Ischemia/Reperfusion Injury in Mice. *Blood* 123(1):141-148.
12. Brill A, et al. (2012) Neutrophil Extracellular Traps Promote Deep Vein Thrombosis in Mice. *J Thromb Haemost* 10(1):136-144.
13. Martinod K, et al. (2013) Neutrophil Histone Modification by Peptidylarginine Deiminase 4 Is Critical for Deep Vein Thrombosis in Mice. *Proc Natl Acad Sci USA* 110(21):8674-8679.
14. Fuchs T A, et al. (2010) Extracellular DNA Traps Promote Thrombosis. *Proc Natl Acad Sci USA* 107(36): 15880-15885.
15. Thomas G M, et al. (2012) Extracellular DNA traps are associated with the pathogenesis of TRALI in humans and mice. *Blood* 119(26):6335-6343.
16. Demers M, et al. (2012) Cancers Predispose Neutrophils to Release Extracellular DNA Traps That Contribute to Cancer-Associated Thrombosis. *Proc NatlAcad Sci USA* 109(32):13076-13081.
17. Cools-Lartigue J, et al. (2013) Neutrophil Extracellular Traps Sequester Circulating Tumor Cells and Promote Metastasis. *J Clin Invest*.
19. Varagic J, Susic D, & Frohlich E (2001) Heart, Aging, and Hypertension. *Curr Opin Cardiol* 16(6):336-341.
20. Kapetanaki M G, Mora A L, & Rojas M (2013) Influence of Age on Wound Healing and Fibrosis. *J Pathol* 229(2): 310-322.
21. Sohal R S & Weindruch R (1996) Oxidative Stress, Caloric Restriction, and Aging. *Science* 273(5271):59-63.
22. Aw D, Silva A B, & Palmer D B (2007) Immunosenescence: Emerging Challenges for an Ageing Population. *Immunology* 120(4):435-446.
23. Meyer K C, Rosenthal N S, Soergel P, & Peterson K (1998) Neutrophils and Low-Grade Inflammation in the Seemingly Normal Aging Human Lung. *Mech Ageing Dev* 104(2):169-181.
24. Tabas I & Glass C K (2013) Anti-Inflammatory Therapy in Chronic Disease: Challenges and Opportunities. *Science* 339(6116):166-172.
25. Akong-Moore K, Chow O A, von Kockritz-Blickwede M, & Nizet V (2012) Influences of Chloride and Hypochlorite on Neutrophil Extracellular Trap Formation. *PloS One* 7(8):e42984.
26. Parker H, Dragunow M, Hampton M B, Kettle A J, & Winterbourn C C (2012) Requirements for Nadph Oxidase and Myeloperoxidase in Neutrophil Extracellular Trap Formation Differ Depending on the Stimulus. *J Leukoc Biol* 92(4):841-849.
27. Wei J Y (1992) Age and the Cardiovascular System. *N Engl JMed* 327(24):1735-1739.
28. DeFrances C J, Cullen K A, & Kozak L J (2007) National Hospital Discharge Survey:
2005 Annual Summary with Detailed Diagnosis and Procedure Data. *Vital Health Stat* 13 (165):1-209.
29. Navaratnam V, et al. (2011) The Rising Incidence of Idiopathic Pulmonary Fibrosis in the U.K. *Thorax* 66(6): 462-467.
30. Afonso A S, Verhamme K M, Sturkenboom M C, & Brusselle G G (2011) Copd in the General Population: Prevalence, Incidence and Survival. *Respir Med* 105(12): 1872-1884.
31. van Durme Y M, et al. (2009) Prevalence, Incidence, and Lifetime Risk for the Development of Copd in the Elderly: The Rotterdam Study. *Chest* 135(2):368-377.
32. Wolters P J, Collard H R, & Jones K D (2014) Pathogenesis of Idiopathic Pulmonary Fibrosis. *Annu Rev Pathol* 9:157-179.
33. Junqueira L C, Bignolas G, & Brentani R R (1979) Picrosirius Staining Plus Polarization Microscopy, a Specific Method for Collagen Detection in Tissue Sections. *Histochem J* 11(4):447-455.
34. Thevenaz P & Unser M (2007) User-Friendly Semiautomated Assembly of Accurate Image Mosaics in Microscopy. *Microsc Res Tech* 70(2):135-146.
35. Beerman I, et al. (2010) Functionally Distinct Hematopoietic Stem Cells Modulate Hematopoietic Lineage Potential During Aging by a Mechanism of Clonal Expansion. *Proc NatlAcad Sci USA* 107(12):5465-5470.
36. Yang B, Larson D F, & Watson R (1999) Age-Related Left Ventricular Function in the Mouse: Analysis Based on in Vivo Pressure-Volume Relationships. *Am J Physiol* 277(5 Pt 2):H1906-1913.
36. Loffredo F S, Nikolova A P, Pancoast J R, & Lee R T (2014) Heart Failure with Preserved Ejection Fraction: Molecular Pathways of the Aging Myocardium. *Circ Res* 115(1):97-107.
37. Pugh K G & Wei J Y (2001) Clinical Implications of Physiological Changes in the Aging Heart. *Drugs Aging* 18(4):263-276.
38. Namba T, et al. (1997) Regulation of Fibrillar Collagen Gene Expression and Protein Accumulation in Volume-Overloaded Cardiac Hypertrophy. *Circulation* 95(10): 2448-2454.
39. Ammarguellat F, Larouche I, & Schiffrin E L (2001) Myocardial Fibrosis in Doca-Salt Hypertensive Rats: Effect of Endothelin Eta Receptor Antagonism. *Circulation* 103(2):319-324.
40. Savchenko A S, et al. (2014) Neutrophil Extracellular Traps Form Predominantly During the Organizing Stage of Human Venous Thromboembolism Development. *J Thromb Haemost*.
41. Bancroft J, Gamble, M (2008) Connective Tissue and Stains. *Theory and Practice of Histological Techniques*, ed Bancroft J (Churchill-Livingston Elsevier, London), pp 135-160.
42. Frangogiannis ABaNG (Aging and Cardiac Fibrosis. *Aging and Disease*.
43. Demers M & Wagner D D (2014) Netosis: A New Factor in Tumor Progression and Cancer-Associated Thrombosis. *Semin Thromb Hemost* 40(3):277-283.
44. Hakkim A, et al. (2010) Impairment of Neutrophil Extracellular Trap Degradation Is Associated with Lupus Nephritis. *Proc NatlAcad Sci USA* 107(21):9813-9818.
45. Kessenbrock K, et al. (2009) Netting Neutrophils in Autoimmune Small-Vessel Vasculitis. *Nat Med* 15(6): 623-625.
46. Dwivedi N, et al. (2012) Felty's Syndrome Autoantibodies Bind to Deiminated Histones and Neutrophil Extracellular Chromatin Traps. *Arthritis Rheum* 64(4): 982-992.
47. Borissoff J I, et al. (2013) Elevated Levels of Circulating DNA and Chromatin Are Independently Associated with Severe Coronary Atherosclerosis and a Prothrombotic State. *Arterioscler Thromb Vasc Biol* 33(8):2032-2040.
48. Diaz J A F T, Jackson T O, Stabler C C, Kremer Hovinga J A, Lämmle B, Henke P K, Myers D D Jr, Wagner D D, Wakefield T W and the Michigan Research Venous Group (2013) Plasma DNA Is Elevated in Patients with Deep Vein Thrombosis. *J Vasc Surg: Venous and Lym Dis* 1(4):341-348.
49. Brill A, Suidan G L, & Wagner D D (2013) Hypoxia, Such as Encountered at High Altitude, Promotes Deep Vein Thrombosis in Mice. *J Thromb Haemost* 11(9):1773-1775.
50. Cakman I, Rohwer J, Schutz R M, Kirchner H, & Rink L (1996) Dysregulation between Th1 and Th2 T Cell Subpopulations in the Elderly. *Mech Ageing Dev* 87(3): 197-209.
52. Schroder A K & Rink L (2003) Neutrophil Immunity of the Elderly. *Mech Ageing Dev* 124(4):419-425.
53. Li P, et al. (2010) Pad4 Is Essential for Antibacterial Innate Immunity Mediated by Neutrophil Extracellular Traps. *J Exp Med* 207(9): 1853-1862.
54. Clark S R, et al. (2007) Platelet Tlr4 Activates Neutrophil Extracellular Traps to Ensnare Bacteria in Septic Blood. *Nat Med* 13(4):463-469.
55. Tseng C W, et al. (2012) Innate Immune Dysfunctions in Aged Mice Facilitate the Systemic Dissemination of Methicillin-Resistant *S. Aureus. PLoS One* 7(7):e41454.
56. Papayannopoulos V, Metzler K D, Hakkim A, & Zychlinsky A (2010) Neutrophil Elastase and Myeloperoxidase Regulate the Formation of Neutrophil Extracellular Traps. *J Cell Biol* 191(3):677-691.
57. Dai D F & Rabinovitch P S (2009) Cardiac Aging in Mice and Humans: The Role of Mitochondrial Oxidative Stress. *Trends Cardiovasc Med* 19(7):213-220.
58. Patel K D, Zimmerman G A, Prescott S M, McEver R P, & McIntyre T M (1991) Oxygen Radicals Induce Human Endothelial Cells to Express Gmp-140 and Bind Neutrophils. *J Cell Biol* 112(4):749-759.
59. Urban C F, et al. (2009) Neutrophil Extracellular Traps Contain Calprotectin, a Cytosolic Protein Complex Involved in Host Defense against *Candida Albicans. PLoS Path* 5(10):e1000639.
60. Saffarzadeh M, et al. (2012) Neutrophil Extracellular Traps Directly Induce Epithelial and Endothelial Cell Death: A Predominant Role of Histones. *PLoS One* 7(2): e32366.
61. Chua F, et al. (2007) Mice Lacking Neutrophil Elastase Are Resistant to Bleomycin-Induced Pulmonary Fibrosis. *Am J Pathol* 170(1):65-74.
62. Chrysanthopoulou A, et al. (2014) Neutrophil Extracellular Traps Promote Differentiation and Function of Fibroblasts. *J Pathol* 233(3):294-307.
63. Martinod K & Wagner D D (2014) Thrombosis: Tangled up in NETs. *Blood* 123(18):2768-2776.

```
Sequence Listing
PAD4 mRNA NCBI Ref Seq: NM_012387
                                                                    SEQ ID NO: 1
   1 acagccagag ggacgagcta gcccgacgat ggcccagggg acattgatcc gtgtgacccc 61 agagcagccc acccatgccg tgtgtgtgct gggcaccttg actcagcttg acatctgcag 121 ctctgccccct gaggactgca cgtccttcag catcaacgcc tccccagggg tggtcgtgga 181 tattgcccac ggccctccag ccaagaagaa atccacaggt tcctccacat ggcccctgga 241 ccctggggta gaggtgaccc tgacgatgaa agtggccagt ggtagcacag gcgaccagaa 301 ggttcagatt tcatactacg gacccaagac tccaccagtc aaagctctac tctacctcac 361 cggggtggaa atctccttgt gcgcagacat cacccgcacc ggcaaagtga agccaaccag 421 agctgtgaaa gatcagagga cctggacctg gggcccttgt ggacagggtg ccatcctgct 481 ggtgaactgt gacagagaca atctcgaatc ttctgccatg gactgcgagg atgatgaagt 541 gcttgacagc gaagacctgc aggacatgtc gctgatgacc ctgagcacga agacccccaa 601 ggacttcttc acaaaccata cactggtgct ccacgtggcc aggtctgaga tggacaaagt 661 gagggtgttt caggccacac ggggcaaact gtcctccaag tgcagcgtag tcttgggtcc 721 caagtggccc tctcactacc tgatggtccc cggtggaaag cacaacatgg acttctacgt 781 ggaggccctc gctttcccgg acaccgactt cccggggctc attaccctca ccatctccct 841 gctggacacg tccaacctgg agctccccga ggctgtggtg ttccaagaca gcgtggtctt 901 ccgcgtggcg ccctggatca tgaccccccaa cacccagccc ccgcaggagg tgtacgcgtg 961 cagtatttttt gaaaatgagg acttcctgaa gtcagtgact actctggcca tgaaagccaa 1021 gtgcaagctg accatctgcc ctgaggagga aacatggat gaccagtgga tgcaggatga 1081 aatggagatc ggctacatcc aagccccaca caaaacgctg cccgtggtct tcgactctcc 1141 aaggaacaga ggcctgaagg agtttcccat caaacgcgtg atgggtccag attttggcta 1201 tgtaactcga gggcccaaa caggggggtat cagtggactg gactcctttg ggaacctgga 1261 agtgagcccc ccagtcacag tcagggggcaa ggaatacccg ctgggcagga ttctcttcgg 1321 ggacagctgt tatcccagca atgacagccg gcagatgcac caggccctgc aggacttcct
```

```
1381 cagtgcccag caggtgcagg cccctgtgaa gctctattct gactggctgt ccgtgggcca
1441 cgtggacgag ttcctgagct tgtgccagc acccgacagg aagggcttcc ggctgctcct
1501 ggccagcccc aggtcctgct acaaactgtt ccaggagcag cagaatgagg gccacgggga
1561 ggccctgctg ttcgaaggga tcaagaaaaa aaaacagcag aaaataaaga acattctgtc
1621 aaacaagaca ttgagagaac ataattcatt tgtggagaga tgcatcgact ggaaccgcga
1681 gctgctgaag cgggagctgg gcctggccga gagtgacatc attgacatcc cgcagctctt
1741 caagctcaaa gagttctcta aggcggaagc ttttttcccc aacatggtga acatgctggt
1801 gctagggaag cacctgggca tccccaagcc cttcgggccc gtcatcaacg gccgctgctg
1861 cctggaggag aaggtgtgtt ccctgctgga gccactgggc tccagtgca ccttcatcaa
1921 cgacttcttc acctaccaca tcaggcatgg ggaggtgcac tgcggcacca acgtgcgcag
1981 aaagcccttc tccttcaagt ggtggaacat ggtgccctga gccatcttc cctggcgtcc
2041 tctccctcct ggccagatgt cgctgggtcc tctgcagtgt ggcaagcaag agctcttgtg
2101 aatattgtgg ctccctgggg gcggccagcc ctcccagcag tggcttgctt tcttctcctg
2161 tgatgtccca gtttcccact ctgaagatcc aacatggtc ctagcactgc acactcagtt
2221 ctgctctaag aagctgcaat aaagttttt taagtcactt tgtac
```

PAD4 amino acid sequence NCBI Ref Seq: NP_036519

SEQ ID NO: 2

```
  1 maqgtlirvt peqpthavcv lgtltqldic ssapedctsf sinaspgvvv diahgppakk
 61 kstgsstwpl dpgvevtltm kvasgstgdq kvqisyygpk tppvkallyl tgveislcad
121 itrtgkvkpt ravkdqrtwt wgpcgqgail lvncdrdnle ssamdcedde vldsedlqdm
181 slmtlstktp kdfftnhtlv lhvarsemdk vrvfqatrgk lsskcsvvlg pkwpshylmv
241 pggkhnmdfy vealafpdtd fpglitltis lldtsnlelp eavvfqdsvv frvapwimtp
301 ntqppqevya csifenedfl ksvttlamka kckliticpee enmddqwmqd emeigyiqap
361 hktlpvvfds prnrglkefp ikrvmgpdfg yvtrgpqtgg isgldsfgnl evsppvtvrg
421 keyplgrilf gdscypsnds rqmhqalqdf lsaqqvqapv klysdwlsvg hvdeflsfvp
481 apdrkgfrll lasprscykl feeeeneghg eallfegikk kkqqikilnil snktlrehns
541 fvercidwnr ellkrelgla esdiidipql fklkefskae affpnmvnml vlgkhlgipk
601 pfgpvingrc cleekvcsll eplglqctfi ndffftyhirh gevhcgtnvr rkpfsfkwwn
661 mvp
```

---

What is claimed is:

1. A method for treating skin wounds in a subject having diabetes, comprising administering a therapeutically effective amount of an anti-NET compound to the subject at a frequency that is sufficient to reduce accumulation of NETs during wound healing, and wherein the administration is over several days, weeks, or months, wherein the anti-NET compound consists of a DNase enzyme, and wherein nucleic acid is not delivered.

2. The method of claim 1, wherein the anti-NET compound is administered by local administration.

3. The method of claim 2, wherein the local administration is topical administration.

4. The method of claim 2, wherein the local administration is instillation.

5. The method of claim 1, wherein the anti-NET compound is administered by systemic administration.

6. The method of claim 1, wherein the anti-NET compound is administered by injection or infusion.

7. The method of claim 1, wherein the anti-NET compound is administered at a dose from 1 μg/kg to 50 mg/kg.

8. The method of claim 7, wherein the dose is 100 μg/kg to 100 mg/kg.

9. The method of claim 1, wherein the anti-NET compound is administered daily.

10. The method of claim 1, wherein the anti-NET compound is administered twice daily.

11. The method of claim 1, wherein the anti-NET compound is administered three times daily or four times daily.

12. The method of claim 1, wherein the anti-NET compound is administered for a period of 1 week.

13. The method of claim 1, wherein the anti-NET compound is administered for a period of 1 to 4 weeks.

14. The method of claim 1, wherein the DNase is a DNase 1.

15. The method of claim 1, wherein the subject has a slow healing cut or sore.

* * * * *

SEQUENCE LISTING

<160> NUMBER OF SEQ IDS: 2

<210> SEQ ID NO 1
<211> LENGTH: 2265
<212> TYPE: DNA
<213> ORGANISM: Homo sapiens

<400> SEQUENCE: 1

```
acagccagag ggacgagcta gcccgacgat ggcccagggg acattgatcc gtgtgacccc      60
agagcagccc acccatgccg tgtgtgtgct gggcaccttg actcagcttg acatctgcag     120
ctctgcccct gaggactgca cgtccttcag catcaacgcc tcccaggggg tggtcgtgga     180
tattgcccac ggccctccag ccaagaagaa atccacaggt tcctccacat ggcccctgga     240
ccctggggta gaggtgaccc tgacgatgaa agtggccagt ggtagcacag cgaccagaa      300
```

```
ggttcagatt tcatactacg acccaagac tccaccagtc aaagctctac tctacctcac    360
cggggtggaa atctccttgt gcgcagacat caccccgcacc ggcaaagtga agccaaccag   420
agctgtgaaa gatcagagga cctggacctg ggcccttgt ggacagggtg ccatcctgct    480
ggtgaactgt gacagagaca atctcgaatc ttctgccatg gactgcgagg atgatgaagt   540
gcttgacagc gaagacctgc aggacatgtc gctgatgacc ctgagcacga agaccccaa    600
ggacttcttc acaaaccata cactggtgct ccacgtggcc aggtctgaga tggacaaagt   660
gagggtgttt caggccacac ggggcaaact gtcctccaag tgcagcgtag tcttgggtcc   720
caagtggccc tctcactacc tgatggtccc cggtggaaag cacaacatgg acttctacgt   780
ggaggccctc gctttcccgg acaccgactt cccgggctc attaccctca ccatctccct    840
gctggacacg tccaacctgg agctccccga ggctgtggtg ttccaagaca gcgtggtctt   900
ccgcgtggcg ccctggatca tgaccccaa cacccagccc ccgcaggagg tgtacgcgtg   960
cagtattttt gaaaatgagg acttcctgaa gtcagtgact actctggcca tgaaagccaa  1020
gtgcaagctg accatctgcc ctgaggagga gaacatggat gaccagtgga tgcaggatga  1080
aatggagatc ggctacatcc aagccccaca caaaacgctg cccgtggtct tcgactctcc  1140
aaggaacaga ggcctgaagg agtttcccat caaacgcgtg atgggtccag attttggcta  1200
tgtaactcga gggccccaaa caggggtat cagtggactg gactcctttg ggaacctgga   1260
agtgagcccc ccagtcacag tcaggggcaa ggaatacccg ctgggcagga ttctcttcgg  1320
ggacagctgt tatcccagca atgacagccg gcagatgcac caggccctgc aggacttcct  1380
cagtgcccag caggtgcagg ccctgtgaa gctctattct gactggctgt ccgtgggcca   1440
cgtggacgag ttcctgagct tgtgccagc acccgacagg aagggcttcc ggctgctcct   1500
ggccagcccc aggtcctgct acaaactgtt ccaggagcag cagaatgagg ccacggggaa  1560
ggcccctgctg ttcgaaggga tcaagaaaaa aaaacagcag aaaataaaga acattctgtc  1620
aaacaagaca ttgagagaac ataattcatt tgtggagaga tgcatcgact ggaaccgcga  1680
gctgctgaag cgggagctgg gcctggccga gagtgacatc attgacatcc cgcagctctt  1740
caagctcaaa gagttctcta aggcggaagc ttttttcccc aacatggtga acatgctggt  1800
gctagggaag cacctgggca tccccaagcc cttcgggccc gtcatcaacg ccgctgctg   1860
cctggaggag aaggtgtgtt ccctgctgga gccactgggc tccagtgca ccttcatcaa   1920
cgacttcttc acctaccaca tcaggcatgg ggaggtgcac tgcggcacca acgtgcgcag  1980
aaagcccttc tccttcaagt ggtggaacat ggtgccctga gccatcttc cctggcgtcc   2040
tctccctcct ggccagatgt cgctgggtcc tctgcagtgt ggcaagcaag agctcttgtg  2100
aatattgtgg ctccctgggg gcggccagcc ctcccagcag tggcttgctt tcttctcctg  2160
tgatgtccca gtttcccact ctgaagatcc caacatggtc ctagcactgc acactcagtt  2220
ctgctctaag aagctgcaat aaagtttttt taagtcactt tgtac                  2265
```

<210> SEQ ID NO 2
<211> LENGTH: 663
<212> TYPE: PRT
<213> ORGANISM: Homo sapiens

<400> SEQUENCE: 2

Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser

-continued

```
                20                  25                  30
Ala Pro Glu Asp Cys Thr Ser Phe Ser Ile Asn Ala Ser Pro Gly Val
                35                  40                  45

Val Val Asp Ile Ala His Gly Pro Ala Lys Lys Lys Ser Thr Gly
            50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
                100                 105                 110

Val Glu Ile Ser Leu Cys Ala Asp Ile Thr Arg Thr Gly Lys Val Lys
            115                 120                 125

Pro Thr Arg Ala Val Lys Asp Gln Arg Thr Trp Thr Trp Gly Pro Cys
            130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
            195                 200                 205

Asp Lys Val Arg Val Phe Gln Ala Thr Arg Gly Lys Leu Ser Ser Lys
            210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
            275                 280                 285

Val Val Phe Arg Val Ala Pro Trp Ile Met Thr Pro Asn Thr Gln Pro
            290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
            355                 360                 365

Asp Ser Pro Arg Asn Arg Gly Leu Lys Glu Phe Pro Ile Lys Arg Val
            370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
            435                 440                 445
```

-continued

```
Asp Phe Leu Ser Ala Gln Gln Val Gln Ala Pro Val Lys Leu Tyr Ser
    450                 455                 460
Asp Trp Leu Ser Val Gly His Val Asp Glu Phe Leu Ser Phe Val Pro
465                 470                 475                 480
Ala Pro Asp Arg Lys Gly Phe Arg Leu Leu Leu Ala Ser Pro Arg Ser
                485                 490                 495
Cys Tyr Lys Leu Phe Gln Glu Gln Gln Asn Glu Gly His Gly Glu Ala
                500                 505                 510
Leu Leu Phe Glu Gly Ile Lys Lys Lys Gln Gln Lys Ile Lys Asn
                515                 520                 525
Ile Leu Ser Asn Lys Thr Leu Arg Glu His Asn Ser Phe Val Glu Arg
    530                 535                 540
Cys Ile Asp Trp Asn Arg Glu Leu Leu Lys Arg Glu Leu Gly Leu Ala
545                 550                 555                 560
Glu Ser Asp Ile Ile Asp Ile Pro Gln Leu Phe Lys Leu Lys Glu Phe
                565                 570                 575
Ser Lys Ala Glu Ala Phe Phe Pro Asn Met Val Asn Met Leu Val Leu
                580                 585                 590
Gly Lys His Leu Gly Ile Pro Lys Pro Phe Gly Pro Val Ile Asn Gly
                595                 600                 605
Arg Cys Cys Leu Glu Glu Lys Val Cys Ser Leu Leu Glu Pro Leu Gly
                610                 615                 620
Leu Gln Cys Thr Phe Ile Asn Asp Phe Phe Thr Tyr His Ile Arg His
625                 630                 635                 640
Gly Glu Val His Cys Gly Thr Asn Val Arg Arg Lys Pro Phe Ser Phe
                645                 650                 655
Lys Trp Trp Asn Met Val Pro
                660
```